US008946217B2

(12) United States Patent
Shuttleworth et al.

(10) Patent No.: US 8,946,217 B2
(45) Date of Patent: *Feb. 3, 2015

(54) PHARMACEUTICAL COMPOUNDS

(71) Applicant: F. Hoffman-La Roche AG, Basel (CH)

(72) Inventors: Stephen J. Shuttleworth, Slough (GB); Adrian J. Folkes, Slough (GB); Irina S. Chuckowree, Slough (GB); Nan Chi Wan, Slough (GB); Timothy C. Hancox, Slough (GB); Stewart J. Baker, Slough (GB); Sukhjit Sohal, Slough (GB); Mohammed A. Latif, Slough (GB)

(73) Assignee: F. Hoffmann-La Roche AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/307,364

(22) Filed: Jun. 17, 2014

(65) Prior Publication Data

US 2014/0294946 A1 Oct. 2, 2014

Related U.S. Application Data

(63) Continuation of application No. 13/950,966, filed on Jul. 25, 2013, now abandoned, which is a continuation of application No. 13/415,672, filed on Mar. 8, 2012, now abandoned, which is a continuation of application No. 12/789,773, filed on May 28, 2010, now Pat. No. 8,153,629, and a continuation of application No. 11/893,414, filed on Aug. 16, 2007, now Pat. No. 7,750,002, and a continuation of application No. PCT/GB2005/004129, filed on Oct. 25, 2005.

(51) Int. Cl.
  A61K 31/535 (2006.01)
  C07D 495/04 (2006.01)

(52) U.S. Cl.
  CPC .................. C07D 495/04 (2013.01)
  USPC ........................................ 514/234.5

(58) Field of Classification Search
  USPC ........................................ 514/234.5
  See application file for complete search history.

(56) References Cited

U.S. PATENT DOCUMENTS

| 3,475,429 | A | 10/1969 | Woitun et al. |
| 3,661,908 | A | 5/1972 | Woitun et al. |
| 3,763,156 | A | 10/1973 | Woitun et al. |
| 3,838,121 | A | 9/1974 | Woitun et al. |
| 4,007,187 | A | 2/1977 | Fauran et al. |
| 4,146,716 | A | 3/1979 | Cox et al. |
| 4,196,207 | A | 4/1980 | Webber et al. |
| 6,187,777 | B1 | 2/2001 | Norman et al. |
| 6,608,053 | B2 | 8/2003 | Hayakawa et al. |
| 6,838,457 | B2 | 1/2005 | Hayakawa et al. |
| 7,037,915 | B2 | 5/2006 | Hayakawa et al. |
| 7,173,029 | B2 | 2/2007 | Hayakawa et al. |
| 7,750,002 | B2 | 7/2010 | Shuttleworth et al. |
| 7,781,433 | B2 | 8/2010 | Chuckowree et al. |
| 8,153,629 | B2 | 4/2012 | Shuttleworth et al. |
| 8,247,397 | B2 | 8/2012 | Belvin et al. |
| 8,324,206 | B2 | 12/2012 | Chuckowree et al. |
| 8,685,968 | B2 | 4/2014 | Chuckowree et al. |
| 8,802,670 | B2 * | 8/2014 | Folkes et al. ............... 514/234.5 |
| 2003/0220365 | A1 | 11/2003 | Stewart et al. |
| 2008/0076758 | A1 | 3/2008 | Folkes et al. |
| 2012/0258966 | A1 | 10/2012 | Shuttleworth et al. |
| 2013/0317017 | A1 | 11/2013 | Shuttleworth et al. |

FOREIGN PATENT DOCUMENTS

| EP | 1277738 A1 | 1/2003 |
| GB | 1393161 | 5/1975 |
| WO | WO 2004/017950 | 3/2004 |
| WO | WO 2004/065391 A1 | 8/2004 |
| WO | WO 2006/046031 A1 | 5/2006 |

(Continued)

OTHER PUBLICATIONS

Bachman et al., "The PIK3CA gene is mutated with high frequency in human breast cancers", *Cancer Biology & Therapy*, 3(8), 772-775, Aug. 2004.
Berge et al., "Pharmaceutical Salts", *Journal of Pharmaceutical Sciences*, 66(1), 1-19, Jan. 1977.
Byrn et al., "Hydrates and Solvates", *Solid-State Chemistry of Drugs, Second Edition*, 233-247, 1999.
C. Garcia-Echeverria et al, "Drug discovery approaches targeting the PI3/Akt pathway in cancer", *Oncogene*, 27, 5511-5526, 2008.
*Cancer and Metastasis Reviews*, 17(1), 91-106, (1998).
*Cecil Textbook of Medicine*, 20th edition, vol. 2, pp. 1992-1996, (1996).
*Cecil Textbook of Medicine*, 20th edition, vol. 2, pp. 2050-2057, (1996).
Edgar et al., "Isoform-Specific Phosphoinositide 3-Kinase Inhibitors Exert Distinct Effects in Solid Tumors", *Cancer Research*, 70, 1164-1172 (2010).

(Continued)

*Primary Examiner* — Rebecca Anderson
(74) *Attorney, Agent, or Firm* — Viksnins Harris & Padys PLLP

(57) ABSTRACT

Fused pyrimidines of formula (I):

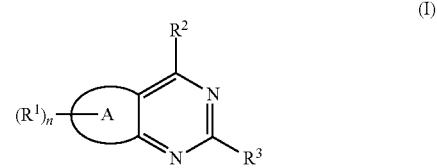

(I)

wherein $R^1$-$R^3$, A and n have any of the values described in the specification; and pharmaceutically acceptable salts thereof; have activity as inhibitors of PI3K and may thus be used to treat diseases and disorders arising from abnormal cell growth, function or behaviour associated with PI3 kinase such as cancer, immune disorders, cardiovascular disease, viral infection, inflammation, metabolism/endocrine disorders and neurological disorders. Processes for synthesizing the compounds are also described.

5 Claims, No Drawings

(56) References Cited

FOREIGN PATENT DOCUMENTS

| WO | WO 2006/046035 A1 | 5/2006 |
| WO | WO 2006/046040 A1 | 5/2006 |

OTHER PUBLICATIONS

FDA mulls drug to slow late-stage Alzheimer's [online], [retrieved on Sep. 23, 2003]. Retrieved from the Internet, URL;http://www.cnn.com/2003/HEALTH/conditions/09/24/alzheimers.drug.ap/in-dex.html>.

Folkes et al., "The identification of 2-(1H-Indazol-4-yl)-6-(4-methanesulfonyl-piperazin-1-ylmethyl)-4-morpholin-4-yl-thieno[3,2-d]pyrimidine (GDC-0941) as a Potent, Selective, Orally Bioavailable Inhibitor of Class I PI3 Kinase for the Treatment of Cancer", *Journal of Medicinal Chemistry*, 51, 5522-5532 (2008).

Golub, T.R., et al., "Molecular Classification of Cancer: Class Discovery and Class Prediction by Gene Expression Monitoring", *Science*, 286, 531-537, (1999).

Hoeflich et al,"In vivo Antitumor Activity of MEK and Phosphatidylinositol 3-Kinase Inhibitors in Basal-Like Breast Cancer Models", *Clin. Cancer Res.*, 15, 4649-4664 (2009).

Huff, Joel R., "HIV Protease: A Novel Chemotherapeutic Target for AIDS," *Journal of Medicinal Chemistry*, vol. 34, No. 8, pp. 2305-2314, (1991).

International Search Report and Written Opinion of the International Searching Authority, PCT/GB2005/004129, Mar. 21, 2006.

Kang et al., "Phosphatidylinositol 3-kinase mutations identified in human cancer are oncogenic", *PNAS*, 102(3), 802-807, (2005).

Lala, P.K. and A. Orucevic, "Role of nitric oxide in tumor progression: Lessons from experimental tumors", *Cancer and Metastasis Reviews*, 17(1), 91-106, (1998).

Manhas et al., "Heterocyclic Compounds. V. 2, 4-Disubstituted Thienopyrimidones (1)", *Journal of Heterocyclic Chemistry*, 13, 633-638, (1976).

Raynaud et al., "Biological properties of potent inhibitors of class I phophatidylinositide 3-kinases: from PI-103 thru PI-540, PI-620 to the oral agent GDC-0941", *Mol. Cancer Ther.*, 8(7), 1725-1738, (2009).

Samuels et al., "High frequency of mutations of the PIK3CA gene in human cancers", *Science*, 304, 554, Apr. 23, 2004.

*Science*, vol. 286, 531-537, (1999).

Shayesteh et al., "PIK3CA is implicated as an oncogene in ovarian cancer", *Nature Genetics*, 21, 99-102, (1999).

Sos et al., "Identifying genotype-dependent efficacy of single and combined PI3K- and MAPK-pathway inhibition in cancer", *PNAS*, 106, 18351-18356 (2009).

Sutherlin et al., "Discovery of (Thienopyrimidin-2-yl) aminopyrimidines as Potent, Selective, and Orally Available Pan-PI3-Kinase and Dual Pan-PI3-Kinase/mTOR Inhibitors for the Treatment of Cancer", *Journal of Medicinal Chemistry*, 53, 1086-1097 (2010).

Workman et al., "Drugging the PI3 kinome", *Nature Biotechnology*, 24(7), 794-796, (2006).

Yap et al., "Targeting the PI3K-AKT-mTOR pathway: progress, pitfalls, and promises", *Current Opinion in Pharmacology*, 8, 393-412, (2008).

* cited by examiner

PHARMACEUTICAL COMPOUNDS

PRIORITY OF THE INVENTION

This application is a continuation of U.S. application Ser. No. 13/950,966, filed Jul. 25, 2013, which is a continuation of U.S. application Ser. No. 13/415,672, filed Mar. 8, 2012, which is now abandoned, which is a continuation of U.S. application Ser. No. 12/789,773, filed May 28, 2010, which is now U.S. Pat. No. 8,153,629 issued Apr. 10, 2012, which is a continuation of U.S. application Ser. No. 11/893,414, filed Aug. 16, 2007, which is now U.S. Pat. No. 7,750,002 issued Jul. 6, 2010, which is a continuation of PCT/GB2005/004129, filed Oct. 25, 2005, which claims priority from UK Application No. 0423653.5, filed Oct. 25, 2004, which applications are incorporated herein by reference.

FIELD OF THE INVENTION

The present invention relates to pyrimidine derivatives and their use as inhibitors of phosphatidylinositol 3-kinase (PI3K).

BACKGROUND TO THE INVENTION

Phosphatidylinositol (hereinafter abbreviated as "PI") is one of a number of phospholipids found in cell membranes. In recent years it has become clear that PI plays an important role in intracellular signal transduction. In the late 1980s, a PI3 kinase (PI3K) was found to be an enzyme which phosphorylates the 3-position of the inositol ring of phosphatidylinositol (D. Whitman et al, 1988, Nature, 332, 664).

PI3K was originally considered to be a single enzyme, but it has now been clarified that a plurality of subtypes are present in PI3K. Each subtype has its own mechanism for regulating activity. Three major classes of PI3Ks have been identified on the basis of their in vitro substrate specificity (B. Vanhaesebroeck, 1997, Trend in Biol. Sci, 22, 267). Substrates for class I PI3Ks are PI, PI 4-phosphate (PI4P) and PI 4,5-biphosphate (PI (4,5)P2). Class I PI3Ks are further divided into two groups, class Ia and class Ib, in terms of their activation mechanism. Class Ia PI3Ks include PI3K p110α, p110β and p110δ subtypes, which transmit signals from tyrosine kinase-coupled receptors. Class Ib PI3K includes a p110γ subtype activated by a G protein-coupled receptor. PI and PI(4)P are known as substrates for class II PI3Ks. Class II PI3Ks include PI3K C2α, C2β and C2γ subtypes, which are characterized by containing C2 domains at the C terminus. The substrate for class III PI3Ks is PI only.

In the PI3K subtypes, the class Ia subtype has been most extensively investigated to date. The three subtypes of class Ia are heterodimers of a catalytic 110 kDa subunit and regulatory subunits of 85 kDa or 55 kDa. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Thus, the class Ia subtypes are considered to be associated with cell proliferation and carcinogenesis.

WO 01/083456 describes a series of condensed heteroaryl derivatives which have activity as inhibitors of PI3K and which suppress cancer cell growth.

SUMMARY OF THE INVENTION

It has now been found that a novel class of fused pyrimidine compounds are effective inhibitors of PI3K with drug-like physicochemical and pharmacokinetic properties. The compounds exhibit selectivity for class Ia PI3Ks over class Ib, in particular for the P110α subtype.

Accordingly, the present invention provides a compound which is a fused pyrimidine of formula (I):

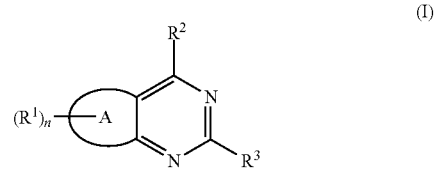

wherein
A represents a thiophene or furan ring;
n is 1 or 2;
$R^1$ is a group of formula:

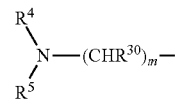

wherein
m is 0 or 1;
$R^{30}$ is H or $C_1$-$C_6$ alkyl;
$R^4$ and $R^5$ form, together with the N atom to which they are attached, a 5- or 6-membered saturated N-containing heterocyclic group which includes 0 or 1 additional heteroatoms selected from N, S and O, which may be fused to a benzene ring and which is unsubstituted or substituted; or one of $R^4$ and $R^5$ is alkyl and the other is a 5- or 6-membered saturated N-containing heterocyclic group as defined above or an alkyl group which is substituted by a 5- or 6-membered saturated N-containing heterocyclic group as defined above;
$R^2$ is selected from:

wherein $R^6$ and $R^7$ form, together with the nitrogen atom to which they are attached, a morpholine, thiomorpholine, piperidine, piperazine, oxazepane or thiazepane group which is unsubstituted or substituted; and

wherein Y is a $C_2$-$C_4$ alkylene chain which contains, between constituent carbon atoms of the chain and/or at one or both ends of the chain, 1 or 2 heteroatoms selected from O, N and S, and which is unsubstituted or substituted;
and $R^3$ is an indazole group which is unsubstituted or substituted;
or a pharmaceutically acceptable salt thereof.

DETAILED DESCRIPTION OF THE INVENTION

The thiophene or furan ring A in formula (I) adopts either of the two available regiochemical orientations. Formula (I) thus covers the thieno[3,2-d]pyrimidines and furano[3,2-d]pyrimidines of the following formula (Ia) as well as the thieno[2,3-d]pyrimidines and furano[2,3-d]pyrimidines of the following formula (Ib):

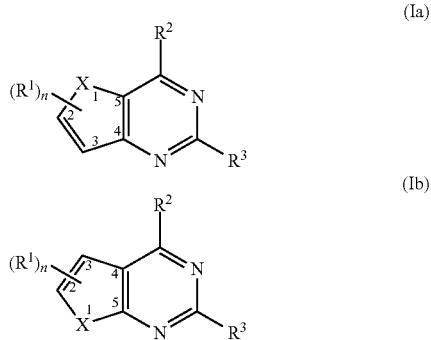

wherein each of $R^1$ to $R^3$ and n is as defined above and X is S or O.

In formula (I), the group or groups $R^1$, which are the same or different in a given compound when n is 2, may be bonded to either or both of the two available ring positions on the thiophene or furan ring A. Referring to structures (Ia) and (Ib) above, therefore, when n is 1 the furan or thiophene ring is mono-substituted by $R^1$ at the 2-position or the 3-position. When n is 2, the thiophene or furan ring is di-substituted by $R^1$ at positions 2 and 3.

As specified herein, an alkyl group is a straight or branched chain saturated hydrocarbon radical which is unsubstituted or substituted. Typically it is $C_1$-$C_{20}$ alkyl, for instance $C_1$-$C_{10}$ alkyl, such as $C_1$-$C_6$ alkyl or $C_1$-$C_4$ alkyl, for example methyl, ethyl, i-propyl, n-propyl, t-butyl, s-butyl or n-butyl. It may also be pentyl, hexyl, heptyl, octyl and the various branched chain isomers thereof.

When an alkyl group is substituted it typically bears one or more substituents $R^{20}$ selected from halogen, alkoxy, carbocyclyl, a 5- or 6-membered saturated N-containing heterocyclic group as defined above, OH, SR, CN, nitro, $NR_2$, —COOR, —C(O)R, —$CH_2$OR, $S(O)_mR$, —NRC(O)R, —$S(O)_mNR_2$, —OC(O)R, —$OC(O)NR_2$, —$NRS(O)_mR$, —$NRC(O)NR_2$ and —$CONR_2$, wherein each R is H, unsubstituted alkyl or $C_3$-$C_{10}$ cycloalkyl and m is 1 or 2.

Typically $R^{20}$ is selected from halogen, alkoxy, carbocyclyl, a 5- or 6-membered saturated N-containing heterocyclic group as defined above, OH, CN, $NR_2$, —COOR and —$CONR_2$, wherein each R is H or unsubstituted alkyl as defined above.

Substituted alkyl may be, for instance, a haloalkyl group or a group -alk-N($R^4$)($R^5$) wherein alk is an alkylene chain and $R^4$ and $R^5$ form, together with the N atom to which they are attached, a 5- or 6-membered saturated N-containing heterocyclic group which includes 0 or 1 additional heteroatoms selected from N, S and O, which may be fused to a benzene ring and which is unsubstituted or substituted. More typically it is a haloalkyl group or a group -alk-N($R^4$)($R^5$) wherein alk is an alkylene chain and $R^4$ and $R^5$ form, together with the N atom to which they are attached, a 5- or 6-membered saturated N-containing heterocyclic group as defined above.

An alkylene group is unsubstituted or substituted, straight or branched chain saturated divalent hydrocarbon group. Typically it is $C_1$-$C_8$ alkylene, for instance $C_1$-$C_6$ alkylene. Preferably it is $C_1$-$C_4$ alkylene, for example $C_2$-$C_4$ alkylene, such as methylene, ethylene, i-propylene, n-propylene, t-butylene, s-butylene or n-butylene. It may also be pentylene, hexylene, heptylene, octylene and the various branched chain isomers thereof. When the alkylene group is substituted it is typically substituted by a group $R^{20}$ as defined above or by alkyl which is unsubstituted or substituted by a group $R^{20}$ as defined above.

An alkenyl group is an unsubstituted or substituted, straight or branched chain hydrocarbon radical having one or more double bonds. Typically it is $C_2$-$C_8$ alkenyl, for instance $C_2$-$C_6$ alkenyl, such as allyl, butenyl, butadienyl, pentenyl or hexenyl. When the alkenyl group is substituted it is typically substituted by a group $R^{20}$ as defined above or by alkyl which is unsubstituted or substituted by a group $R^{20}$ as defined above.

An alkynyl group is an unsubstituted or substituted, straight or branched chain hydrocarbon radical having one or more triple bonds. Typically it is $C_2$-$C_8$ alkynyl, for instance $C_2$-$C_6$ alkynyl, such as ethynyl, propynyl or butynyl. When the alkynyl group is substituted it is typically substituted by a group $R^{20}$ as defined above or by alkyl which is unsubstituted or substituted by a group $R^{20}$ as defined above.

A haloalkyl group is an alkyl group as defined above, substituted by one or more halogen atoms. It can be a perhaloalkyl group, for instance trifluoromethyl or perfluorohexyl.

A halogen is chlorine, fluorine, bromine or iodine. It is typically bromine or iodine.

An alkoxy group is straight or branched chain. It is typically $C_1$-$C_6$ alkoxy, for instance $C_1$-$C_4$ alkoxy, such as methoxy, ethoxy, i-propoxy, n-propoxy, t-butoxy, n-butoxy or s-butoxy. It is unsubstituted or substituted, for instance by a group $R^{20}$ as defined above or by alkyl which is unsubstituted or substituted by a group $R^{20}$ as defined above. Typically it is substituted by carbocyclyl, morpholino, OH, CN, $NR_2$, —COOR or —$CONR_2$, wherein each R is H or unsubstituted alkyl as defined above.

A carbocyclyl group is a non-aromatic saturated or unsaturated monocyclic hydrocarbon ring, typically having from 3 to 10 carbon atoms. It may be a $C_3$-$C_8$ cycloalkyl group, or $C_5$-$C_{10}$ cycloalkyl group, for instance cyclopropyl, cyclobutyl, cyclopentyl, cyclohexyl, cycloheptyl or cyclooctyl. Alternatively it may be a cycloalkenyl group, typically $C_4$-$C_8$ cycloalkenyl, for instance cylcopentenyl, cyclohexenyl, cyclohexadienyl, cycloheptenyl, cyclohepadienyl, cyclooctenyl or cyclooctadienyl. A carbocyclyl group may be unsubstituted or, for instance by a group $R^{20}$ as defined above or by alkyl which is unsubstituted or substituted by a group $R^{20}$ as defined above. Typically it is substituted by alkoxy, morpholino, OH, CN, $NR_2$, —COOR or —$CONR_2$, wherein each R is H or unsubstituted alkyl as defined above.

A 5- or 6-membered saturated N-containing heterocyclic group which includes 0 or 1 additional heteroatoms selected from N, S and O, which may be fused to a benzene ring and which is unsubstituted or substituted is typically selected from morpholine, piperidine, piperazine, pyrrolidine, thiomorpholine, quinoline, isoquinoline, diazepane, oxazepane and thiazepane.

When a 5- or 6-membered saturated N-containing heterocyclic group as defined above is substituted it is typically substituted by one or more substituents, for instance 1, 2 or 3 substituents, typically by 1 or 2 substituents. Typically the substituents are selected from alkyl which is unsubstituted or substituted, alkoxy which is unsubstituted or substituted, —NR$_2$, —N(R''')-alk-OR, -alk-OR, —O-alk-OR, -alk-C(O) NR$_2$, —C(O)NR$_2$, -alk-Het, —N(R)-Het, —O-Het, —N(R)—C(O)-alk-OR, —C(O)—N(R)-alk-OR, -alk-S(O)$_2$R, —N(R)-alk-OR, -alk-NR'R", —N(R''')—S(O)$_2$R, S(O)$_2$R''', -alk-N(R)-alk-OR, —S(O)$_2$-alk-OR, a second 5- or 6-membered saturated N-containing heterocyclic group as defined above, a 5- or 6-membered N-containing heteroaryl group which is unsubstituted or substituted and which may be fused to a benzene ring, —COOR, —CONR$_2$, oxo (=O), —SO$_2$NR$_2$, —SO$_2$-alk-NR$_2$ and —CO-alk-OR, wherein: alk is an alkylene chain as defined above; Het is a 5- or 6-membered N-containing heteroaryl group as defined herein which is unsubstituted or substituted; R is H or alkyl, or when two groups R are bonded to N they may form, together with the N atom, a saturated 5- or 6-membered N-containing heterocyclic group as defined herein which is unsubstituted or substituted; each of R' and R" is independently H, alkyl or alkoxy; and R''' is alkyl which is unsubstituted or substituted, for instance by CF$_3$, NR$_2$, OR, a 5- or 6-membered saturated N-containing heterocyclic group as defined herein or a 5- or 6-membered N-containing heteroaryl group as defined herein, the said heterocyclic and heteroaryl groups being unsubstituted or substituted.

A 5-, 6- or 7-membered saturated heterocyclic group which contains 1 or 2 heteroatoms selected from N, S and O and which is unsubstituted or substituted is typically selected from tetrahydropyran, tetrahydrothiopyran, tetrahydrofuran and tetrahydrothiofuran.

When a 5-, 6- or 7-membered saturated heterocyclic group which contains 1 or 2 heteroatoms selected from N, S and O is substituted it may be substituted by a group $R^{20}$ as defined above. Typically it is substituted by one or more substituents selected from alkyl as defined above which is unsubstituted or substituted, for instance by $R^{20}$ as defined above or by alkyl which is unsubstituted or substituted by a group $R^{20}$ as defined above, haloalkyl as defined above, alkoxy as defined above which is unsubstituted or substituted, halogen, hydroxy, CN, nitro, amino, oxo (=O), and —NR'R" wherein each of R' and R" is independently H or alkyl.

A heteroaryl group is a heteroaryl group which contains 1, 2, 3 or 4 ring nitrogen atoms and 0, 1 or 2 additional heteroatoms selected from O, N and S, which group is monocyclic or bicyclic and which is unsubstituted or substituted. It is typically a 5- to 12-membered ring. Examples of a heteroaryl group include pyrrole, pyrazole, triazole, tetrazole, indazole, thiazole, isothiazole, oxazole, isooxazole, indole, isoindole, 1,3-dihydro-indol-2-one, pyridine-2-one, pyridine, pyridin-3-ol, imidazole, 1,3-dihydro-benzimidazolone, benzimidazole, benzothiazole, benzothiadiazole, quinoline, isoquinoline, quinoxaline, pyrazolopyridine, aminopyrazolinone, imidazopyridine, pyrimidine, pyridazine, pyrazine and isatin groups. Preferred examples include indazole, indole, pyrazole and tetrazole groups. These groups may be unsubstituted or substituted, for instance by a group $R^{20}$ as specified above or by alkyl which is unsubstituted or substituted by a group $R^{20}$ as defined above.

A 5- or 6-membered N containing heteroaryl group which may be fused to a benzene ring is typically selected from pyrrole, pyrazole, triazole, tetrazole, indazole, thiazole, isothiazole, oxazole, isooxazole, indole, isoindole, 1,3-dihydro-indol-2-one, pyridine-2-one, pyridine, pyridin-3-ol, imidazole, 1,3-dihydro-benzimidazolone, benzimidazole, benzothiazole, benzothiadiazole, quinoline, isoquinoline, quinoxaline, pyrazolopyridine, aminopyrazolinone, imidazopyridine, pyrimidine, pyridazine and pyrazine. When such a heteroaryl group is substituted it may be substituted by a group $R^{20}$ as defined above or by alkyl which is unsubstituted or substituted by a group $R^{20}$ as defined above.

In $R^1$, m is 0 or 1, typically 1. $R^{30}$ is typically H. $R^4$ and $R^5$ typically form, together with the N atom to which they are attached, a saturated N-containing heterocyclic group selected from morpholine, thiomorpholine, piperidine, piperazine, pyrrolidine, quinoline, isoquinoline, diazepane, oxazepane and thiazepane. The heterocylic group formed by $R^4$ and $R^5$ is unsubstituted or substituted, for instance by one or more substituents selected from alkyl which is unsubstituted or substituted, alkoxy which is unsubstituted or substituted, —N(R''')-alk-OR, -alk-OR, —O-alk-OR, -alk-C(O)NR$_2$, —C(O)NR$_2$, -alk-Het, —N(R)-Het, —O-Het, —N(R)—C(O)-alk-OR, —NR—S(O)$_2$R, —N(R)-alk-S(O)$_2$R, —N(R)-alk-OR, -alk-NR'R", —N(R''')—S(O)$_2$R, S(O)$_2$R''', -alk-N(R)-alk-OR, —S(O)$_2$-alk-OR and a 5- or 6-membered N-containing heteroaryl group which is unsubstituted or substituted and which may be fused to a benzene ring, —COOR, —CONR$_2$, oxo (=O), —SO$_2$NR$_2$, —SO$_2$-alk-NR$_2$ and —CO-alk-OR, wherein: alk is an alkylene chain as defined above; Het is a 5- or 6-membered N-containing heteroaryl group as defined herein which is unsubstituted or substituted; R is H or alkyl, or when two groups R are bonded to N they may form, together with the N atom, a saturated 5- or 6-membered N-containing heterocyclic group as defined herein which is unsubstituted or substituted; each of R' and R" is independently H, alkyl or alkoxy; and R''' is alkyl which is unsubstituted or substituted, for instance by CF$_3$, NR$_2$, OR, a 5- or 6-membered saturated N-containing heterocyclic group as defined herein or a 5- or 6-membered N-containing heteroaryl group as defined herein, the said heterocyclic and heteroaryl groups being unsubstituted or substituted.

In this definition of $R^1$ Het is typically selected from pyridine (for instance pyridin-1-yl, pyridin-2-yl or pyridin-3-yl), pyrimidine, imidazole, furan, oxazole, isoxazole and thiazole, each of which is unsubstituted or substituted. The moiety "alk" is typically a straight-chain $C_1$-$C_4$ alkylene group, more typically $C_1$-$C_3$ alkylene, such as —CH$_2$—, —CH$_2$CH$_2$, or —CH$_2$CH$_2$CH$_2$—.

In definition (a) of $R^2$ in formula (I), the ring formed by $R^6$ and $R^7$ is typically morpholine which is unsubstituted or substituted, for instance by a group $R^{20}$ as specified above. It may alternatively be a group selected from tetrahydropyran, tetrahydrothiopyran, tetrahydrofuran and tetrahydrothiofuran, each of which is unsubstituted or substituted, for instance, for instance by a group $R^{20}$ as specified above. When the ring formed by $R^6$ and $R^7$ is substituted it may be substituted on either a ring heteroatom or a ring carbon atom, for instance by a group $R^{20}$ as defined above or by alkyl which is unsubstituted or substituted by a group $R^{20}$ as defined above.

In definition (b) of $R^2$ in formula (I), the alkylene chain represented by Y forms, together with the carbon atoms to which it is attached, a saturated 5-, 6- or 7-membered heterocyclic ring which contains 1 or 2 heteroatoms selected from O, N and S and which is unsubstituted or substituted. Examples of the heterocyclic ring include tetrahydropyran, tetrahydrofuran, tetrahydrothiopyran, tetrahydrothiofuran and morpholine. When the heterocyclic ring is substituted it is typically substituted by one or more substituents, for instance 1, 2 or 3 substituents, selected from halogen, alkyl, haloalkyl (for instance trifluoromethyl), alkoxy, OH, CN, NR$_2$, oxo (=O), —COOR and —CONR$_2$, wherein each R is H or unsubstituted alkyl as defined above.

The indazole group in the definition of $R^3$ is unsubstituted or substituted. If it is substituted it may be substituted by one or more substituents selected from a group Z, wherein Z is selected from OR, CH₂OR, CO₂R, CF₂OH, CH(CF₃)OH, C(CF₃)₂OH, —(CH₂)$_q$OR and —(CH₂)$_q$NR₂ wherein each R is independently H or alkyl and q is 0, 1 or 2; one or more substituents selected from halo, alkyl, alkenyl, alkynyl, CN, NO₂, OR, SR, NR₂, C(O)R, SOR, SO₂R, SO₂NR₂, NC(O)R and CO₂R, wherein each R is independently H or alkyl; and an oxo group (=O). Typically, if substituted, the indazole group is substituted by OH, NH₂ or an oxo group. In one embodiment the indazole group is unsubstituted.

The indazole group R³ is an isostere of a 3-hydroxyphenyl or 4-hydroxyphenyl group. An isostere as used herein is a functional group which possesses binding properties which are the same as, or similar to, the 3-hydroxyphenyl or 4-hydroxyphenyl group in the context of the structure of formula (I).

In one embodiment the fused pyrimidine is of formula (Ic):

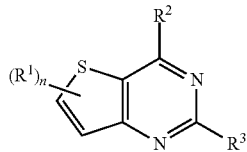

wherein
R² and R³ are as defined above;
n is 1; and
R¹ is a group of formula:

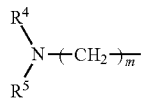

wherein
m is 0 or 1;
R⁴ and R⁵ form, together with the N atom to which they are attached, a 5- or 6-membered saturated N-containing heterocyclic group which includes 0 or 1 additional heteroatoms selected from N, S and O, and which is unsubstituted or substituted by one or more substituents selected from alkyl which is unsubstituted or substituted, alkoxy which is unsubstituted or substituted, —NR₂, —N(R''')-alk-OR, -alk-OR, —O-alk-OR, -alk-C(O)NR₂, —C(O)NR₂, -alk-Het, —N(R)-Het, —O-Het, —N(R)—C(O)-alk-OR, —C(O)—NR-alk-OR, -alk-S(O)₂R, —N(R)-alk-OR, -alk-NR'R'', —N(R''')—S(O)₂R, S(O)₂R''', -alk-N(R)-alk-OR, —S(O)₂-alk-OR, and a 5- or 6-membered N-containing heteroaryl group which is unsubstituted or substituted and which may be fused to a benzene ring, wherein alk is an alkylene chain as defined above, Het is a 5- or 6-membered N-containing heteroaryl group as defined herein which is unsubstituted or substituted, R is H or alkyl or when two groups R are bonded to N they may form, together with the N atom, a saturated 5- or 6-membered N-containing heterocyclic group as defined herein which is unsubstituted or substituted; each of R' and R'' is independently H, alkyl or alkoxy, and R''' is alkyl which is unsubstituted or substituted, or one of R⁴ and R⁵ is alkyl and the other is a 5- or 6-membered saturated N-containing heterocyclic group as defined above, which is unsubstituted or substituted as defined above, or an alkyl group which is substituted by a 5- or 6-membered saturated N-containing heterocyclic group as defined above;
or a pharmaceutically acceptable salt thereof.

In formula (Ic) the moiety "alk" is typically a straight-chain C₁-C₄ alkylene group, more typically C₁-C₃ alkylene, such as —CH₂—, —CH₂CH₂, or —CH₂CH₂CH₂—. The heterocyclic group formed by R⁴ and R⁵ is typically selected from morpholine, piperidine and piperazine, each of which is unsubstituted or substituted as defined above. R² is typically morpholine. R³ is typically an indazole group which is unsubstituted.

Specific examples of compounds of the invention include:
2-(1H-Indazol-4-yl)-6-(4-methyl-piperazin-1-ylmethyl)-4-morpholin-4-yl-thieno[3,2-d]pyrimidine;
4-[2-(1H-Indazol-4-yl)-4-morpholin-4-yl-thieno[3,2-d]pyrimidin-6-ylmethyl]-piperazine-1-sulfonic acid dimethylamide;
{4-[2-(1H-Indazol-4-yl)-4-morpholin-4-yl-thieno[3,2-d]pyrimidin-6-ylmethyl]-piperazin-1-yl}-morpholin-4-yl-methanone;
4-[2-(1H-Indazol-4-yl)-4-morpholin-4-yl-thieno[3,2-d]pyrimidin-6-ylmethyl]-piperazine-1-carboxylic acid (2-methoxy-ethyl)-methyl-amide;
{4-[2-(1H-Indazol-4-yl)-4-morpholin-4-yl-thieno[3,2-d]pyrimidin-6-ylmethyl]-piperazin-1-yl}-N,N-dimethyl-acetamide;
4-[2-(1H-Indazol-4-yl)-4-morpholin-4-yl-thieno[3,2-d]pyrimidin-6-ylmethyl]-piperazine-1-carboxylic acid dimethylamide;
2-(1H-Indazol-4-yl)-4-morpholin-4-yl-6-[4-(3-morpholin-4-yl-propane-1-sulfonyl)-piperazin-1-ylmethyl]-thieno[3,2-d]pyrimidine;
{1-[2-(1H-Indazol-4-yl)-4-morpholin-4-yl-thieno[3,2-d]pyrimidin-6-ylmethyl]-piperidin-4-yl}-(2-methoxy-ethyl)-methyl-amine;
(3-{4-[2-(1H-Indazol-4-yl)-4-morpholin-4-yl-thieno[3,2-d]pyrimidin-6-ylmethyl]-piperazine-1-sulfonyl}-propyl)-dimethyl-amine;
2-{4-[2-(1H-Indazol-4-yl)-4-morpholin-4-yl-thieno[3,2-d]pyrimidin-6-ylmethyl]-piperazin-1-yl}-2-methyl-propan-1-ol;
1'-[2-(1H-Indazol-4-yl)-4-morpholin-4-yl-thieno[3,2-d]pyrimidin-6-ylmethyl]-[1,4']bipiperidinyl;
2-(1H-Indazol-4-yl)-4-morpholin-4-yl-6-(4-morpholin-4-yl-piperidin-1-ylmethyl)-thieno[3,2-d]pyrimidine;
2-(1H-Indazol-4-yl)-4-morpholin-4-yl-6-(4-pyrimidin-2-yl-piperazin-1-ylmethyl)-thieno[3,2-d]pyrimidine;
1-(2-Hydroxy-ethyl)-4-[2-(1H-indazol-4-yl)-4-morpholin-4-yl-thieno[3,2-d]pyrimidin-6-ylmethyl]-piperazin-2-one;
6-(4-Cyclopropylmethyl-piperazin-1-ylmethyl)-2-(1H-indazol-4-yl)-4-morpholin-4-yl-thieno[3,2-d]pyrimidine;
2-(1H-Indazol-4-yl)-4-morpholin-4-yl-6-(4-pyridin-2-yl-piperazin-1-ylmethyl)-thieno[3,2-d]pyrimidine;
2-(1H-Indazol-4-yl)-4-morpholin-4-yl-6-[4-(2,2,2-trifluoro-ethyl)-piperazin-1-ylmethyl]-thieno[3,2-d]pyrimidine;
2-(1H-Indazol-4-yl)-4-morpholin-4-yl-6-(4-thiazol-2-yl-piperazin-1-ylmethyl)-thieno[3,2-d]pyrimidine;
2-(6-Fluoro-1H-indazol-4-yl)-6-(4-methyl-piperazin-1-ylmethyl)-4-morpholin-4-yl-thieno[3,2-d]pyrimidine;
2-(1H-Indazol-4-yl)-4-morpholin-4-yl-6-(4-pyridin-2-ylmethyl-piperazin-1-ylmethyl)-thieno[3,2-d]pyrimidine;
2-(1H-Indazol-4-yl)-4-morpholin-4-yl-6-(4-thiazol-2-ylmethyl-piperazin-1-ylmethyl)-thieno[3,2-d]pyrimidine;
2-(1H-Indazol-4-yl)-6-[4-(5-methyl-furan-2-ylmethyl)-piperazin-1-ylmethyl]-4-morpholin-4-yl-thieno[3,2-d]pyrimidine;
1-[2-(1H-Indazol-4-yl)-4-morpholin-4-yl-thieno[3,2-d]pyrimidin-6-ylmethyl]-piperidine-4-carboxylic acid amide;

2-(1H-Indazol-4-yl)-6-[4-(2-methoxy-1,1-dimethyl-ethyl)-piperazin-1-ylmethyl]-4-morpholin-4-yl-thieno[3,2-d]pyrimidine;

2-(1H-Indazol-4-yl)-6-[(3R,5S)-4-(2-methoxy-ethyl)-3,5-dimethyl-piperazin-1-ylmethyl]-4-morpholin-4-yl-thieno[3,2-d]pyrimidine;

1-[2-(1H-Indazol-4-yl)-4-morpholin-4-yl-thieno[3,2-d]pyrimidin-6-ylmethyl]-piperidine-4-carboxylic acid (2-methoxy-ethyl)-methyl-amide;

1-[2-(1H-Indazol-4-yl)-4-morpholin-4-yl-thieno[3,2-d]pyrimidin-6-ylmethyl]-piperidine-4-carboxylic acid dimethylamide;

2-(1H-Indazol-4-yl)-4-morpholin-4-yl-6-(4-pyridin-3-ylmethyl-piperazin-1-ylmethyl)-thieno[3,2-d]pyrimidine;

1-[2-(1H-Indazol-4-yl)-4-morpholin-4-yl-thieno[3,2-d]pyrimidin-6-ylmethyl]-piperidine-4-carboxylic acid methylamide;

2-{4-[2-(1H-Indazol-4-yl)-4-morpholin-4-yl-thieno[3,2-d]pyrimidin-6-ylmethyl]-piperazin-1-yl}-N-methyl-isobutyramide;

2-{4-[2-(1H-Indazol-4-yl)-4-morpholin-4-yl-thieno[3,2-d]pyrimidin-6-ylmethyl]-piperazin-1-yl}-2-methyl-1-pyrrolidin-1-yl-propan-1-one;

2-(1H-Indazol-4-yl)-6-[4-(1-methyl-1H-imidazol-2-ylmethyl)-piperazin-1-ylmethyl]-4-morpholin-4-yl-thieno[3,2-d]pyrimidine;

2-(1H-Indazol-4-yl)-6-[4-(5-methyl-isoxazol-3-ylmethyl)-piperazin-1-ylmethyl]-4-morpholin-4-yl-thieno[3,2-d]pyrimidine;

1-{4-[2-(1H-Indazol-4-yl)-4-morpholin-4-yl-thieno[3,2-d]pyrimidin-6-ylmethyl]-piperazin-1-yl}-2-methyl-propan-2-ol;

Cyclopropylmethyl-{1-[2-(1H-indazol-4-yl)-4-morpholin-4-yl-thieno[3,2-d]pyrimidin-6-ylmethyl-piperidin-4-yl}-(2-methoxy-ethyl)-amine;

6-[4-(1-Ethyl-1-methoxymethyl-propyl)-piperazin-1-ylmethyl]-2-(1H-indazol-4-yl)-4-morpholin-4-yl-thieno[3,2-d]pyrimidine;

2-(1H-Indazol-4-yl)-6-[4-(1-methoxymethyl-cyclopropyl)-piperazin-1-ylmethyl]-4-morpholin-4-yl-thieno[3,2-d]pyrimidine;

{1-[2-(1H-Indazol-4-yl)-4-morpholin-4-yl-thieno[3,2-d]pyrimidin-6-ylmethyl]-piperidin-4-yl}-(2-methoxy-ethyl)-(2,2,2-trifluoro-ethyl)-amine;

2-(1H-Indazol-4-yl)-6-[4-(2-methoxy-ethyl)-piperazin-1-ylmethyl]-4-morpholin-4-yl-thieno[3,2-d]pyrimidine;

{1-[2-(1H-Indazol-4-yl)-4-morpholin-4-yl-thieno[3,2-d]pyrimidin-6-ylmethyl]-piperidin-4-yl}-methanol;

2-(1H-Indazol-4-yl)-4-morpholin-4-yl-6-(4-pyridin-4-ylmethyl-piperazin-1-ylmethyl)-thieno[3,2-d]pyrimidine;

2-(1H-Indazol-4-yl)-6-[4-(6-methyl-pyridin-2-ylmethyl)-piperazin-1-ylmethyl]-4-morpholin-4-yl-thieno[3,2-d]pyrimidine;

2-(1H-Indazol-4-yl)-6-[4-(4-methyl-thiazol-2-ylmethyl)-piperazin-1-ylmethyl]-4-morpholin-4-yl-thieno[3,2-d]pyrimidine;

{1-[2-(1H-Indazol-4-yl)-4-morpholin-4-yl-thieno[3,2-d]pyrimidin-6-ylmethyl]-piperidin-4-yl}-pyridin-2-yl-amine;

N-{1-[2-(1H-Indazol-4-yl)-4-morpholin-4-yl-thieno[3,2-d]pyrimidin-6-ylmethyl]-piperidin-4-yl}-2-methoxy-N-methyl-acetamide;

N-{1-[2-(1H-Indazol-4-yl)-4-morpholin-4-yl-thieno[3,2-d]pyrimidin-6-ylmethyl]-piperidin-4-yl}-N-methyl-methanesulfonamide;

{1-[2-(1H-Indazol-4-yl)-4-morpholin-4-yl-thieno[3,2-d]pyrimidin-6-ylmethyl]-piperidin-4-yl}-(3-methoxy-propyl)-methyl-amine;

6-((3S,5R)-3,5-Dimethyl-4-pyridin-2-ylmethyl-piperazin-1-ylmethyl)-2-(1H-indazol-4-yl)-4-morpholin-4-yl-thieno[3,2-d]pyrimidine;

2-(1H-Indazol-4-yl)-6-(4-methoxymethyl-piperidin-1-ylmethyl)-4-morpholin-4-yl-thieno[3,2-d]pyrimidine;

{1-[2-(1H-Indazol-4-yl)-4-morpholin-4-yl-thieno[3,2-d]pyrimidin-6-ylmethyl]-piperidin-4-yl}-(2-methoxy-ethyl)-thiazol-2-ylmethyl-amine;

1-[2-(1H-Indazol-4-yl)-4-morpholin-4-yl-thieno[3,2-d]pyrimidin-6-ylmethyl]-4-pyridin-2-ylmethyl-piperidin-4-ol;

{1-[2-(1H-Indazol-4-yl)-4-morpholin-4-yl-thieno[3,2-d]pyrimidin-6-ylmethyl]-piperidin-4-yl}-isopropyl-(2-methoxy-ethyl)-amine;

2-(1H-Indazol-4-yl)-4-morpholin-4-yl-6-[4-(pyridin-2-yloxy)-piperidin-1-ylmethyl]-thieno[3,2-d]pyrimidine;

N-{1-[2-(1H-Indazol-4-yl)-4-morpholin-4-yl-thieno[3,2-d]pyrimidin-6-ylmethyl]-piperidin-4-yl}-N-(2-methoxy-ethyl)-methanesulfonamide;

2-{1-[2-(1H-Indazol-4-yl)-4-morpholin-4-yl-thieno[3,2-d]pyrimidin-6-ylmethyl]-piperidin-4-yl}-propan-2-ol;

2-(1H-Indazol-4-yl)-4-morpholin-4-yl-6-[4-(1-oxy-pyridin-3-ylmethyl)-piperazin-1-ylmethyl]-thieno[3,2-d]pyrimidine;

2-(1H-Indazol-4-yl)-4-morpholin-4-yl-6-(4-morpholin-4-ylmethyl-piperidin-1-ylmethyl)-thieno[3,2-d]pyrimidine;

{1-[2-(1H-Indazol-4-yl)-4-morpholin-4-yl-thieno[3,2-d]pyrimidin-6-ylmethyl]-piperidin-4-ylmethyl}-(2-methoxy-ethyl)-methyl-amine;

{1-[2-(1H-Indazol-4-yl)-4-morpholin-4-yl-thieno[3,2-d]pyrimidin-6-ylmethyl]-piperidin-4-ylmethyl}-dimethyl-amine;

{1-[2-(1H-Indazol-4-yl)-4-morpholin-4-yl-thieno[3,2-d]pyrimidin-6-ylmethyl]-piperidin-3-yl}-(2-methoxy-ethyl)-methyl-amine;

1-[2-(1H-Indazol-4-yl)-4-morpholin-4-yl-thieno[3,2-d]pyrimidin-6-ylmethyl]-piperidine-3-carboxylic acid methylamide;

2-(1H-Indazol-4-yl)-6-(3-methoxymethyl-piperidin-1-ylmethyl)-4-morpholin-4-yl-thieno[3,2-d]pyrimidine;

2-(1H-Indazol-4-yl)-4-morpholin-4-yl-6-(4-pyridin-2-ylmethyl-piperidin-1-ylmethyl)-thieno[3,2-d]pyrimidine;

2-(1H-Indazol-4-yl)-6-[1,4-(2-methoxy-ethoxy)-piperidin-1-ylmethyl]-4-morpholin-4-yl-thieno[3,2-d]pyrimidine;

6-((3R,5S)-3,5-Dimethyl-4-thiazol-2-ylmethyl-piperazin-1-ylmethyl)-2-(1H-indazol-4-yl)-4-morpholin-4-yl-thieno[3,2-d]pyrimidine;

2-(1H-Indazol-4-yl)-4-morpholin-4-yl-6-[4-(1-oxy-pyridin-2-ylmethyl)-piperazin-1-ylmethyl]-thieno[3,2-d]pyrimidine;

2-(1H-Indazol-4-yl)-6-[4-(2-methoxy-ethyl)-piperidin-1-ylmethyl]-4-morpholin-4-yl-thieno[3,2-d]pyrimidine;

2-(1H-Indazol-4-yl)-6-(4-methanesulfonyl-piperidin-1-ylmethyl)-4-morpholin-4-yl-thieno[3,2-d]pyrimidine;

{1-[2-(1H-Indazol-4-yl)-4-morpholin-4-yl-thieno[3,2-d]pyrimidin-6-ylmethyl]-piperidin-4-yl}-(3-methanesulfonyl-propyl)-methyl-amine;

2-(1H-Indazol-4-yl)-6-[4-(3-methoxy-propane-1-sulfonyl)-piperidin-1-ylmethyl]-4-morpholin-4-yl-thieno[3,2-d]pyrimidine.

(R)-1-[2-(1H-Indazol-4-yl)-4-morpholin-4-yl-thieno[3,2-d]pyrimidin-6-ylmethyl]-piperidine-3-carboxylic acid methylamide;

(S)-1-[2-(1H-Indazol-4-yl)-4-morpholin-4-yl-thieno[3,2-d]pyrimidin-6-ylmethyl]-piperidine-3-carboxylic acid methylamide;

6-(4-Imidazol-1-ylmethyl-piperidin-1-ylmethyl)-2-(1H-indazol-4-yl)-4-morpholin-4-yl-thieno[3,2-d]pyrimidine;

2-(1H-Indazol-4-yl)-4-morpholin-4-yl-6-morpholin-4-ylm-
ethyl-thieno[3,2-d]pyrimidine;
2-(1H-Indazol-4-yl)-6-(3-methyl-piperidin-1-ylmethyl)-4-
morpholin-4-yl-thieno[3,2-d]pyrimidine;
{1-[2-(1H-Indazol-4-yl)-4-morpholin-4-yl-thieno[3,2-d]py-
rimidin-6-ylmethyl]-piperidin-3-yl}-methanol;
2-{1-[2-(1H-Indazol-4-yl)-4-morpholin-4-yl-thieno[3,2-d]
pyrimidin-6-ylmethyl]-piperidin-4-yl}-ethanol;
1-[2-(1H-Indazol-4-yl)-4-morpholin-4-yl-thieno[3,2-d]pyri-
midin-6-ylmethyl]-4-thiazol-2-yl-piperidin-4-ol;
2-(1-Methyl-1H-indazol-4-yl)-6-(4-methyl-piperazin-1-yl-
methyl)-4-morpholin-4-yl-thieno[3,2-d]pyrimidine;
2-(2-Methyl-2H-indazol-4-yl)-6-(4-methyl-piperazin-1-yl-
methyl)-4-morpholin-4-yl-thieno[3,2-d]pyrimidine;
2-(1H-Indazol-4-yl)-4-morpholin-4-yl-6-(4-thiazol-4-ylm-
ethyl-piperazin-1-ylmethyl)-thieno[3,2-d]pyrimidine;
1-{4-[2-(1H-Indazol-4-yl)-4-morpholin-4-yl-thieno[3,2-d]
pyrimidin-6-ylmethyl]-piperazin-1-yl}-3-phenoxy-pro-
pan-2-ol;
6-[4-(1H-Imidazol-2-ylmethyl)-piperazin-1-ylmethyl]-2-
(1H-indazol-4-yl)-4-morpholin-4-yl-thieno[3,2-d]pyrimi-
dine;
6-[4-(3H-Imidazol-4-ylmethyl)-piperazin-1-ylmethyl]-2-
(1H-indazol-4-yl)-4-morpholin-4-yl-thieno[3,2-d]pyrimi-
dine;
2-(1H-Indazol-4-yl)-4-morpholin-4-yl-6-((2S,6R)-2,4,6-tri-
methyl-piperazin-1-ylmethyl)-thieno[3,2-d]pyrimidine;
{4-[2-(1H-Indazol-4-yl)-4-morpholin-4-yl-thieno[3,2-d]py-
rimidin-6-ylmethyl]-1-methanesulfonyl-piperazin-2-yl}-
methanol; and
2-(1H-Indazol-4-yl)-6-(4-methanesulfonyl-3-methoxym-
ethyl-piperazin-1-ylmethyl)-4-morpholin-4-yl-thieno[3,
2-d]pyrimidine;
and the pharmaceutically acceptable salts thereof.

The compounds of formula (I) may exist in the form of geometrical isomers or tautomers depending on the kinds of substituent groups, and these isomers in separated forms or mixtures thereof may be used in the present invention. Where the compounds have asymmetric carbon atoms, optical isomer forms may exist based on such carbon atoms. All of the mixtures and the isolated forms of these optical isomers may be used in the present invention.

A suitable synthetic strategy for producing compounds of formula (I) in which m is 1 employs the precursor carboxaldehyde of formula (II):

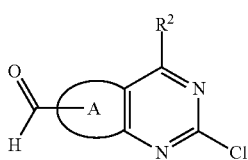

(II)

wherein A and $R^2$ are as defined above. Starting from this precursor the synthesis comprises performing, in either order, a palladium-mediated (Suzuki-type) cross-coupling reaction and a reductive amination. The present invention therefore further provides a process for producing a compound of formula (I) as defined above in which m is 1, which process comprises:

(a) treating a compound of formula (II):

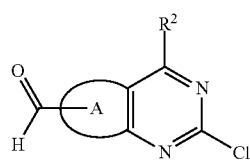

(II)

wherein A and $R^2$ are as defined above, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst; and treating the resulting compound of formula (III):

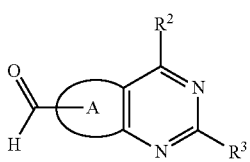

(III)

wherein A, $R^2$ and $R^3$ are as defined above, with an amine of formula $NHR^4R^5$ in which $R^4$ and $R^5$ are as defined above, in the presence of a suitable reducing agent; or (b) treating a compound of formula (II) as defined above with an amine of formula $NHR^4R^5$ wherein $R^4$ and $R^5$ are as defined above, in the presence of a suitable reducing agent; and treating the resulting compound of formula (IV):

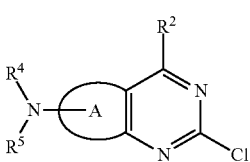

(IV)

wherein A, $R^2$, $R^4$ and $R^5$ are as defined above, with a boronic acid or ester thereof of formula $R^3B(OR^{15})_2$, in which $R^3$ is as defined above and each $R^{15}$ is H or $C_1$-$C_6$ alkyl or the two groups $OR^{15}$ form, together with the boron atom to which they are attached, a pinacolato boronate ester group, in the presence of a Pd catalyst.

Both the amination step and the Pd-mediated cross-coupling step take place under conventional conditions. The palladium catalyst may be any that is typically used for Suzuki-type cross-couplings, such as $PdCl_2(PPh_3)_2$. The reducing agent is typically a borohydride, for instance $NaBH(OAc)_3$, $NaBH_4$ or $NaCNBH_4$, in particular $NaBH(OAc)_3$.

The pinacolato boronate ester may be, for instance, prepared as described in either of Reference Examples 5 and 6 which follow.

A compound of formula (II) as defined above wherein $R^2$ is $-NR^6R^7$ may be prepared by a process which comprises treating a compound of formula (IX):

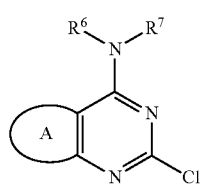

(IX)

wherein A, R⁶ and R⁷ are as defined above, with a lithiating agent followed by N,N'-dimethylformamide (DMF). The reaction is typically conducted by adding a solution of the lithiating agent in a non-polar organic solvent, for instance a hydrocarbon solvent such as hexane, to a suspension of the compound of formula (IX) in an organic solvent such as tetrahydrofuran (THF). If THF is used the addition takes place at a low temperature, of about −78° C. The lithiating agent is typically an alkyllithium, for instance n-butyllithium.

A compound of formula (IX) as defined above may be produced by a process which comprises treating a compound of formula (X):

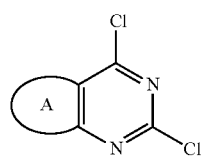

(X)

with an amine of formula NHR⁶R⁷, wherein R⁶ and R⁷ are as defined above, in an organic solvent. The solvent is typically an alcohol, such as methanol. The reaction is generally conducted at room temperature.

A compound of formula (X) may be prepared by the process described in Reference Example 1 for the preparation of 2,4-dichloro-thieno[3,2-d]pyrimidine, or by analogy with such a process.

A compound of formula (II) as defined above wherein R² is of formula

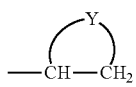

may be prepared by a process which comprises submitting a compound of formula (XI):

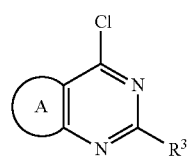

(XI)

wherein A and R³ are as defined above, to palladium-mediated cross-coupling with a compound of formula (XII):

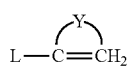

(XII)

wherein L is H or a group selected from halo, —OSO₂CF₃, —B(OR)₂, —Sn(R)₃ and —Si(R)₃ wherein R is H or alkyl as defined above, followed by reduction, to yield a compound of the following formula (XIII):

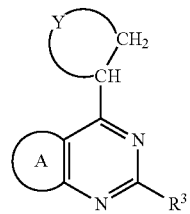

(XIII)

wherein A, R³ and Y are as defined above.

The compound of formula (XIII) may be converted to the corresponding carboxaldehyde by treatment with a lithiating agent followed by N,N'-dimethylformamide (DMF), for instance under the conditions described above for the conversion of a compound of formula (IX) to a compound of formula (II). The lithiating agent is typically as defined above. The resulting carboxaldehyde may then be converted into a desired final compound of formula (I) as defined above, in which m is 1, by treatment with an amine of formula NHR⁴R⁵ in which R⁴ and R⁵ are as defined above, in the presence of a suitable reducing agent, for instance a borohydride as specified above, in particular NaBH(OAc)₃.

A compound of formula (I) as defined above in which m is 0 may be prepared by a Buchwald-type palladium-mediated nitrogen insertion reaction. Such a process may comprise treating a compound of formula (XIV):

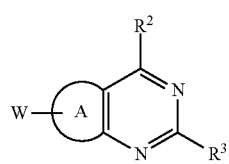

(XIV)

wherein A, R² and R³ are as defined above and W is a halo group selected from Br and I, with an amine of formula NHR⁴R⁵ in which R⁴ and R⁵ are as defined above, in the presence of a palladium catalyst.

A compound of formula (XIV) may be produced by treating a compound of formula (XV):

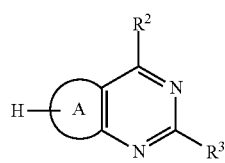

(XV)

wherein A, R² and R³ are as defined above, with a lithiating agent and a halogen selected from bromine and iodine. The lithiating agent is typically an alkyllithium, for instance butyllithium. The halogen is typically iodine, which gives rise to a compound of formula (XIV) in which W is I.

A compound of formula (I) as defined above in which m is 0 may also be prepared by an SNAr displacement reaction, for instance under the conditions described by D. Prim and G. Kirsch in *Tetrahedron* 1999, 55 (21), 6511-6526. Such a process comprises treating a compound of formula (XIV) as defined above in which W is Br with an amine of formula $NHR^4R^5$ in which $R^4$ and $R^5$ are as defined above in $H_2O$ under reflux for 12 h.

A compound of formula (I) as defined above in which m is 0 may alternatively be prepared by treating a compound of formula (XIV) as defined above in which W is I with an amine of formula $NHR^4R^5$ in which $R^4$ and $R^5$ are as defined above in 1,4-dioxane in the presence of CuI/En and $K_3PO_4$. The reaction is conducted at about 110° C. for 24 h. This procedure is described by Kang S-K et al in Synlett, (3), 427-430, 2002.

A fused pyrimidine of formula (I) may be converted into a pharmaceutically acceptable salt, and a salts may be converted into the free compound, by conventional methods. Examples of pharmaceutically acceptable salts include acid addition salts with inorganic acids such as hydrochloric acid, hydrobromic acid, hydroiodic acid, sulphuric acid, nitric acid and phosphoric acid; and organic acids such as formic acid, acetic acid, trifluoroacetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid and glutamic acid. In the case of compounds of the invention bearing a free carboxy substituent, the salts include the salts of alkali and alkaline earth metals and ammonium, for instance the salts of sodium, potassium, magnesium, calcium and ammonium. The latter are prepared by treating the free fused pyrimidine of formula (I), or an acid addition salt thereof, with the corresponding metal base or ammonia. The compounds of formula (I) and their salts may exist as hydrates or solvates.

Compound of the present invention have been found in biological tests to be inhibitors of PI3 kinase. The compounds are selective for class Ia PI3 kinases over class Ib and typically exhibit at least a 20-fold selectivity for class Ia over class Ib PI3 kinases. In particular, the compounds are selective for the p110α isoform.

A compound of the present invention may thus be used as an inhibitor of PI3 kinase, in particular of a class Ia PI3 kinase. Accordingly, a compound of the present invention can be used to treat a disease or disorder arising from abnormal cell growth, function or behaviour associated with PI3 kinase. Examples of such diseases and disorders are discussed by Drees et al in Expert Opin. Ther. Patents (2004) 14(5):703-732. These include cancer, immune disorders, cardiovascular disease, viral infection, inflammation, metabolism/endocrine disorders and neurological disorders. Examples of metabolism/endocrine disorders include diabetes and obesity. Examples of cancers which the present compounds can be used to treat include leukaemia, brain tumours, renal cancer, gastric cancer and cancer of the skin, bladder, breast, uterus, lung, colon, prostate, ovary and pancreas. A human or animal patient suffering from an immune disorder, cancer, cardiovascular disease, viral infection, inflammation, a metabolism/endocrine disorder or a neurological disorders may thus be treated by a method comprising the administration thereto of a compound of the present invention as defined above. The condition of the patient may thereby be improved or ameliorated.

In addition to possessing biochemical potency the compounds of the invention exhibit physicochemical and pharmacokinetic properties which make them particularly well adapted for drug use. This is shown for instance in the results of the biological assays described in Example 3, which follows. In particular the compounds possess high aqueous solubility at physiological pH; many have a solubility of at least 40 μM and a significant number have a solubility of greater than 100 μM. High solubility at physiological pH is desirable since it promotes bioavailability. The compounds also possess high metabolic stability, as shown in particular by the hepatocyte clearance assay described in Example 3 in which most of the tested compounds were shown to have low hepatocyte clearance. Low hepatocyte clearance correlates with a low rate of liver metabolism. It can therefore be seen that the compounds of the present invention possess improved physicochemical and pharmacokinetic properties whilst retaining biochemical potency as inhibitors of PI3 kinase.

A compound of the present invention can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection or infusion.

The dosage depends on a variety of factors including the age, weight and condition of the patient and the route of administration. Daily dosages can vary within wide limits and will be adjusted to the individual requirements in each particular case. Typically, however, the dosage adopted for each route of administration when a compound is administered alone to adult humans is 0.0001 to 50 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

A compound is formulated for use as a pharmaceutical or veterinary composition also comprising a pharmaceutically or veterinarily acceptable carrier or diluent. The compositions are typically prepared following conventional methods and are administered in a pharmaceutically or veterinarily suitable form. The compound may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents;

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

C) By inhalation, in the form of aerosols or solutions for nebulizers;

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols;

E) Topically, in the form of creams, ointments, jellies, collyriums, solutions or suspesions.

The invention will be further described in the Examples which follow:

REFERENCE EXAMPLE 1

2,4-Dichloro-thieno[3,2-d]pyrimidine (64)

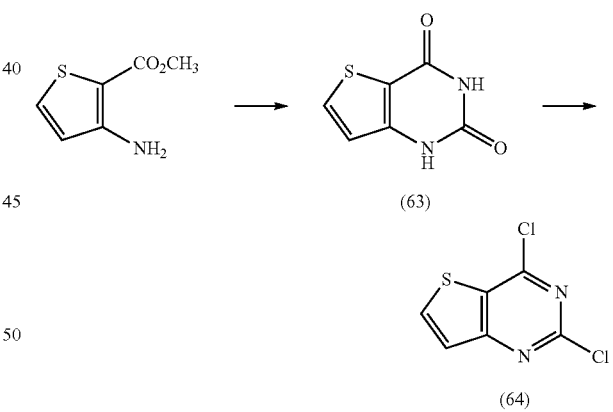

A mixture of methyl 3-amino-2-thiophenecarboxylate (13.48 g, 85.85 mmol) and urea (29.75 g, 5 eq.) was heated at 190° C. for 2 h. The hot reaction mixture was then poured onto sodium hydroxide solution and any insoluble material removed by filtration. The mixture was then acidified (HCl, 2N) to yield 1H-thieno[3,2-d]pyrimidine-2,4-dione (63) as a white precipitate, which was collected by filtration and air dried (9.49 g, 66%).

$^1$H NMR (400 MHz, d$_6$-DMSO) 6.90 (1H, d, J=5.2 Hz), 8.10 (1H, d, J=5.2 Hz), 11.60-11.10 (2H, br s).

A mixture of 1H-thieno[3,2-d]pyrimidine-2,4-dione (9.49 g, 56.49 mmol) and phosphorous oxychloride (150 mL) was heated at reflux for 6 h. The reaction mixture was then cooled and poured onto ice/water with vigorous stirring yielding a precipitate. The mixture was then filtered to yield 2,4-dichloro-thieno[3,2-d]pyrimidine (64) as a white solid (8.68 g, 75%)

$^1$H NMR (400 MHz, CDCl$_3$) 7.56 (1H, d, J=5.5 Hz), 8.13 (1H, d, J=5.5 Hz).

REFERENCE EXAMPLE 2

2-Chloro-4-morpholin-4-yl-thieno[3,2-d]pyrimidine (65)

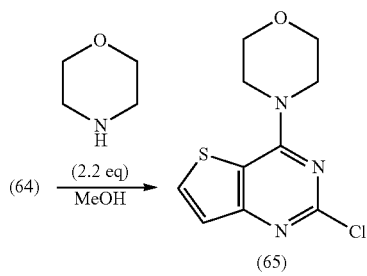 [SMILES: "MeOH" ; C1COCCN1 ; Clc1nc(N2CCOCC2)c2sccc2n1]

A mixture of 2,4-dichloro-thieno[3,2-d]pyrimidine (64), (8.68 g, 42.34 mmol), morpholine (8.11 mL, 2.2 eq.) and MeOH (150 mL) was stirred at room temperature for 1 h. The reaction mixture was then filtered, washed with water and MeOH, to yield the title compound as a white solid (11.04 g, 100%).

$^1$H NMR (400 MHz, d$_6$-DMSO) 3.74 (4H, t, J=4.9 Hz), 3.90 (4H, t, J=4.9 Hz), 7.40 (1H, d, J=5.6 Hz), 8.30 (1H, d, J=5.6 Hz).

REFERENCE EXAMPLE 3

2-Chloro-4-morpholin-4-yl-thieno[3,2-d]pyrimidine-6-carbaldehyde (66)

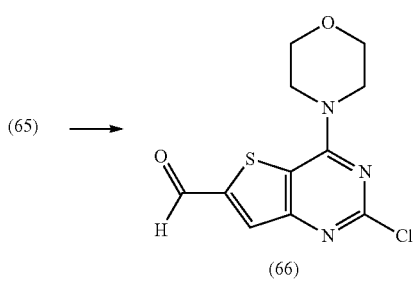 [SMILES: O=Cc1cc2nc(Cl)nc(N3CCOCC3)c2s1]

To a suspension of 2-chloro-4-morpholin-4-yl-thieno[3,2-d]pyrimidine (65) (1.75 g, 6.85 mmol) in dry THF (40 mL) at −78° C. was added a 2.5M solution of nBuLi in hexane (3.3 mL, 1.2 eq.). After stirring for 1 h, dry DMF (796 μL, 1.5 eq.) was added. The reaction mixture was stirred for 1 h at −78° C. and then warmed slowly to room temperature. After a further 2 h at room temperature the reaction mixture poured onto ice/water yielding a yellow precipitate. This was collected by filtration and air-dried to yield the title compound (1.50 g, 77%)

$^1$H NMR (400 MHz, d$_6$-DMSO) 3.76 (4H, t, J=4.9), 3.95 (4H, t, J=4.9), 8.28 (1H, s), 10.20 (1H, s),

REFERENCE EXAMPLE 4

2-Chloro-6-(4-methyl-piperazin-1-ylmethyl)-4-morpholin-4-yl-thieno[3,2-d]pyrimidine (72)

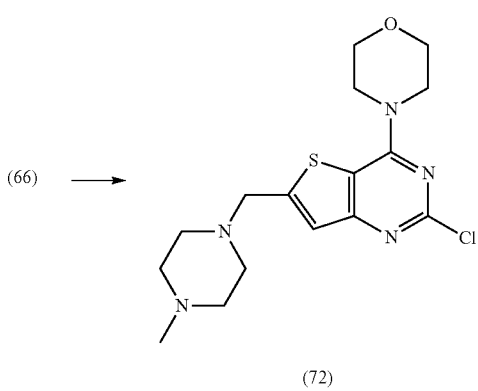 [SMILES: CN1CCN(Cc2cc3nc(Cl)nc(N4CCOCC4)c3s2)CC1]

To a mixture of 2-chloro-4-morpholin-4-yl-thieno[3,2-d]pyrimidine-6-carbaldehyde (66) (147 mg, 0.52 mmol), 1-methyl-piperazine (1.5 eq., 87 μL) and acetic acid (1.05 eq., 32 μL) in 1,2-dichloroethane (3 mL) was added sodium triacetoxyborohydride (1.1 eq., 121 mg) and then stirred at room temperature overnight. The reaction mixture was diluted with DCM, washed with a saturated solution of sodium hydrogen carbonate, brine, separated and dried (MgSO$_4$). The crude product was evaporated in vacuo and purified by chromatography to give the title compound 72 as an off-white crystalline solid (51 mg, 45%).

REFERENCE EXAMPLE 5

Indazole-4-Boronate Ester (70): Route 1

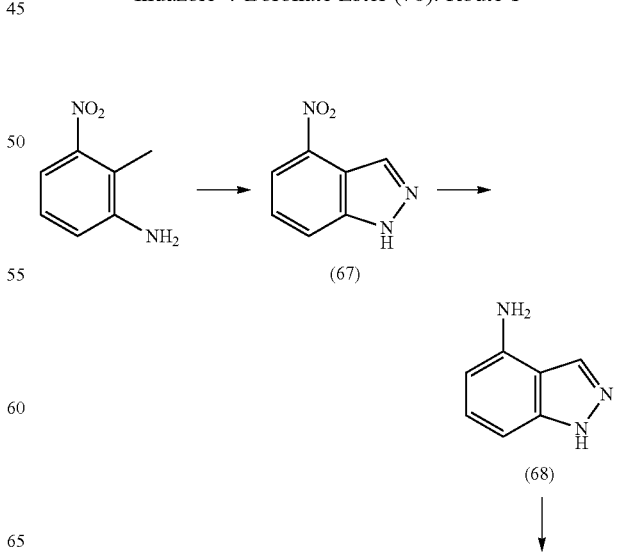

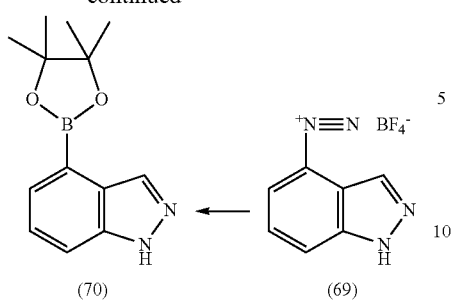

To a solution of 2-methyl-3-nitroaniline (2.27 g, 14.91 mmol) in acetic acid (60 mL) was added a solution of sodium nitrite (1.13 g, 1.1 eq.) in water (5 mL). After 2 h, the deep red solution was poured onto ice/water and the resulting precipitate collected by filtration to yield 4-nitro-1H-indazole (67) (1.98 g, 81%).

A mixture of 4-nitro-1H-indazole (760 mg, 4.68 mmol), palladium on charcoal (10%, cat.) and ethanol (30 mL) was stirred under a balloon of hydrogen for 4 h. The reaction mixture was then filtered through celite, and the solvent removed in vacuo to yield 1H-indazol-4-ylamine (68) (631 mg, 100%).

An aqueous solution of sodium nitrite (337 mg, 4.89 mmol) in water (2 mL) was added dropwise to a suspension of 1H-indazol-4-ylamine (631 mg, 4.74 mmol) in 6M hydrochloric acid (7.2 mL) at below 0° C. After stirring for 30 minutes, sodium tetrafluorobrate (724 mg) was added to the reaction mixture. A viscous solution resulted, which was filtered and washed briefly with water to yield 1H-indazole-4-diazonium tetrafluoroborate salt (69) (218 mg, 20%) as a deep red solid.

Dry MeOH (4 mL) was purged with argon for 5 minutes. To this was added 1H-indazole-4-diazonium tetrafluoroborate salt (218 mg, 0.94 mmol), bis-pinacolato diboron (239 mg, 1.0 eq.) and [1,1'-bis(diphenylphosphino)ferrocene]palladium (II) chloride (20 mg). The reaction mixture was stirred for 5 h and then filtered through celite. The residue was purified using flash chromatography to yield the desired title compound (70), (117 mg).

REFERENCE EXAMPLE 6

Indazole-4-Boronate Ester (70): Route 2

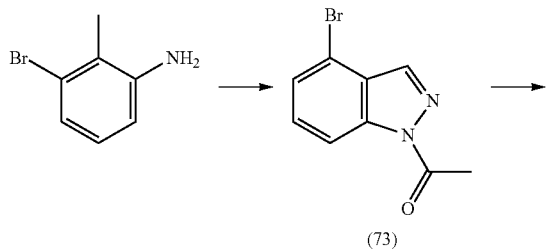

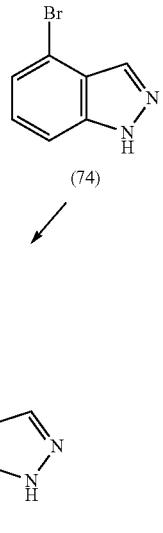

To a solution of 3-bromo-2-methyl aniline (5.0 g, 26.9 mmol) in chloroform (50 mL) was added potassium acetate (1.05 eq., 28.2 mmol, 2.77 g). Acetic anhydride (2.0 eq., 53.7 mmol, 5.07 mL) was added with concurrent cooling in ice-water. The mixture was then stirred at room temperature for 10 minutes after which time a white gelatinous solid formed. 18-Crown-6 (0.2 eq., 5.37 mmol, 1.42 g) was then added followed by iso-amyl nitrite (2.2 eq., 59.1 mmol, 7.94 mL) and the mixture was heated under reflux for 18 h. The reaction mixture was allowed to cool, was partitioned between chloroform (3×100 mL) and saturated aqueous sodium hydrogen carbonate (100 mL). The combined organic extracts were washed with brine (100 mL), separated and dried (MgSO$_4$).

The crude product was evaporated onto silica and purified by chromatography eluting with 20%→40% EtOAc-petrol to give the N-acetyl indazole (73) (3.14 g, 49%) as an orange solid followed by the indazole (74) (2.13 g, 40%) as a pale orange solid.

73: $^1$H NMR (400 MHz, CDCl$_3$) 2.80 (3H, s), 7.41 (1H, t, J=7.8 Hz), 7.50 (1H, d, J=7.8 Hz), 8.15 (1H, s), 8.40 (1H, d, J=7.8 Hz).

74: $^1$H NMR (400 MHz, CDCl$_3$) 7.25 (1H, t, J=7.3 Hz), 7.33 (1H, d, J=7.3 Hz), 7.46 (1H, d, J=7.3 Hz), 8.11 (1H, s), 10.20 (1H, br s),

To a solution of the N-acetyl indazole (3.09 g, 12.9 mmol) in MeOH (50 mL) was added 6N aqueous HCl (30 mL) and the mixture was stirred at room temperature for 7 h. The MeOH was evaporated and the mixture partitioned between EtOAc (2×50 mL) and water (50 mL). The combined organic layers were washed with brine (50 mL), separated and dried (MgSO$_4$). The solvent was removed by evaporation under reduced pressure to give an orange solid (2.36 g, 93%).

To a solution of the 4-bromoindazole (500 mg, 2.54 mmol) and bis(pinacolato)diboron (1.5 eq., 3.81 mmol) in DMSO (20 mL) was added potassium acetate (3.0 eq., 7.61 mmol, 747 mg; dried in drying pistol) and PdCl$_2$(dppf)$_2$ (3 mol %, 0.076 mmol, 62 mg). The mixture was degassed with argon and heated at 80° C. for 40 h. The reaction mixture was allowed to cool and partitioned between water (50 mL) and ether (3×50 mL). The combined organic layers were washed with brine (50 mL), separated and dried (MgSO$_4$). The crude material was purified by chromatography eluting with 30%→40% EtOAc-petrol to give an inseparable 3:1 mixture of the boronate ester (369 mg, 60%) and indazole (60 mg, 20%); this was isolated as a yellow gum which solidified upon standing to furnish (70) as an off-white solid.

¹H NMR (400 MHz, d₆-DMSO) (70) 1.41 (12H, s), 7.40 (1H, dd, J=8.4 Hz, 6.9 Hz), 7.59 (1H, d, J=8.4 Hz), 7.67 (1H, d, J=6.9 Hz), 10.00 (1H, br s), 8.45 (1H, s), and indazole: 7.40 (1H, t), 7.18 (1H, t, J=7.9 Hz), 7.50 (1H, d, J=9.1 Hz), 7.77 (1H, d, J=7.9 Hz), 8.09 (1H, s). Impurity at 1.25.

REFERENCE EXAMPLE 7

6-Fluoroindazole-4-Boronate Ester (75)

To a solution of 4-fluoro-2-nitrotoluene (3.44 g) in trifluoroacetic acid (13 mL) was added concentrated sulfuric acid (4 mL) followed by N-bromosuccinimide (5.92 g). The reaction mixture was stirred for 16 h and was then quenched with brine, extracted into ethyl acetate, and dried (MgSO₄). The solvent was removed in vacuo to furnish crude 1-bromo-5-fluoro-2-methyl-3-nitro-benzene (5.96 g).

To a solution of crude 1-bromo-5-fluoro-2-methyl-3-nitro-benzene (5.96 g) in MeOH (90 mL) was added concentrated hydrochloric acid (11.7 mL) and iron (6.1 g) and the reaction mixture was heated to reflux. After 16 h, the mixture was cooled, diluted with DCM, washed with sodium carbonate solution, dried (MgSO₄) and the solvent removed in vacuo. The residue was purified using flash chromatography to yield 3-bromo-5-fluoro-2-methyl-phenylamine (1.46 g).

To a solution of 3-bromo-5-fluoro-2-methyl-phenylamine (470 mg) in dioxane (6 mL) was added triethylamine (1.28 mL), palladium acetate (25 mg), 2-dicyclohexylphosphino biphenyl (161 mg) and pinacol borane (1.001 ml) and the mixture was heated to 80° C. for 4 h. The reaction mixture was cooled, diluted with chloroform, washed with brine, dried (MgSO₄) and the solvent removed in vacuo. The residue was purified using flash chromatography to yield the desired title compound (466 mg).

REFERENCE EXAMPLE 8

Preparation of 2-(1H-Indazol-4-yl)-4-morpholin-4-yl-thieno[3,2-d]pyrimidine-6-carbaldehyde (71)

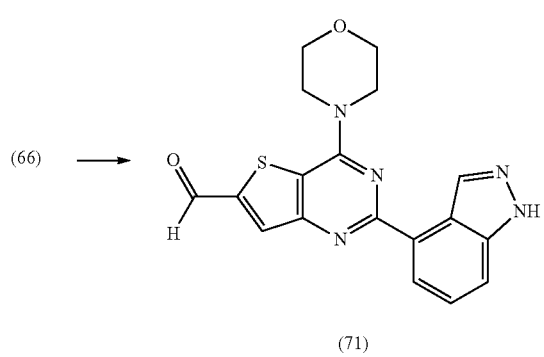 [SMILES: O=Cc1cc2nc(-c3cccc4[nH]ncc34)nc(N3CCOCC3)c2s1]

A mixture of 2-chloro-4-morpholin-4-yl-thieno[3,2-d]pyrimidine-6-carbaldehyde (66) (100 mg, 0.35 mmol), 4-(4,4,5,5-tetramethyl-[1,3,2]dioxaborolan-2-yl)-1H-indazole (70) (95 mg, 0.39 mmol) and sodium carbonate (112 mg) were suspended in toluene (2.5 mL), ethanol (1.5 mL) and water (0.7 mL). To this was added bis(triphenylphosphine)palladium(II) chloride (13.5 mg) and the reaction vessel was flushed with argon. The reaction mixture was microwaved at 120° C. for 1 h and then partitioned between DCM and water, the organic layer was washed with brine, dried over magnesium sulfate, filtered and evaporated in vacuo. The resulting residue was purified using flash chromatography to yield the title compound 71 (97 mg).

EXAMPLE 1

2-(1H-Indazol-4-yl)-6-(4-methyl-piperazin-1-ylmethyl)-4-morpholin-4-yl-thieno[3,2-d]pyrimidine (59) by Route 1

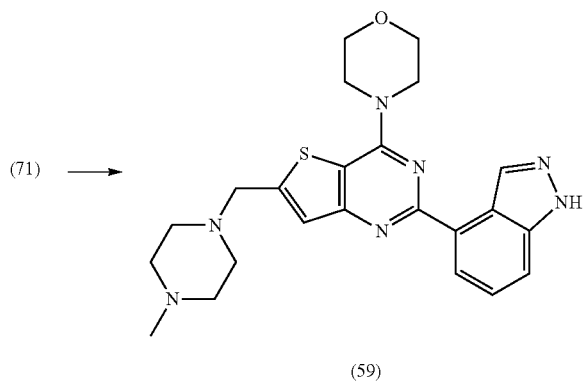 [SMILES: CN1CCN(Cc2cc3nc(-c4cccc5[nH]ncc45)nc(N4CCOCC4)c3s2)CC1]

To a mixture of 2-(1H-Indazol-4-yl)-4-morpholin-4-yl-thieno[3,2-d]pyrimidine-6-carbaldehyde (91 mg, 0.26 mmol), 1-methylpiperazine (34 mg, 0.36 mmol) and acetic acid (15 uL) in 1,2-dichloroethane (2 mL) was added sodium triacetoxyborohydride (60 mg, 0.28 mmol). The reaction mixture was stirred at room temperature overnight and then basified (NaHCO₃, saturated), diluted with DCM, and washed with brine. The organic layer was separated, dried (MgSO₄), filtered and evaporated in vacuo. The residue was purified using flash chromatography to give the title compound (33 mg).

¹H NMR ☐400 MHz, d₆-DMSO) 2.18 (s, 3H), 2.30-2.45 (br m, 4H), 2.48-2.55 (br m, 4H), 3.82-3.84 (m, 4H), 3.86 (s, 2H), 3.98-4.00 (m, 4H), 7.44-7.47 (m, 2H), 7.65 (d, 1H, J=8.2 Hz), 8.21 (d, 1H, J=7.2 Hz), 8.87 (s, 1H), 13.16 (br s, 1H); MS (ESI⁺) 450.1 (MH⁺).

EXAMPLE 2

2-(1H-Indazol-4-yl)-6-(4-methyl-piperazin-1-ylmethyl)-4-morpholin-4-yl-thieno[3,2-d]pyrimidine (59) by Route 2

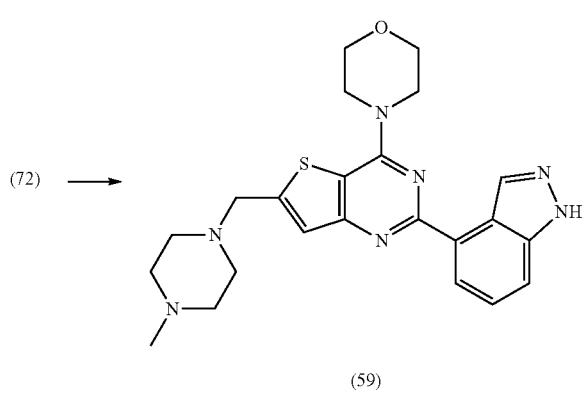 [SMILES: CN1CCN(Cc2cc3nc(-c4cccc5[nH]ncc45)nc(N4CCOCC4)c3s2)CC1]

Indazole-4-boronate ester (2.0 eq., 0.82 mmol), 2-Chloro-6-(4-methyl-piperazin-1-ylmethyl)-4-morpholin-4-yl-thieno[3,2-d]pyrimidine (compound 72 prepared in Reference Example 4: 150 mg, 0.41 mmol) and sodium carbonate (3.0 eq., 130 mg) were combined in a mixture of toluene (2 mL), ethanol (1 mL) and water (0.5 mL). $PdCl_2(PPh_3)_2$ (0.1 eq.) was added and the reaction mixture was flushed with Argon, and then heated in a microwave reactor at 130° C. for 2 h. Following extraction (DCM/brine) and flash column chromatography, the product was isolated as a white solid (149 mg, 81%)

EXAMPLE 2A

Further Compounds of the Invention

The following compounds of the invention were prepared by analogy with the process of Example 2. Compound 72 was replaced in each case by the appropriate precursor chloro compound, prepared by the method of Reference Example 4 using the relevant amine in place of 1-methyl piperazine. The preparation of the amine is described below where necessary. NMR data are given for each of the title compounds of the invention.

2-{4-[2-(1H-Indazol-4-yl)-4-morpholin-4-yl-thieno[3,2-d]pyrimidin-6-ylmethyl]-piperazin-1-yl}-ethanol (60)

Prepared via 2-[4-(2-Chloro-4-morpholin-4-yl-thieno[3,2-d]pyrimidin-6-ylmethyl)-piperazin-1-yl]-ethanol.
$^1$H NMR □400 MHz, $d_6$-DMSO) 2.40 (br m, 2H), 2.42-2.52 (b, 8H, under DMSO peak), 3.48 (q, 2H, J=6.0 Hz), 3.82-3.86 (m, 6H), 3.98-4.01 (m, 4H), 4.34 (br s, 1H), 7.44-7.48 (m, 2H), 7.65 (d, 1H, J=8.3 Hz), 8.21 (d, 1H, J=6.8 Hz), 8.87 (s, 1H), 13.15 (br s, 1H); MS ($ESI^+$) 480.1 ($MH^+$).

4-[2-(1H-Indazol-4-yl)-4-morpholin-4-yl-thieno[3,2-d]pyrimidin-6-ylmethyl]-piperazine-1-sulfonic acid dimethylamide (62)

Prepared via 4-(2-Chloro-4-morpholin-4-yl-thieno[3,2-d]pyrimidin-6-ylmethyl)-piperazine-1-sulfonic acid dimethylamide.
$^1$H NMR □400 MHz, $CDCl_3$) 2.63-2.66 (m, 4H), 2.84 (s, 6H), 3.31-3.34 (m, 4H), 3.89 (s 2H), 3.92-3.94 (m, 4H), 4.08-4.11 (m, 4H), 7.39 (s, 1H), 7.51 (t, 1H, J=8.1 Hz), 7.60 (d, 1H, J=8.1 Hz), 8.28 (d, 1H, J=6.7 Hz), 9.02 (s, 1H), 10.12 (br s, 1H); MS ($ESI^+$) 543.1 ($MH^+$).

{4-[2-(1H-Indazol-4-yl)-4-morpholin-4-yl-thieno[3,2-d]pyrimidin-6-ylmethyl]-piperazin-1-yl}-morpholin-4-yl-methanone (76)

Prepared via [4-(2-Chloro-4-morpholin-4-yl-thieno[3,2-d]pyrimidin-6-ylmethyl)-piperazin-1-yl]-morpholin-4-yl-methanone, prepared from morpholin-4-yl-piperazin-1-yl-methanone.
Amine preparation: a mixture of 4-morpholinocarbonyl chloride (0.38 ml), 1-BOC-piperazine (552 mg) and potassium carbonate (439 mg) in MeCN (7 mL) was stirred at room temperature for 3 h. The reaction mixture was then diluted with DCM, washed with brine, dried ($MgSO_4$) and the solvent removed in vacuo to yield 4-(morpholine-4-carbonyl)-piperazine-1-carboxylic acid tert-butyl ester (865 mg). Treatment of this compound with HCl in DCM/MeOH yielded the desired compound, which was isolated as the hydrochloride salt.
$^1$H NMR (400 MHz, $CDCl_3$): 2.55-2.58 (4H, m), 3.28-3.32 (4H, m), 3.35-3.39 (4H, m), 3.67-3.71 (4H, m), 3.88 (2H, s), 3.92-3.96 (4H, m), 4.08-4.12 (4H, m), 7.39 (1H, s), 7.52 (1H, t, J=8.0 Hz), 7.60 (1H, d, J=6.3 Hz), 8.30 (1H, d, J=7.0 Hz), 9.02 (1H, s), 10.10 (1H, br); MS ($ESI^+$) 549 ($MH^+$).

4-[2-(1H-Indazol-4-yl)-4-morpholin-4-yl-thieno[3,2-d]pyrimidin-6-ylmethyl]-piperazine-1-carboxylic acid (2-methoxy-ethyl)-methyl-amide (77)

Prepared via 4-(2-Chloro-4-morpholin-4-yl-thieno[3,2-d]pyrimidin-6-ylmethyl)-piperazine-1-carboxylic acid (2-methoxy-ethyl)-methyl-amide, prepared from piperazine-1-carboxylic acid (2-methoxy-ethyl)-methyl-amide.
Amine preparation: to N-BOC-piperazine (500 mg) in DCM (5 mL) and triethylamine (0.41 ml) was added 4-nitrophenyl chloroformate (541 mg). After 1 h the reaction mixture was diluted with DCM, washed with brine, dried ($MgSO_4$) and the solvent removed in vacuo to yield piperazine-1,4-dicarboxylic acid tert-butyl ester 4-nitro-phenyl ester (940 mg).
To piperazine-1,4-dicarboxylic acid tert-butyl ester 4-nitro-phenyl ester (500 mg) in THF (5 mL) was added N-(2-methoxyethyl)methylamine (254 mg) and the reaction mixture was heated to reflux for 24 h. The reaction mixture was concentrated in vacuo and purified using flash column chromatography to yield 4-[(2-methoxy-ethyl)-methyl-carbamoyl]-piperazine-1-carboxylic acid tert-butyl ester (304 mg). Treatment of this compound with HCl in DCM/MeOH yielded the desired compound, which was isolated as the hydrochloride salt.
$^1$H NMR (400 MHz, $CDCl_3$): 2.59-2.63 (4H, m), 2.90 (3H, s), 3.27-3.30 (4H, m), 3.31 (3H, s), 3.48 (2H, t), 3.57 (2H, t), 3.90 (2H, s), 3.92-3.96 (4H, m), 4.08-4.12 (4H, m), 7.39 (1H, s), 7.52 (1H, t), 7.60 (1H, d, J=6.3 Hz), 8.30 (1H, d, J=7.0 Hz), 9.02 (1H, s), 10.10 (1H, br); MS ($ESI^+$) 551 ($MH^+$).

2-{4-[2-(1H-Indazol-4-yl)-4-morpholin-4-yl-thieno[3,2-d]pyrimidin-6-ylmethyl]-piperazin-1-yl}-N,N-dimethyl-acetamide (78)

Prepared via 2-[4-(2-Chloro-4-morpholin-4-yl-thieno[3,2-d]pyrimidin-6-ylmethyl)-piperazin-1-yl]-N,N-dimethylacetamide, prepared from N,N-dimethyl-2-piperazin-1-yl-acetamide.
Amine preparation: a mixture of 1-BOC-piperazine (387 mg), 2-chloro-N,N-dimethylacetamide (0.43 mL) and triethylamine (0.58 mL) in chloroform was stirred at room temperature. After stirring overnight the reaction mixture was diluted with DCM, washed with brine, dried ($MgSO_4$) and the solvent removed in vacuo to yield 4-dimethylcarbamoylmethyl-piperazine-1-carboxylic acid tert-butyl ester (558 mg). Treatment of this compound with HCl in DCM/MeOH yielded the desired compound, which was isolated as the hydrochloride salt.
$^1$H NMR (400 MHz, $CDCl_3$): 2.63 (sbr, 8H, 4×$CH_2$), 2.95 (s, 3H, $CH_3$), 3.07 (s, 3H, $CH_3$), 3.20 (s, 2H, $CH_2$), 3.85 (s, 2H, $CH_2$), 3.90-3.93 (m, 4H, 2×$CH_2$), 4.07-4.10 (m, 4H, 2×$CH_2$), 4.36 (s, H, ArH), 7.49 (t, H, ArH, J=7.74 Hz), 7.57 (d, H, ArH, J=8.26 Hz), 8.26 (d, H, ArH, J=7.23 Hz), 9.00 (s, H, ArH), 10.25 (br s, H, NH); MS ($ESI^+$) 521.29 ($MH^+$).

4-[2-(1H-Indazol-4-yl)-4-morpholin-4-yl-thieno[3,2-d]pyrimidin-6-ylmethyl]-piperazine-1-carboxylic acid dimethylamide (79)

Prepared via 4-(2-Chloro-4-morpholin-4-yl-thieno[3,2-d]pyrimidin-6-ylmethyl)-piperazine-1-carboxylic acid dimethylamide, prepared from piperazine-1-carboxylic acid dimethylamide.

Amine preparation: To a solution of 1-BOC-piperazine (867 mg) in dry THF (8 mL) was added triethylamine (0.97 mL) followed by dimethylcarbamoyl chloride (0.51 mL). After stirring for 24 h the reaction mixture was then diluted with DCM, washed with brine, dried (MgSO$_4$) and the solvent was removed in vacuo to yield 4-dimethylcarbamoyl-piperazine-1-carboxylic acid tert-butyl ester (940 mg). Treatment of this compound with HCl in DCM/MeOH yielded the desired compound, which was isolated as the hydrochloride salt.

$^1$H NMR (400 MHz, CDCl$_3$): 2.57-2.61 (4H, m), 2.87 (6H, s), 3.30-3.35 (4H, m), 3.89 (2H, s), 3.92-3.96 (4H, m), 4.08-4.12 (4H, m), 7.39 (1H, s), 7.52 (1H, t, J=8.0 Hz), 7.60 (1H, d, J=6.3), 8.30 (1H, d, J=7.0 Hz), 9.02 (1H, s), 10.10 (1H, br); (ESI$^+$): MS (ESI$^+$) 507 (MH$^+$).

2-(1H-Indazol-4-yl)-4-morpholin-4-yl-6-[4-(3-morpholin-4-yl-propane-1-sulfonvyl)-piperazin-1-ylmethyl]-thieno[3,2-d]pyrimidine (80)

Prepared via 2-Chloro-4-morpholin-4-yl-6-[4-(3-morpholin-4-yl-propane-1-sulfonyl)-piperazin-1-ylmethyl]-thieno[3,2-d]pyrimidine, prepared from 4-[3-(piperazine-1-sulfonyl)-propyl]-morpholine.

Amine preparation: A mixture of 1-BOC-piperazine (3.26 g), 3-chloropropanesulfonyl chloride (2.63 g) and triethylamine (2.68 mL) was stirred at room temperature in DCM (25 mL). After 2 h the reaction mixture was diluted with DCM, washed with brine, dried (MgSO$_4$) and the solvent removed in vacuo to yield 4-(3-chloro-propane-1-sulfonyl)-piperazine-1-carboxylic acid tert-butyl ester (4.65 g). A mixture of 4-(3-chloro-propane-1-sulfonyl)-piperazine-1-carboxylic acid tert-butyl ester (4.65 g), potassium iodide (1.1 g), potassium carbonate and morpholine (1.6 mL) was heated to reflux in MeCN (100 ml). After 16 h, the reaction mixture was cooled, diluted with DCM, washed with brine, dried (MgSO$_4$) and the solvent removed in vacuo to yield 4-(3-morpholin-4-yl-propane-1-sulfonyl)-piperazine-1-carboxylic acid tert-butyl ester (4.8 g). Treatment of this compound with HCl in DCM/MeOH yielded the desired compound, which was isolated as the hydrochloride salt.

$^1$H NMR (400 MHz, CDCl$_3$): 1.98-2.02 (m, 2H), 2.44-2.47 (m, 6H), 2.67-2.69 (m, 4H), 2.99-3.03 (m, 2H), 3.36-3.38 (m, 4H), 3.69-3.71 (m, 4H), 3.90 (s, 2H), 3.91-3.93 (m, 4H), 4.08-4.10 (m, 4H), 7.39 (s, H, ArH), 7.50 (t, H, ArH, J=7.7 Hz), 7.58 (d, H, ArH, J=8.32 Hz), 8.27 (d, H, ArH, J=7.44 Hz), 9.00 (s, H, ArH), 10.10 (br s, H, NH); MS (ESI$^+$) 627.29 (MH$^+$).

{1-[2-(1H-Indazol-4-yl)-4-morpholin-4-yl-thieno[3,2-d]pyrimidin-6-ylmethyl]-piperidin-4-yl}-(2-methoxy-ethyl)-methyl-amine (81)

Prepared via [1-(2-Chloro-4-morpholin-4-yl-thieno[3,2-d]pyrimidin-6-ylmethyl)-piperidin-4-yl]-(2-methoxy-ethyl)-methyl-amine, prepared from (2-methoxy-ethyl)-methyl-piperidin-4-yl-amine.

Amine preparation: a mixture of N-BOC-4-piperidine (500 mg), N-(2-methoxyethyl)methylamine (335 mg), acetic acid (0.15 mL) and sodium triacetoxyborohydride (797 mg) was stirred at room temperature in 1,2-dichloroethane (5 mL). After stirring overnight, the reaction mixture was diluted with chloroform, washed with sodium bicarbonate solution, dried (MgSO$_4$) and the solvent removed in vacuo. The residue was purified using flash column chromatography to yield 4-[(2-methoxy-ethyl)-methyl-amino]-piperidine-1-carboxylic acid tert-butyl ester. Treatment of this compound with HCl in DCM/MeOH yielded the desired compound, which was isolated as the hydrochloride salt.

$^1$H NMR (400 MHz, CDCl$_3$): 1.62-1.72 (2H, m), 1.76-1.84 (2H, m), 2.10-2.18 (2H, m), 2.36 (3H, s), 2.40-2.48 (1H, m), 2.68 (2H, t, J=6.0 Hz), 3.04-3.11 (2H, m), 3.38 (3H, s), 3.50 (2H, t, J=6.3 Hz), 3.85 (2H, s), 3.92-3.97 (4H, m), 4.08-4.12 (4H, m), 7.39 (1H, s), 7.52 (1H, t, J=8.0 Hz), 7.60 (1H, d, J=6.3 Hz), 8.30 (1H, d, J=7.0 Hz), 9.02 (1H, s), 10.10 (1H, br); MS (ESI$^+$) 522 (MH$^+$).

3-4-[2-(1H-Indazol-4-yl)-4-morpholin-4-yl-thieno[3,2-d]pyrimidin-6-ylmethyl]-piperazine-1-sulfonyl}-propyl)-dimethyl-amine (82)

Prepared via {3-[4-(2-Chloro-4-morpholin-4-yl-thieno[3,2-d]pyrimidin-6-ylmethyl)-piperazine-1-sulfonyl]-propyl}-dimethyl-amine, prepared from dimethyl-[3-(piperazine-1-sulfonyl)-propyl]-amine. The amine preparation was as for compound 80 above.

$^1$H NMR (400 MHz, CDCl$_3$): 2.00-2.08 (2H, m), 2.26 (6H, s), 2.42 (2H, t, J=6.7), 2.68-2.72 (4H, m), 3.00-3.05 (2H, m), 3.37-3.41 (4H, m), 3.90 (2H, s), 3.92-3.96 (4H, m), 4.08-4.12 (4H, m), 7.39 (1H, s), 7.52 (1H, t, J=8.0), 7.60 (1H, d, J=6.3), 8.30 (1H, d, J=7.0), 9.02 (1H, s), 10.10 (1H, br); MS (ESI$^+$) 585 (MH$^+$).

2-{4-[2-(1H-Indazol-4-yl)-4-morpholin-4-yl-thieno[3,2-d]pyrimidin-6-ylmethyl]-piperazin-1-yl}-2-methyl-propan-1-ol (83)

Prepared via 2-[4-(2-Chloro-4-morpholin-4-yl-thieno[3,2-d]pyrimidin-6-ylmethyl)-piperazin-1-yl]-2-methyl-propan-1-ol, prepared from 2-methyl-2-piperazin-1-yl-propan-1-ol.

Amine preparation: a mixture of BOC-piperazine (1.87 g), ethyl 2-bromoisobutyrate (5.90 g) and potassium carbonate (1.53 g) in MeCN (20 mL) was heated in a sealed tube at 80° C. for 3 days. The reaction mixture was cooled, diluted with chloroform, washed with brine, dried (MgSO$_4$) and the solvent removed in vacuo. The residue was purified by flash column chromatography to yield 4-(1-ethoxycarbonyl-1-methyl-ethyl)-piperazine-1-carboxylic acid tert-butyl ester (2.97 g).

Treatment of 4-(1-ethoxycarbonyl-1-methyl-ethyl)-piperazine-1-carboxylic acid tert-butyl ester with lithium aluminium hydride in ether yielded the corresponding alcohol, 4-(2-hydroxy-1,1-dimethyl-ethyl)-piperazine-1-carboxylic acid tert-butyl ester. Treatment of this compound with HCl in DCM/MeOH yielded the desired compound, which was isolated as the hydrochloride salt.

$^1$H NMR (400 MHz, CDCl$_3$): 9.02 (1H, s), 8.25 (1H, d), 7.60 (1H, d), 7.51-7.49 (1H, m), 7.39 (1H, s), 4.08-4.06 (4H, m), 3.90-3.88 (4H, m), 3.85 (2H, s), 3.46 (2H, s), 2.70-2.50 (8H, m), 1.05 (6H, s); MS (ESI$^+$) 508 (MH$^+$).

1'-[2-(1H-Indazol-4-yl)-4-morpholin-4-yl-thieno[3,2-d]pyrimidin-6-ylmethyl]-[1,4']bipiperidinyl (84)

Prepared via 1'-(2-Chloro-4-morpholin-4-yl-thieno[3,2-d]pyrimidin-6-ylmethyl)-[1,4']bipiperidinyl, prepared from 4-piperidinopiperidine.

¹H NMR (400 MHz, CDCl₃): 1.40-1.50 (2H, br), 1.50-1.75 (6H, br), 1.80-1.90 (2H, br), 2.21 (2H, t, J=10.7), 2.35-2.43 (1H, br), 2.50-2.60 (4H, br), 3.04-3.10 (2H, br. d, J=11.4), 3.84 (2H, s), 3.92-3.96 (4H, m), 4.08-4.12 (4H, m), 7.39 (1H, s), 7.52 (1H, t, J=8.0), 7.60 (1H, d, J=6.3), 8.30 (1H, d, J=7.0), 9.02 (1H, s), 10.10 (1H, br); MS (ESI⁺) 518 (MH⁺).

2-(1H-Indazol-4-yl)-4-morpholin-4-yl-6-(4-morpholin-4-yl-piperidin-1-ylmethyl)-thieno[3,2-d]pyrimidine (85)

Prepared via 2-Chloro-4-morpholin-4-yl-6-(4-morpholin-4-yl-piperidin-1-ylmethyl)-thieno[3,2-d]pyrimidine, prepared from 4-morpholinopiperidine.
¹H NMR (400 MHz, CDCl₃): 1.55-1.68 (2H, m), 1.83-1.90 (2H, m), 2.11-2.18 (2H, m), 2.18-2.25 (1H, m), 2.54-2.60 (4H, m), 3.05-3.11 (2H, m), 3.70-3.76 (4H, m), 3.84 (2H, s), 3.92-3.96 (4H, m), 4.08-4.12 (4H, m), 7.39 (1H, s), 7.52 (1H, t, J=8.0), 7.60 (1H, d, J=6.3), 8.30 (1H, d, J=7.0), 9.02 (1H, s), 10.10 (1H, br); MS (ESI⁺) 520 (MH⁺).

2-(1H-Indazol-4-yl)-4-morpholin-4-yl-6-(4-pyrimidin-2-yl-piperazin-1-ylmethyl)-thieno[3,2-d]pyrimidine (86)

Prepared via 2-Chloro-4-morpholin-4-yl-6-(4-pyrimidin-2-yl-piperazin-1-ylmethyl)-thieno[3,2-d]pyrimidine, prepared from 1-(2-pyrimidyl)piperazine.
¹H NMR (400 MHz, CDCl₃): 2.64-2.70 (4H, m), 3.87-3.96 (10H, m), 4.10-4.14 (4H, m), 6.50 (1H, t, J=4.8), 7.40 (1H, s), 7.52 (1H, t, J=7.8), 7.60 (1H, d, J=8.3), 8.29-8.33 (3H, m), 9.02 (1H, s), 10.10 (1H, br); MS (ESI⁺) 514 (MH⁺).

1-(2-Hydroxy-ethyl)-4-[2-(1H-indazol-4-yl)-4-morpholin-4-yl-thieno[3,2-d]pyrimidin-6-ylmethyl]-piperazin-2-one (87)

Prepared via 4-(2-Chloro-4-morpholin-4-yl-thieno[3,2-d]pyrimidin-6-ylmethyl)-1-(2-hydroxy-ethyl)-piperazin-2-one, prepared from 1-(2-hydroxy-ethyl)-piperazin-2-one.
Amine preparation: to 4-CBZ-piperazin-2-one (1.95 g) in DMF (5 mL) at 0° C. was added sodium hydride (60% dispersion in mineral oil, 660 mg) in several aliquots. After stirring for 1 h, 2-bromoethylacetate (1.38 ml) was added. The reaction mixture was stirred at room temperature overnight; it was then diluted with ethyl acetate, washed with brine, dried (MgSO₄) and the solvent was removed in vacuo.
The resulting residue was purified using flash chromatography to yield 4-(2-acetoxy-ethyl)-3-oxo-piperazine-1-carboxylic acid benzyl ester (925 mg).
¹H NMR (400 MHz, d₆-DMSO): 2.77 (2H, d, J=5.5 Hz), 3.16 (2H, s), 3.32-3.36 (2H, m), 3.38-3.42 (2H, m), 3.51-3.55 (2H, m), 3.80-3.85 (4H, m), 3.97 (2H, s), 4.00-4.04 (4H, m), 4.70 (1H, t, J=5.4 Hz, OH), 7.45 (1H, t, J=7.7 Hz), 7.50 (1H, s), 7.66 (1H, d, J=8.2 Hz), 8.22 (1H, d, J=7.3 Hz), 8.89 (1H, s), 13.15 (1H, br, NH); MS (ESI⁺) 494 (MH⁺).

6-(4-Cyclopropylmethyl-piperazin-1-ylmethyl)-2-(1H-indazol-4-yl)-4-morpholin-4-yl-thieno[3,2-d]pyrimidine (88)

Prepared via 2-Chloro-6-(4-cyclopropylmethyl-piperazin-1-ylmethyl)-4-morpholin-4-yl-thieno[3,2-d]pyrimidine, prepared from 1-cyclopropylmethyl-piperazine.
Amine preparation: A mixture of BOC-piperazine (887 mgg), (bromomethyl)cyclopropane (0.5 mL) and potassium carbonate (779 mg) in MeCN (10 mL) was heated to reflux for 16 h. The reaction mixture was cooled, diluted with chloroform, washed with brine, dried (MgSO₄) and the solvent removed in vacuo. The residue was purified using flash chromatography to yield 4-yclopropylmethyl-piperazine-1-carboxylic acid tert-butyl ester (1.05 g). Treatment of this compound with HCl in DCM/MeOH yielded the desired compound, which was isolated as the hydrochloride salt.
¹H NMR (400 MHz, CDCl₃): 0.07-0.14 (m, 2H, 2×CH₂), 0.48-0.51 (m, 2H, 2×CH), 0.8-0.95 (m, H, CH), 2.28-2.32 (m, 2H, CH₂), 2.5-2.7 (m, 8H, 4×CH₂), 3.86 (s, 2H, CH₂), 3.90-3.93 (m, 4H, 2×CH₂), 4.07-4.11 (m, 4H, 2×CH₂), 7.38 (s, H, ArH), 7.50 (t, H, ArH, J=7.79 Hz), 7.58 (d, H, ArH, J=8.28 Hz), 8.28 (d, H, ArH, J=7.57 Hz), 9.02 (s, H, ArH), 10.15 (sbr, H, NH); MS (ESI⁺) 490.19 (MH⁺).

2-(1H-Indazol-4-yl)-4-morpholin-4-yl-6-(4-pyridin-2-yl-piperazin-1-yvlmethyl)-thieno[3,2-d]pyrimidine (89)

Prepared via 2-Chloro-4-morpholin-4-yl-6-(4-pyridin-2-yl-piperazin-1-ylmethyl)-thieno[3,2-d]pyrimidine, prepared from 1-pyridin-2-yl-piperazine (commercially available).
¹H NMR (400 MHz, CDCl₃): 10.1 (1H, br s), 9.02 (1H, s), 8.25 (1H, d), 8.22-8.20 (1H, m), 7.60 (1H, d), 7.51-7.43 (2H, m), 7.39 (1H, s), 6.61-6.60 (1H, m), 4.08-4.06 (4H, m), 3.90-3.88 (6H, m), 3.60-3.58 (4H, m), 2.72-2.70 (4H, m); MS (ESI⁺) 513 (MH⁺).

2-(1H-Indazol-4-yl)-4-morpholin-4-yl-6-[4-(2,2,2-trifluoro-ethyl)-piperazin-1-ylmethyl]-thieno[3,2-d]pyrimidine (90)

Prepared via 2-Chloro-4-morpholin-4-yl-6-[4-(2,2,2-trifluoro-ethyl)-piperazin-1-ylmethyl]-thieno[3,2-d]pyrimidine, prepared from 1-(2,2,2-trifluoro-ethyl)-piperazine.
Amine preparation: to BOC-piperazine (4 g) in DCM (40 mL) was added trifluoroacetic anhydride (6.06 mL) and triethylamine (3.29 mL). After stirring overnight the reaction mixture was diluted with diluted with DCM, washed with sodium bicarbonate solution, dried (MgSO₄) and the solvent removed in vacuo to yield 4-(2,2,2-trifluoro-acetyl)-piperazine-1-carboxylic acid tert-butyl ester (6.06 g).
To 4-(2,2,2-trifluoro-acetyl)-piperazine-1-carboxylic acid tert-butyl ester (6.06 g) in dry THF (60 mL) was added borane dimethyl sulfide complex (4.5 ml) and the reaction mixture was heated to reflux. After 2 h the reaction mixture was cooled to 0° C. and MeOH was carefully added, followed by water. The organics were extracted into ethyl acetate, dried (MgSO₄) and the solvent removed in vacuo to yield 4-(2,2,2-trifluoro-ethyl)-piperazine-1-carboxylic acid tert-butyl ester (4.46 g). Treatment with HCl in DCM/MeOH yielded the desired compound, which was isolated as the hydrochloride salt.
¹H NMR (400 MHz, CDCl₃): 2.56 (4H, m), 2.69 (4H, m), 2.93 (2H, q), 3.79 (2H, s), 3.85 (4H, m), 4.02 (4H, m), 7.23 (1H, s), 7.44 (1H, d), 7.52 (1H, d), 8.21 (1H, d), 8.94 (1H, s).

2-(1H-Indazol-4-yl)-4-morpholin-4-yl-6-(4-thiazol-2-yl-piperazin-1-ylmethyl)-thieno[3,2-d]pyrimidine (91)

Prepared via 2-Chloro-4-morpholin-4-yl-6-(4-thiazol-2-yl-piperazin-1-ylmethyl)-thieno[3,2-d]pyrimidine, prepared from 1-thiazol-2-yl-piperazine (commercially available).
¹H NMR (400 MHz, CDCl₃): 10.1 (1H, br s), 9.02 (1H, s), 8.25 (1H, d), 7.60 (1H, d), 7.51-7.49 (2H, m), 7.39 (1H, s), 7.20 (1H, d), 6.60 (1H, d), 4.08-4.06 (4H, m), 3.90-3.88 (6H, m), 3.55-3.50 (4H, m), 2.72-2.70 (4H, m); MS (ESI$^+$) 519 (MH$^+$).

2-(6-Fluoro-1H-indazol-4-yl)-6-(4-methyl-piperazin-1-ylmethyl)-4-morpholin-4-yl-thieno[3,2-d]pyrimidine (92)

Prepared by treatment of 5-fluoro-2-methyl-3-[6-(4-methyl-piperazin-1-ylmethyl)-4-morpholin-4-yl-thieno[3,2-d]pyrimidin-2-yl]-phenylamine with isoamyl nitrite in chloroform and acetic acid.

$^1$H NMR (400 MHz, CDCl$_3$): 10.1 (1H, br s), 9.02 (1H, s), 8.10 (1H, dd), 7.39 (1H, s), 7.22 (1H, dd), 4.08-4.06 (4H, m), 3.90-3.88 (4H, m), 3.85 (2H, s), 2.70-2.50 (8H, m), 2.30 (3H, s); MS (ESI$^+$) 468 (MH$^+$).

2-(1H-Indazol-4-yl)-4-morpholin-4-yl-6-(4-pyridin-2-ylmethyl-piperazin-1-ylmethyl)-thieno[3,2-d]pyrimidine (93)

Prepared via 2-Chloro-4-morpholin-4-yl-6-(4-pyridin-2-ylmethyl-piperazin-1-ylmethyl)-thieno[3,2-d]pyrimidine. The amine was prepared as described for compound 95.

$^1$H NMR (400 MHz, CDCl$_3$): 2.61 (m, 8H, 4×CH$_2$), 3.70 (s, 2H, CH$_2$), 3.86 (s, 2H, CH$_2$), 3.90-3.93 (m, 4H, 2×CH$_2$), 4.07-4.10 (m, 4H, 2×CH$_2$), 7.14-7.17 (m, H, ArH), 7.36 (s, H, ArH), 7.40 (d, H, ArH, J=7.78 Hz), 7.49 (t, H, ArH, J=7.77 Hz), 7.57 (d, H, ArH, J=8 Hz), 7.64 (t, H, ArH, J=7.64 Hz), 8.27 (d, H, ArH, J=6.64 Hz), 8.56 (d, H, ArH, J=4.83 Hz), 9.0 (s, H, ArH), 10.12 (sbr, H, NH); MS (ESI$^+$) 527.28 (MH$^+$).

2-(1H-Indazol-4-yl)-4-morpholin-4-yl-6-(4-thiazol-2-ylmethyl-piperazin-1-ylmethyl)-thieno[3,2-d]pyrimidine (94)

Prepared via 2-Chloro-4-morpholin-4-yl-6-(4-thiazol-2-ylmethyl-piperazin-1-ylmethyl)-thieno[3,2-d]pyrimidine, prepared from 1-thiazol-2-ylmethyl-piperazine. The amine was prepared as described for compound 95 below.

$^1$H NMR (400 MHz, CDCl$_3$): 2.67 (m, 8H, 4×CH$_2$), 3.87 (s, 2H, CH$_2$), 3.91-3.93 (m, 6H, 3×CH$_2$), 4.07-4.10 (m, 4H, 2×CH$_2$), 7.28 (d, H, ArH, J=3.23 Hz), 7.37 (s, H, ArH), 7.49 (t, H, ArH, J=7.73 Hz), 7.58 (d, H, ArH, J=8.31 Hz), 7.70 (d, H, ArH, J=3.32 Hz), 8.27 (d, H, ArH, J=6.79 Hz), 9.0 (s, H, ArH), 10.1 (sbr, H, NH).

2-(1H-Indazol-4-yl)-6-[4-(5-methyl-furan-2-ylmethyl)-piperazin-1-ylmethyl]-4-morpholin-4-yl-thieno[3,2-d]pyrimidine (95)

Prepared via 2-Chloro-6-[4-(5-methyl-furan-2-ylmethyl)-piperazin-1-ylmethyl]-4-morpholin-4-yl-thieno[3,2-d]pyrimidine, prepared from 1-(5-methyl-furan-2-ylmethyl)-piperazine.

Amine preparation: A mixture of 1-BOC-piperazine (1.63 g), 5-methyl furfural (964 mg) and acetic acid (0.50 mL) was stirred in 1,2-dichloroethane (10 mL) at room temperature. To this was added sodium triacetoxyborohydride (2.04 g) and the reaction mixture was stirred overnight. The reaction mixture was diluted with chloroform, washed with brine, dried (MgSO$_4$) and the solvent was removed in vacuo to liberate 4-(5-methyl-furan-2-ylmethyl)-piperazine-1-carboxylic acid tert-butyl ester as an orange oil. Treatment of this compound with HCl in DCM/MeOH yielded the desired compound, which was isolated as the hydrochloride salt.

$^1$H NMR (400 MHz, CDCl$_3$): 10.1 (1H, br s), 9.02 (1H, s), 8.28 (1H, d), 7.60 (1H, d), 7.51-7.48 (1H, m), 6.10 (1H, d), 5.88 (1H, d), 4.08-4.06 (4H, m), 3.90-3.88 (4H, m), 3.83 (2H, s), 3.51 (2H, s), 2.70-2.50 (8H, m), 2.26 (3H, s); MS (ESI$^+$) 530 (MH$^+$).

1-[2-(1H-Indazol-4-yl)-4-morpholin-4-yl-thieno[3,2-d]pyrimidin-6-ylmethyl]-piperidine-4-carboxylic acid amide (96)

Prepared via 1-(2-Chloro-4-morpholin-4-yl-thieno[3,2-d]pyrimidin-6-ylmethyl)-piperidine-4-carboxylic acid amide, prepared using isonipecotamide (commercially available).

$^1$H NMR (400 MHz, d$_6$-DMSO): 1.52-1.74 (4H, m); 2.00-2.16 (3H, m); 2.90-2.98 (2H, m); 3.80-3.90 (6H, m); (4H, t, J=4.7 Hz); 6.70 (1H, s); 7.20 (1H, s); 7.48 (2H, t, J=7.7 Hz); 7.65 (1H, d, J=8.2 Hz); 8.22 (1H, d, J=7.3 Hz), 8.88 (1H, s), 13.15 (1H, s); MS (ESI$^+$) 478 (MH$^+$).

2-(1H-Indazol-4-yl)-6-[4-(2-methoxy-1,1-dimethyl-ethyl)-piperazin-1-ylmethyl]-4-morpholin-4-yl-thieno[3,2-d]pyrimidine (97)

Prepared via 2-Chloro-6-[4-(2-methoxy-1,1-dimethyl-ethyl)-piperazin-1-ylmethyl]-4-morpholin-4-yl-thieno[3,2-d]pyrimidine, prepared from 1-(2-methoxy-1,1-dimethyl-ethyl)-piperazine.

Amine preparation: a mixture of benzylpiperazine, methoxyacetyl chloride and triethylamine was stirred in DCM for 2 h to yield 1-(4-benzyl-piperazin-1-yl)-2-methoxy-ethanone following standard work up.

To a solution of 1-(4-benzyl-piperazin-1-yl)-2-methoxy-ethanone (6.14 g) in dry THF (80 mL) at −10° C. was added zirconium chloride (5.76 g). After 30 minutes methyl magnesium bromide (3.0M solution in ether, 49.6 mL) was added in a dropwise manner. The reaction mixture was allowed to warm to room temperature. After stirring for 1 day, the reaction mixture was cooled, diluted with chloroform, washed with brine, dried (MgSO$_4$) and the was solvent removed in vacuo. The resulting residue was purified using flash chromatography to yield 1-benzyl-4-(2-methoxy-1,1-dimethyl-ethyl)-piperazine. Subsequent transfer hydrogenation, using ammonium formate and 10% palladium on carbon in MeOH furnished the desired compound.

$^1$H NMR (400 MHz, CDCl$_3$): 1.07 (s, 6H, 2×CH$_3$), 2.61 (m, 4H, 2×CH$_2$), 2.69 (m, 4H, 2×CH$_2$), 3.26 (s, 2H, CH$_2$), 3.33 (s, 3H, CH$_3$), 3.83 (s, 2H, CH$_2$), 3.90-3.93 (m, 4H, 2×CH$_2$), 4.07-4.10 (m, 4H, 2×CH$_2$), 7.36 (s, H, ArH), 7.49 (t, H, ArH, J=7.72 Hz), 7.57 (d, H, ArH, J=8.25 Hz), 8.26 (d, H, ArH, J=7.13 Hz), 9.0 (s, H, ArH), 10.1 (sbr, H, NH); MS (ESI$^+$) 522 (MH$^+$).

2-(1H-Indazol-4-yl)-6-[(3R,5S)-4-(2-methoxy-ethyl)-3,5-dimethyl-piperazin-1-ylmethyl]-4-morpholin-4-yl-thieno[3,2-d]pyrimidine (98)

Prepared via 2-Chloro-6-[(3R,5S)-4-(2-methoxy-ethyl)-3,5-dimethyl-piperazin-1-ylmethyl]-4-morpholin-4-yl-thieno[3,2-d]pyrimidine, prepared from (2R,6S)-1-(2-methoxy-ethyl)-2,6-dimethyl-piperazine.

Amine preparation: to a solution of 2,6-dimethylpiperazine (predominantly cis) (250 mg), tert-butanol (2.5 mL), sodium hydroxide (88 mg) and water (0.5 mL) was added a solution of di-tert-butyl-dicarbonate (478 mg) in tert-butanol (0.5 mL). After stirring overnight, the reaction mixture was diluted with ethyl acetate, washed with brine, dried (MgSO$_4$)

and the solvent was removed in vacuo to yield (3R,5S)-3,5-dimethyl-piperazine-1-carboxylic acid tert-butyl ester (400 mg).

A mixture of (3R,5S)-3,5-dimethyl-piperazine-1-carboxylic acid tert-butyl ester (1.5 g), 2-bromoethyl methyl ether (1.32 mL) and potassium carbonate (1.06 g) was heated to 120° C. in DMF (15 mL) for 2 days. The reaction mixture was cooled, diluted with ethyl acetate, washed with brine, dried (MgSO$_4$) and the solvent was removed in vacuo to liberate (3R,5S)-4-(2-methoxy-ethyl)-3,5-dimethyl-piperazine-1-carboxylic acid tert-butyl ester (1.4 g) after column chromatography.

Removal of the BOC group with HCl yielded the desired compound, which was isolated as the hydrochloride salt.

$^1$H NMR (400 MHz, CDCl$_3$): 1.01 (6H, d), 1.9 (2H, m), 2.61 (4H, m), 2.82 (2H, t), 3.27 (3H, s), 3.37 (2H, t), 3.71 (2H, s), 3.85 (4H, m), 4.02 (4H, m), 7.3 (1H, s), 7.43 (1H, t), 7.51 (1H, d), 8.21 (1H, d), 8.95 (1H, s), 10.10 (1H, m); MS (ESI$^+$) 522.35 (MH$^+$).

1-[2-(1H-Indazol-4-yl)-4-morpholin-4-yl-thieno[3,2-d]pyrimidin-6-ylmethyl]-piperidine-4-carboxylic acid (2-methoxy-ethyl)-methyl-amide (99)

Prepared via 1-[2-(1H-Indazol-4-yl)-4-morpholin-4-yl-thieno[3,2-d]pyrimidin-6-ylmethyl]-piperidine-4-carboxylic acid (2-methoxy-ethyl)-methyl-amide, prepared from piperidine-4-carboxylic acid (2-methoxy-ethyl)-methyl-amide. The amine was prepared as described for compound 100.

$^1$H NMR (400 MHz, CDCl$_3$): 1.71 (2H, m), 1.98 (2H, t), 2.18 (2H, m), 2.46-2.70 (1H, m); 2.99+3.12 (3H, s, 2× rotamers), 3.08 (2H, m), 3.34 (3H, s), 3.42-3.62 (4H, m), 3.86 (2H, s), 3.95 (4H, m), 4.10 (4H, m), 7.36 (1H, s), 7.50 (1H, t), 7.58 (1H, d), 8.28 (1H, d), 9.01 (1H, s), 10.07 (1H, br s); MS (ESI$^+$) 550 (MH$^+$).

1-[2-(1H-Indazol-4-yl)-4-morpholin-4-yl-thieno[3,2-d]pyrimidin-6-ylmethyl]-piperidine-4-carboxylic acid dimethylamide (100)

Prepared via 1-(2-Chloro-4-morpholin-4-yl-thieno[3,2-d]pyrimidin-6-ylmethyl)-piperidine-4-carboxylic acid dimethylamide, prepared from piperidine-4-carboxylic acid dimethylamide.

Amine preparation: to a stirring solution of BOC-isonipecotic acid (400 mg) in DMF (4 mL) was added 1,1'-carbonyldiimidazole (560 mg). The reaction mixture was stirred overnight and then dimethylamine hydrochloride (280 mg) and triethylamine (0.48 mL) were added. After 5 h the reaction mixture was diluted with ethyl acetate, washed with water, dried (MgSO$_4$) and the solvent was removed in vacuo to yield 4-dimethylcarbamoyl-piperidine-1-carboxylic acid tert-butyl ester. Removal of the BOC group with HCl yielded the desired compound, which was isolated as the hydrochloride salt.

$^1$H NMR (400 MHz, CDCl$_3$): 1.72 (2H, m), 1.98 (2H, m), 2.20 (2H, t), 2.55 (1H, m), 2.97 (3H, s), 3.00-3.10 (5H, m), 3.86 (2H, s), 3.94 (4H, m), 4.10 (4H, m), 7.36 (1H, s), 7.50 (1H, t, J=7.7 Hz), 7.60 (1H, d, J=8.2 Hz), 8.28 (1H, d, J=7.3 Hz); 9.02 (1H, s); 10.15 (1H, br s); MS (ESI$^+$) 506 (MH$^+$).

2-(1H-Indazol-4-yl)-4-morpholin-4-yl-6-(4-pyridin-3-ylmethyl-piperazin-1-ylmethyl)-thieno[3,2-d]pyrimidine (101)

Prepared via 2-Chloro-4-morpholin-4-yl-6-(4-pyridin-3-ylmethyl-piperazin-1-ylmethyl)-thieno[3,2-d]pyrimidine, prepared from 1-pyridin-3-ylmethyl-piperazine. The amine was prepared as described for compound 95.

$^1$H NMR (400 MHz, CDCl$_3$): 2.50-2.65 (m, 8H), 3.55 (s, 2H), 3.85 (s, 2H), 3.90-3.93 (m, 4H), 4.07-4.10 (m, 4H), 7.24 (m, 1H), 7.36 (s, 1H), 7.49 (t, 1H), 7.57 (d, 1H), 7.66 (d, 1H), 8.27 (d, 1H), 8.50 (d, 1H), 8.54 (s, 1H), 9.0 (s, 1H), 10.1 (sbr, H, NH); MS (ESI$^+$) 527.25 (MH$^+$).

1-[2-(1H-Indazol-4-yl)-4-morpholin-4-yl-thieno[3,2-d]pyrimidin-6-ylmethyl]-piperidine-4-carboxylic acid methylamide (102)

Prepared via 1-(2-Chloro-4-morpholin-4-yl-thieno[3,2-d]pyrimidin-6-ylmethyl)-piperidine-4-carboxylic acid methylamide, prepared from piperidine-4-carboxylic acid methylamide. The amine was prepared as described for compound 100.

$^1$H NMR (400 MHz, d$_6$-DMSO): 1.58-1.70 (4H, m), 2.00-2.15 (3H, m), 2.57 (3H, d, J=4.5 Hz), 2.94 (2H, m), 3.84 (6H, m), 4.00 (4H, m), 7.46 (2H, t), 7.65 (2H, d), 8.20 (1H, d), 8.87 (1H, s); 13.14 (1H, s); MS (ESI$^+$) 492 (MH$^+$).

2-{4-[2-(1H-Indazol-4-yl)-4-morpholin-4-yl-thieno[3,2-d]pyrimidin-6-ylmethyl]-piperazin-1-yl}-N-methyl-isobutyramide (103)

Prepared via 2-[4-(2-Chloro-4-morpholin-4-yl-thieno[3,2-d]pyrimidin-6-ylmethyl)-piperazin-1-yl]-N-methyl-isobutyramide, prepared from N-methyl-2-piperazin-1-yl-isobutyramide.

Amine preparation: to a mixture of DCM (10 mL), aqueous sodium bicarbonate (2M, 10 mL), and aqueous sodium carbonate (2M, 10 mL) was added methylamine hydrochloride (300 mg) at 0° C. To this was added 2-bromoisobutyryl bromide (0.50 mL) with vigorous stirring. After 2 h agitation, standard work up yielded 2-bromo-2, N-dimethyl-propionamide (548 mg) as an off-white solid.

A mixture of 2-bromo-2, N-dimethyl-propionamide (312 mg), 1-BOC-piperazine (323 mg) and silver oxide (800 mg) was stirred in toluene (5 mL) at reflux. After 24 h the reaction mixture was cooled, filtered through celite, diluted with chloroform, washed with brine, dried (MgSO$_4$) and the solvent was removed in vacuo to yield 4-(1-methyl-1-methylcarbamoyl-ethyl)-piperazine-1-carboxylic acid tert-butyl ester (461 mg). Removal of the BOC group with HCl yielded the desired compound, which was isolated as the hydrochloride salt.

$^1$H NMR (400 MHz, CDCl$_3$): 10.1 (1H, br s), 9.02 (1H, s), 8.30 (1H, d), 7.60 (1H, d), 7.51-7.49 (1H, m), 7.39 (1H, s), 7.20 (1H, q), 4.12-4.09 (4H, m), 3.95-3.90 (4H, m), 3.87 (2H, s), 2.80 (3H, d), 2.65-2.50 (8H, m), 1.21 (6H, s); MS (ESI$^+$) 535 (MH$^+$).

2-{4-[2-(1H-Indazol-4-yl)-4-morpholin-4-yl-thieno[3,2-d]pyrimidin-6-ylmethyl]-piperazin-1-yl}-2-methyl-1-pyrrolidin-1-yl-propan-1-one (104)

Prepared via 2-[4-(2-Chloro-4-morpholin-4-yl-thieno[3,2-d]pyrimidin-6-ylmethyl)-piperazin-1-yl]-2-methyl-1-pyrrolidin-1-yl-propan-1-one, prepared from 2-methyl-2-piperazin-1-yl-1-pyrrolidin-1-yl-propan-1-one.

Amine preparation: to pyrrolidine (390 uL) in dry THF (4 mL) at 0° C. was added nBuLi (1.86 ml) The reaction mixture was stirred for 5 minutes and then 4-(1-ethoxycarbonyl-1-methyl-ethyl)-piperazine-1-carboxylic acid tert-butyl ester (700 mg) in THF (5 mL) was added. The reaction mixture was stirred at room temperature for 24 h and then quenched with aqueous ammonium chloride, extracted into DCM, washed with water, dried (MgSO$_4$) and the solvent removed in vacuo to yield 4-(1,1-dimethyl-2-oxo-2-pyrrolidin-1-yl-ethyl)-piperazine-1-carboxylic acid tert-butyl ester (745 mg). Removal of the BOC group with HCl yielded the desired compound, which was isolated as the hydrochloride salt.

$^1$H NMR (400 MHz, CDCl$_3$): 1.24 (6H, s), 1.79-1.92 (4H, m), 2.52-2.66 (8H, br), 3.49 (2H, t), 3.82 (2H, s), 3.92 (4H, t), 4.00 (2H, t), 4.05 (4H, t), 7.35 (1H, s), 7.51 (1H, t), 7.59 (1H, d), 8.29 (1H, d), 9.03 (1H, s), 10.10 (1H, br); MS (ESI$^+$) 575 (MH$^+$).

2-(1H-Indazol-4-yl)-6-[4-(1-methyl-1H-imidazol-2-ylmethyl)-piperazin-1-ylmethyl]-4-morpholin-4-yl-thieno[3,2-d]pyrimidine (105)

Prepared via 2-chloro-6-[4-(1-methyl-1H-imidazol-2-ylmethyl)-piperazin-1-ylmethyl]-4-morpholin-4-yl-thieno[3,2-d]pyrimidine, prepared from 1-(1-methyl-1H-imidazol-2-ylmethyl)-piperazine. The amine was prepared as described for compound 95.

$^1$H NMR (400 MHz, CDCl$_3$): 2.50-2.65 (8H, br), 3.63 (2H, s), 3.71 (3H, s), 3.85 (2H, s), 3.92 (4H, t), 4.05 (4H, t), 6.85 (1H, s), 6.92 (1H, s), 7.38 (1H, s), 7.51 (1H, t), 7.60 (1H, d), 8.29 (1H, d), 9.02 (1H, s); MS (ESI$^+$) 530 (MH$^+$).

2-(1H-Indazol-4-yl)-6-[4-(5-methyl-isoxazol-3-yl-methol)-piperazin-1-ylmethyl]-4-morpholin-4-yl-thieno[3,2-d]pyrimidine (106)

Prepared via 2-Chloro-6-[4-(5-methyl-isoxazol-3-ylmethyl)-piperazin-1-ylmethyl]-4-morpholin-4-yl-thieno[3,2-d]pyrimidine, prepared from 1-(5-methyl-isoxazol-3-ylmethyl)-piperazine.

Amine preparation: To a suspension of lithium aluminium hydride (1.04 g) in THF (10 mL) was added methyl 5-methylisoxazole-3-carboxylate (1.00 g) as a solution in THF (10 mL). After 24 h the reaction mixture was quenched with aqueous ammonium chloride, extracted into ethyl acetate, dried (MgSO$_4$) and the solvent was removed in vacuo to yield (5-methyl-isoxazol-3-yl)-MeOH (579 mg).

To a solution of (5-methyl-isoxazol-3-yl)-MeOH (570 mg) in DCM (15 mL) was added triethylamine (0.98 mL) followed by methanesulfonyl chloride (0.51 mL). After 1 h the reaction mixture was diluted with DCM, washed with water, dried (MgSO$_4$) and the solvent was removed in vacuo to yield methanesulfonic acid 5-methyl-isoxazol-3-ylmethyl ester (887 mg).

To a solution of N-BOC-piperazine (300 mg) in MeCN (5 mL) was added potassium carbonate (289 mg) followed by methanesulfonic acid 5-methyl-isoxazol-3-ylmethyl ester (369 mg). The reaction mixture was heated to reflux for 24 h. After cooling the reaction mixture was diluted with water, extracted into ethyl acetate, dried (MgSO$_4$) and the solvent was removed in vacuo to yield 4-(5-methyl-isoxazol-3-ylmethyl)-piperazine-1-carboxylic acid tert-butyl ester (404 mg).

Removal of the BOC group with HCl yielded the desired compound, which was isolated as the hydrochloride salt.

$^1$H NMR (400 MHz, CDCl$_3$): 2.41 (s, 3H), 2.59 (br s, 8H), 3.59 (s, 2H), 3.85 (s, 2H), 3.92 (t, 4H), 4.09 (t, 4H), 5.99 (s, 1H), 7.37 (s, 1H), 7.50 (t, 1H), 7.58 (d, 1H), 8.28 (d, 1H), 9.02 (s, 1H), 10.15 (br s, 1H); MS (ESI$^+$) 531 (MH$^+$).

1-{4-[2-(1H-Indazol-4-yl)-4-morpholin-4-yl-thieno[3,2-d]pyrimidin-6-ylmethyl]-piperazin-1-yl}-2-methyl-propan-2-ol (107)

Prepared via 1-[4-(2-Chloro-4-morpholin-4-yl-thieno[3,2-d]pyrimidin-6-ylmethyl)-piperazin-1-yl]-2-methyl-propan-2-ol, prepared from 2-methyl-1-piperazin-1-yl-propan-2-ol.

Amine preparation: a mixture of 1-benzylpiperazine (5 g), ethyl bromoacetate (3.15 mL) and potassium carbonate (4.31 g) was stirred at room temperature in MeCN (50 mL). After stirring overnight the reaction mixture was diluted with chloroform, washed with brine, dried (MgSO$_4$) and the solvent removed in vacuo to yield 4-ethoxycarbonylmethyl-piperazine-1-carboxylic acid tert-butyl ester (5.86 g)

To 4-ethoxycarbonylmethyl-piperazine-1-carboxylic acid tert-butyl ester (1.0 g) in dry THF (10 mL) at 0° C. was added methyl magnesium bromide (3.0M solution in diethyl ether, 8.6 mL). The reaction mixture was then heated to reflux for 24 h. The reaction mixture was poured into ice/water/brine and then extracted into ethyl acetate, dried (MgSO$_4$) and the solvent removed in vacuo to yield 4-(2-hydroxy-2-methyl-propyl)-piperazine-1-carboxylic acid tert-butyl ester. Transfer hydrogenation with ammonium formate and 10% palladium on carbon in MeOH afforded the desired compound.

$^1$H NMR (400 MHz, CDCl$_3$): 1.17 (6H, s), 2.36 (2H, s), 2.62 (4H, m), 2.73 (4H, m), 3.86 (2H, s), 3.92 (4H, m), 4.1 (4H, m), 7.38 (1H, s), 7.50 (1H, t), 7.58 (1H, d), 8.28 (1H, d), 9.02 (1H, s); MS (ESI$^+$) 508 (MH$^+$).

Cyclopropylmethyl-{1-[2-(1H-indazol-4-yl)-4-morpholin-4-yl-thieno[3,2-d]pyrimidin-6-ylmethyl]-piperidin-4-yl}-(2-methoxy-ethyl)-amine (108)

Prepared via [1-(2-Chloro-4-morpholin-4-yl-thieno[3,2-d]pyrimidin-6-ylmethyl)-piperidin-4-yl]-cyclopropylmethyl-(2-methoxy-ethyl)-amine, prepared from cyclopropylmethyl-(2-methoxy-ethyl)-piperidin-4-yl-amine.

Amine preparation: 1-BOC-4-piperidone (500 mg) and 2-methoxyethylamine 218 µL) were stirred in MeOH at room temperature. After 16 h, sodium borohydride was added (190 mg) carefully. After a further 3 h, the reaction mixture was diluted with DCM, washed with water, dried (MgSO$_4$) and the solvent removed in vacuo to yield 4-(2-methoxy-ethylamino)-piperidine-1-carboxylic acid tert-butyl ester (560 mg).

A mixture of 4-(2-methoxy-ethylamino)-piperidine-1-carboxylic acid tert-butyl ester (525 mg), cyclopropylmethyl bromide (218 µL) and potassium carbonate (340 mg) was heated to reflux in MeCN for 16 h. After cooling the reaction mixture was diluted with chloroform, washed with brine, dried (MgSO$_4$) and the solvent removed in vacuo to yield 4-[cyclopropylmethyl-(2-methoxy-ethyl)-amino]-piperidine-1-carboxylic acid tert-butyl ester (475 mg). Removal of the BOC group with HCl yielded the desired compound, which was isolated as the hydrochloride salt.

$^1$H NMR (400 MHz, CDCl$_3$): −0.01-0.01 (2H, m), 0.40-0.48 (2H, m), 1.45-1.60 (3H, m), 1.62-1.70 (2H, m), 1.97-2.04 (2H, m), 2.33 (2H, d), 2.52-2.61 (1H, m), 2.67 (2H, t), 2.92-3.00 (2H, m), 3.25 (3H, s), 3.34 (2H, t), 3.71 (2H, s), 3.82 (4H, t), 4.00 (4H, t), 7.22 (1H, s), 7.49 (1H, t), 7.48 (1H, d), 8.28 (1H, d), 8.90 (1H, s), 10.00 (1H, br); MS (ESI$^+$) 562 (MH$^+$).

6-[4-(1-Ethyl-1-methoxymethyl-propyl)-piperazin-1-ylmethyl]-2-(1H-indazol-4-yl)-4-morpholin-4-yl-thieno[3,2-d]pyrimidine (109)

Prepared via 2-Chloro-6-[4-(1-ethyl-1-methoxymethyl-propyl)-piperazin-1-ylmethyl]-4-morpholin-4-yl-thieno[3,2-d]pyrimidine, prepared from 1-(1-ethyl-1-methoxymethyl-propyl)-piperazine.

To a solution of 1-(4-benzyl-piperazin-1-yl)-2-methoxy-ethanone (2.60 g) in dry THF (30 mL) at −10° C. was added titanium isopropoxide (3.22 mL), followed by ethyl magnesium bromide (1.0M solution in THF, 22.05 mL). The reaction mixture was heated to reflux for 2 days. After cooling the reaction mixture was cooled, diluted with chloroform, washed with brine, dried (MgSO$_4$) and the solvent removed in vacuo. The residue was purified using flash chromatography to yield 1-benzyl-4-(1-methoxymethyl-cyclopropyl)-piperazine (452 mg) and 1-benzyl-4-(1-ethyl-1-methoxymethyl-propyl)-piperazine (248 mg). Transfer hydrogenation conditions using ammonium formate and 10% Pd/C in MeOH afforded the desired compound.

$^1$H NMR (400 MHz, CDCl$_3$) 0.85 (6H, t), 1.58-1.33 (4H, m), 2.55-2.50 (4H, m), 2.75-2.70 (4H, m), 3.30 (5H, s), 3.85 (2H, s), 3.95-3.91 (4H, m), 4.12-4.09 (4H, m), 7.39 (1H, s), 7.51-7.49 (1H, m), 7.60 (1H, d), 8.30 (1H, d), 9.02 (1H, s), 10.2 (1H, br s); MS (ESI$^+$) 550 (MH$^+$).

2-(1H-Indazol-4-yl)-6-[4-(1-methoxymethyl-cyclopropyl)-piperazin-1-ylmethyl]-4-morpholin-4-yl-thieno[3,2-d]pyrimidine (110)

Prepared via 2-Chloro-6-[4-(1-methoxymethyl-cyclopropyl)-piperazin-1-ylmethyl]-4-morpholin-4-yl-thieno[3,2-d]pyrimidine, prepared from 1-(1-methoxymethyl-cyclopropyl)-piperazine. Amine was prepared as outlined for compound 109.

$^1$H NMR (400 MHz, CDCl$_3$) 0.65-0.52 (4H, m), 2.55-2.50 (4H, m), 2.85-2.80 (4H, m), 3.32 (3H, s), 3.40 (2H, s), 3.85 (2H, s), 3.95-3.91 (4H, m), 4.12-4.09 (4H, m), 7.39 (1H, s), 7.51-7.49 (1H, m), 7.60 (1H, d), 8.30 (1H, d), 9.02 (1H, s), 10.2 (1H, br s); MS (ESI$^+$) 520 (MH$^+$).

111 {1-[2-(1H-Indazol-4-yl)-4-morpholin-4-yl-thieno[3,2-d]pyrimidin-6-ylmethyl]-piperidin-4-yl}-(2-methoxy-ethyl)-(2,2,2-trifluoro-ethyl)-amine Via [1-(2-Chloro-4-morpholin-4-yl-thieno[3,2-d]pyrimidin-6-ylmethyl)-piperidin-4-yl]-(2-methoxy-ethyl)-(2,2,2-trifluoro-ethyl)-amine, prepared from (2-methoxy-ethyl)-piperidin-4-yl-(2,2,2-trifluoro-ethyl)-amine.

Amine preparation: 1-BOC-4-piperidinone (2.00 g) and 2-methoxyethylamine (872 µL) were stirred together in MeOH (20 mL) at room temperature overnight. Sodium borohydride (760 mg) was then added portionwise and the reaction mixture was allowed to stir further at ambient temperature. After 16 h, the solvent was removed in vacuo, the residue was diluted with DCM, washed with brine, dried (MgSO$_4$) and the solvent removed in vacuo. The residue was purified using flash chromatography to yield 4-(2-methoxy-ethylamino)-piperidine-1-carboxylic acid tert-butyl ester as a colourless oil (1.69 g).

To a solution of 4-(2-methoxy-ethylamino)-piperidine-1-carboxylic acid tert-butyl ester (500 mg) in DCM (5 mL) and triethylamine (540 µL) was added trifluoroacetic anhydride (548 µL). The reaction mixture was stirred at room temperature overnight, diluted with DCM, washed with brine, dried (MgSO$_4$) and the solvent removed in vacuo. The residue was purified using flash chromatography to yield 4-[(2-methoxy-ethyl)-(2,2,2-trifluoro-acetyl)-amino]-piperidine-1-carboxylic acid tert-butyl ester as an oil (685 mg).

To a solution of 4-[(2-methoxy-ethyl)-(2,2,2-trifluoro-acetyl)-amino]-piperidine-1-carboxylic acid tert-butyl ester (685 mg) in dry THF (7 mL) was added borane-methyl sulfide complex (405 uL) at 0° C. under inert atmosphere. The reaction mixture was refluxed for 3 h, and then stirred at room temperature overnight, quenched with MeOH, diluted with DCM, washed with brine, dried (MgSO$_4$) and the solvent removed in vacuo. The residue was purified using flash chromatography to yield 4-[(2-methoxy-ethyl)-(2,2,2-trifluoro-ethyl)-amino]-piperidine-1-carboxylic acid tert-butyl ester as an oil (635 mg). Treatment of this compound with HCl in DCM/MeOH furnished the desired amine, isolated as the hydrochloride salt.

$^1$H NMR (400 MHz, CDCl$_3$) 1.55-1.64 (2H, m), 1.76-1.82 (2H, m), 2.12-2.18 (2H, m), 2.58-2.62 (1H, m), 2.86 (2H, t, J=6.3 Hz), 3.03-3.08 (2H, m), 3.20 (2H, q, J=9.4 Hz), 3.33 (3H, s), 3.45 (2H, t, J=6.4 Hz), 3.84 (2H, s), 4.00 (4H, t, J=5.1 Hz), 7.22 (1H, s), 7.49 (1H, t, J=7.2 Hz), 7.48 (1H, d, J=8.3 Hz), 8.28 (1H, d, J=7.1 Hz), 8.90 (1H, s), 10.00 (1H, br); MS (ESI$^+$) 590 (MH$^+$).

121 2-(1H-Indazol-4-yl)-6-[4-(2-methoxy-ethyl)-piperazin-1-ylmethyl]-4-morpholin-4-yl-thieno[3,2-d]pyrimidine Via 2-Chloro-6-[4-(2-methoxy-ethyl)-piperazin-1-ylmethyl]-4-morpholin-4-yl-thieno[3,2-d]pyrimidine, prepared from 1-(2-methoxy-ethyl)-piperazine.

$^1$H NMR (400 MHz, CDCl$_3$) 2.55-2.70 (m, 10H, 5×CH$_2$), 3.35 (s, 2H, CH$_2$), 3.50-3.53 (m, 2H, CH$_2$), 3.85 (s, 2H, CH$_2$), 3.90-3.93 (m, 4H, 2×CH$_2$), 4.07-4.11 m, 4H, 2×CH$_2$), 7.37 (s, H, ArH), 7.49 (t, H, ArH, J=7.76 Hz), 7.57 (d, H, ArH, J=8.3 Hz), 8.27 (d, H, ArH, J=6.71 Hz), 9.0 (s, H, ArH), 10.15 (br s, H, NH). MS (ESI$^+$) 494.18 (MH$^+$).

122 2-{4-[2-(1H-Indazol-4-yl)-4-morpholin-4-yl-thieno[3,2-d]pyrimidin-6-ylmethyl]-piperazin-1-yl}-isobutyramide Via 2-[4-(2-Chloro-4-morpholin-4-yl-thieno[3,2-d]pyrimidin-6-ylmethyl)-piperazin-1-yl]-isobutyramide, prepared from 2-piperazin-1-yl-isobutyramide.

Amine preparation: a mixture of 1-BOC-piperazine (1.063 g), DCM/MeOH (20 mL) and 2.0M HCl in ether (3.14 mL) was stirred at 0° C. After 1 hr the solvent was removed in vacuo to yield a white solid. This was dissolved in water and sodium cyanide (280 mg) was added. To this was added a solution of acetone (420 µL) in water 2 mL. After stirring for 48 hrs the reaction mixture was dissolved in ethyl acetate, washed with brine, dried (MgSO$_4$) and the solvent removed in vacuo to yield 4-(cyano-dimethyl-methyl)-piperazine-1-carboxylic acid tert-butyl ester (1.11 g).

To a cooled (ice/water bath) solution of 4-(cyano-dimethyl-methyl)-piperazine-1-carboxylic acid tert-butyl ester (102.9 mg) in dry DMSO was added K$_2$CO$_3$ (9.8 mg) followed by 28% hydrogen peroxide solution (200 µL) dropwise. The resultant was heated at 40° C. overnight. Water was added and the white solid collected, washed with water and air dried to give 4-(1-carbamoyl-1-methyl-ethyl)-piperazine-1-carboxylic acid tert-butyl ester (59.6 mg). (See *Tetrahedron* 2002, 58, 3217). Treatment of this compound with HCl in DCM/MeOH yielded the desired amine, which was isolated as the hydrochloride salt.

$^1$H NMR (400 MHz, CDCl$_3$) 1.24 (s, 6H, 2×CH$_2$), 2.55-2.65 (m, 8H, 4×CH$_2$), 3.85 (s, 2H, CH$_2$), 3.90-3.92 (m, 4H, 2×CH$_2$), 4.07-4.09 (m, 4H, 2×CH$_2$), 5.35 (m, H, NH), 7.09 (m, H, NH), 7.37 (s, H, ArH), 7.48 (t. H, ArH, J=7.72 Hz), 7.57 (d, H, ArH, J=8.22 Hz), 8.26 (d, H, ArH, J=7.14 Hz), 9.0 (s, H, ArH, 10.4 (br s, H, NH). MS (ESI$^+$) 521.27 (MH$^+$).

123 {1-[2-(1H-Indazol-4-yl)-4-morpholin-4-yl-thieno[3,2-d]pyrimidin-6-ylmethyl]-piperidin-4-yl}-methanol Via [1-(2-Chloro-4-morpholin-4-yl-thieno[3,2-d]pyrimidin-6-ylmethyl)-piperidin-4-yl]-methanol, prepared from piperidin-4-yl-methanol.

Amine preparation: To a solution of piperidine-4-carboxylic acid ethyl ester (5.0 g) stirring in dry MeCN (70 mL) was added triethylamine (5.3 mL), followed by di-tertiary-butyl dicarbonate (7.64 g). The reaction mixture was stirred at room temperature for 24 h, then diluted with water (150 mL) extracted into ethyl acetate, dried (MgSO$_4$) and the solvent removed in vacuo. The residue was purified using flash chromatography to give 1-BOC-piperidine-4-ethyl ester (6.8 g) as a colourless oil. To a suspension of lithium aluminium hydride powder (300 mg) stirring in dry THF (100 mL) under a nitrogen atmosphere was added 1-BOC-piperidine-4-ethyl ester dissolved in dry THF (5 mL). The reaction mixture was stirred at room temperature. After 2 h the reaction mixture was quenched with saturated ammonium chloride solution (10 mL), filtered through a celite bed and the solvent removed in vacuo to yield 4-hydroxymethyl-piperidine-1-carboxylic acid tert-butyl ester (0.793 g) as a pale yellow solid. Treatment with TFA yielded the desired amine, which was isolated as the TFA salt.

$^1$H NMR (400 MHz, d$_6$-DMSO) 1.18 (m, 2H), 1.37 (m, 1H), 1.64 (m, 2H), 2.04 (t, 2H), 2.92 (m, 2H), 3.27 (m, 2H), 3.82 (m, 4H & CH$_2$), 3.99 (m, 4H), 4.39 (t, 1H), 7.45 (t, 2H), 7.65 (d, 1H, J=8.2 Hz), 8.21 (d, 1H, J=7.3 Hz), 8.87 (s, 1H), 13.16 (br s, 1H); MS (ESI$^+$) 465.17 (MH$^+$).

124 2-(1H-Indazol-4-yl)-4-morpholin-4-yl-6-(4-pyridin-4-ylmethyl-piperazin-1-ylmethyl)-thieno[3,2-d]pyrimidine Via 2-Chloro-4-morpholin-4-yl-6-(4-pyridin-4-ylmethyl-piperazin-1-ylmethyl)-thieno[3,2-d]pyrimidine, prepared from 1-pyridin-4-ylmethyl-piperazine.

Amine preparation: a mixture of 1-BOC-piperazine (2 g), 4-pyridine carboxaldehyde (1.26 g), sodium triacetoxyborohydride (2.96 g) and acetic acid (0.6 mL) was stirred together in dry 1,2-dichloroethane (15 mL) at room temperature. After 4 h the reaction was quenched with saturated NaHCO$_3$ solution and extracted with DCM, dried (Na$_2$SO$_4$), filtered and concentrated in vacuo to give 4-pyridin-4-ylmethyl-piperazine-1-carboxylic acid tert-butyl ester (3 g). Treatment of this compound with HCl in DCM/MeOH yielded the desired amine, which was isolated as the hydrochloride salt.

$^1$H NMR (400 MHz, CDCl$_3$) 2.40-2.60 (m, 8H, 4×CH$_2$), 3.45 (s, 2H, CH$_2$), 3.78 (s, 2H, CH$_2$), 3.82-3.84 (m, 4H, 2×CH$_2$), 3.99-4.01 (m, 4H, 2×CH$_2$), 7.18-7.19 (m, 2H, 2×ArH), 7.30 (s, H, ArH), 7.39 (t, H, ArH, J=7.7 Hz), 7.47 (d, H, ArH, J=8.55 Hz), 8.18 (d, H, ArH, J=7.17 Hz), 8.46 (d, H, ArH, J=5.34 Hz), 8.93 (s, H, ArH), 10.25 (br s, H, NH); MS (ESI$^+$) 527.29 (MH$^+$).

125 2-(1H-Indazol-4-yl)-6-[4-(6-methyl-pyridin-2-ylmethyl)-piperazin-1-ylmethyl]-4-morpholin-4-yl-thieno[3,2-d]pyrimidine Via 2-chloro-6-[4-(6-methyl-pyridin-2-ylmethyl)-piperazin-1-ylmethyl]-4-morpholin-4-yl-thieno[3,2-d]pyrimidine, prepared from 1-(6-methyl-pyridin-2-ylmethyl)-piperazine. The amine, 1-(6-methyl-pyridin-2-ylmethyl)-piperazine, was prepared using 6-methyl-2-pyridinecarboxaldehyde, analogous to 124.

$^1$H NMR (400 MHz, CDCl$_3$) 2.54 (s, 3H, CH$_3$), 2.60-2.70 (m, 8H, 4×CH$_2$), 3.67 (s, 2H, CH$_2$), 3.86 (s, 2H, CH$_2$), 3.90-3.93 (m, 4H, 2×CH$_2$), 4.07-4.10 (m, 4H, 2×CH$_2$), 7.00 (d, H, ArH, J=7.6 Hz), 7.22-7.25 (m, H, ArH part under CDCl$_3$), 7.36 (s, H, ArH), 7.47-7.57 (m, 3H, 3×ArH), 8.27 (d, H, ArH, J=7.2 Hz), 9.00 (s, H, ArH), 10.2 (br s, H, NH); MS (ESI$^+$) 541.24 (MH$^+$).

126 2-(1H-Indazol-4-yl)-6-[4-(4-methyl-thiazol-2-ylmethyl)-piperazin-1-ylmethyl]-4-morpholin-4-yl-thieno[3,2-d]pyrimidine Via 2-chloro-6-[4-(4-methyl-thiazol-2-ylmethyl)-piperazin-1-ylmethyl]-4-morpholin-4-yl-thieno[3,2-d]pyrimidine, prepared from 1-(4-methyl-thiazol-2-ylmethyl)-piperazine. The amine, 1-(4-methyl-thiazol-2-ylmethyl)-piperazine, was prepared using 4-methylthiazole-2-carboxaldehyde, analogous to 125.

$^1$H NMR (400 MHz, CDCl$_3$) 2.43 (s, 3H), (br s, 8H), 3.85 (m, 4H), 3.92 (m, 4H), 4.09 (m, 4H), 6.83 (s, 1H), 7.38 (s, 1H), 7.51 (m, 1H), 7.60 (d, J=8.3 Hz, 1H), 8.28 (d, J=6.8 Hz, 1H), 9.02 (s, 1H); MS (ESI$^+$) 547 (MH$^+$).

127 {1-[2-(1H-Indazol-4-yl)-4-morpholin-4-yl-thieno[3,2-d]pyrimidin-6-ylmethyl]-piperidin-4-yl}-pyridin-2-yl-amine Via [1-(2-Chloro-4-morpholin-4-yl-thieno[3,2-d]pyrimidin-6-ylmethyl)-piperidin-4-yl]-pyridin-2-yl-amine, prepared from piperidin-4-yl-pyridin-2-yl-amine.

Amine preparation: A mixture of 1-BOC-4-piperidone (496 mg), 2-aminopyridine (234 mg), sodium triacetoxyborohydride (580 mg) and acetic acid (0.14 mL) was stirred together in dry 1,2-dichloroethane (100 mL) at room temperature. After 24 h the reaction was quenched with saturated NaHCO$_3$ solution and extracted with DCM, dried (Na$_2$SO$_4$), filtered and concentrated in vacuo to give 4-(pyridin-2-ylamino)-piperidine-1-carboxylic acid tert-butyl ester (135 mg) after flash chromatography. Treatment of this compound with HCl in DCM/MeOH yielded the desired amine, which was isolated as the hydrochloride salt.

$^1$H NMR (400 MHz, CDCl$_3$) 1.65-1.55 (2H, m), 2.10-2.08 (2H, m), 2.40-2.30 (2H, m), 3.01 (2H, d), 3.73-3.67 (1H, m), 3.85 (2H, s), 3.95-3.91 (4H, m), 4.12-4.09 (4H, m), 4.40 (1H, br d), 6.39 (1H, d), 6.56-6.521 (1H, m), 7.48-7.40 (2H, m), 7.51-7.49 (1H, m), 7.60 (1H, d), 8.09 (1H, d), 8.30 (1H, d), 9.02 (1H, s), 10.2 (1H, br s); MS (ESI$^+$) 527 (MH$^+$).

128 N-{1-[2-(1H-Indazol-4-yl)-4-morpholin-4-yl-thieno[3,2-d]pyrimidin-6-ylmethyl]-piperidin-4-yl}-2-methoxy-N-methyl-acetamide Via N-[1-(2-chloro-4-morpholin-4-yl-thieno[3,2-d]pyrimidin-6-ylmethyl)-piperidin-4-yl]-2-methoxy-N-methyl-acetamide, prepared from 2-methoxy-N-methyl-N-piperidin-4-yl-acetamide.

Amine preparation: To a solution of 1-BOC-4-piperidone (1.0 g) in MeOH (10 mL) was added a solution of freshly prepared methylamine in MeOH (1.0 mL). The reaction mixture was stirred for 1 h and then sodium cyanoborohydride (0.315 g) was added. After stirring for 24 h the reaction mixture was then diluted with DCM, washed with sodium bicarbonate solution, dried (MgSO$_4$) and the solvent removed in vacuo. The residue was purified by flash chromatography to yield 4-methylamino-piperidine-1-carboxylic acid tert-butyl ester (0.85 g).

To a solution of 4-methylamino-piperidine-1-carboxylic acid tert-butyl ester (0.42 g) in DCM (10 mL) was added triethylamine (0.30 mL) followed by methoxyacetyl chloride (0.20 mL). After stirring for 3 h the reaction mixture was then diluted with DCM, washed with sodium bicarbonate solution, dried (MgSO$_4$) and the solvent removed in vacuo. The residue was purified by flash chromatography to yield 4-[(2-methoxy-acetyl)-methyl-amino]-piperidine-1-carboxylic acid tert-butyl ester (0.293 g). Treatment of this compound with HCl in DCM/MeOH yielded the desired amine, which was isolated as the hydrochloride salt.

$^1$H NMR (400 MHz, CDCl$_3$) 1.66 (2H, m), 1.80+1.97 (2H, m, 2 rotamers), 2.36 (2H, m), 2.90 (3H, s), 3.08 (2H, m), 3.43 (3H, s), 3.65+4.50 (1H, m, 2 rotamers), 3.86 (2H, s), 3.94 (4H, m), 4.10 (4H, m), 7.40 (1H, s), 7.51 (1H, t, J=7.7 Hz), 7.54 (1H, d, J=8.2 Hz), 8.28 (1H, d, J=7.2 Hz), 9.02 (1H, s), 10.18 (1H, br s); MS (ESI$^+$) 536 (MH$^+$).

129 N-{1-[2-(1H-Indazol-4-yl)-4-morpholin-4-yl-thieno[3,2-d]pyrimidin-6-ylmethyl]-piperidin-4-yl}-N-methyl-methanesulfonamide Via N-[1-(2-chloro-4-morpholin-4-yl-thieno[3,2-d]pyrimidin-6-ylmethyl)-piperidin-4-yl]-N-methyl-methanesulfonamide, prepared from N-methyl-N-piperidin-4-yl-methanesulfonamide. The amine, N-methyl-N-piperidin-4-yl-methanesulfonamide, was prepared by treatment of 4-methylamino-piperidine-1-carboxylic acid tert-butyl ester with methanesulfonyl chloride, analogous to 128.

$^1$H NMR (400 MHz, CDCl$_3$) 1.72 (2H, m), 1.90 (2H, m), 2.23 (2H, t, J=11.0 Hz), 2.85 (6H, s), 3.08 (2H, br d, J=11.4 Hz), 3.80 (1H, m), 3.86 (2H, s), 3.94 (4H, m), 4.10 (4H, m), 7.39 (1H, s), 7.52 (1H, t, J=7.7 Hz), 7.60 (1H, d, J=8.0 Hz), 8.29 (1H, d, J=7.1 Hz), 9.03 (1H, s), 10.15 (1H, br s); MS (ESI$^+$) 542 (MH$^+$).

130 {1-[2-(1H-Indazol-4-yl)-4-morpholin-4-yl-thieno[3,2-d]pyrimidin-6-ylmethyl]-piperidin-4-yl}-(3-methoxy-propyl)-methyl-amine Via [1-(2-chloro-4-morpholin-4-yl-thieno[3,2-d]pyrimidin-6-ylmethyl)-piperidin-4-yl]-(3-methoxy-propyl)-methyl-amine, prepared from (3-methoxy-propyl)-methyl-piperidin-4-yl-amine. The amine, (3-methoxy-propyl)-methyl-piperidin-4-yl-amine, was prepared from 4-methylamino-piperidine-1-carboxylic acid tert-butyl ester and toluene-4-sulfonic acid 3-methoxy-propyl ester (produced from 3-methoxy-1-propanol using standard conditions) in a similar manner to 128.

$^1$H NMR (400 MHz, CDCl$_3$) 1.55-1.85 (6H, 3×CH$_2$), 2.11 (m, 2H, CH$_2$), 2.31 (s, 3H, CH$_3$), 2.44 (m, H, CH), 2.57 (m, 2H, CH$_2$), 3.05 (m, 2H, CH$_2$), 3.33 (s, 3H, CH$_3$), 3.42 (m, 2H, CH$_2$), 3.83 (s, 2H, CH$_2$), 3.91-3.93 (m, 4H, 2×CH$_2$), 4.08-4.10 (m, 4H, 2×CH$_2$), 7.35 (s, H, ArH), 7.50 (t, H, ArH, J=7.77 Hz), 7.58 (d, H, ArH, J=8.27 Hz), 8.26 (d, H, ArH, J=6.77 Hz), 9.00 (s, H, ArH), 10.23 (s br, H, NH); MS (ESI$^+$) 536.46 (MH$^+$).

131 6-((3S,5R)-3,5-Dimethyl-4-pyridin-2-ylmethyl-piperazin-1-ylmethyl)-2-(1H-indazol-4-yl)-4-morpholin-4-yl-thieno[3,2-d]pyrimidine Via 2-Chloro-6-((3S,5R)-3,5-dimethyl-4-pyridin-2-ylmethyl-piperazin-1-ylmethyl)-4-morpholin-4-yl-thieno[3,2-d]pyrimidine, prepared from (2S,6R)-2,6-dimethyl-1-pyridin-2-ylmethyl-piperazine. Amine preparation: (3R,5S)-3,5-dimethyl-piperazine-1-carboxylic acid tert-butyl ester (845 mg), 2-(bromomethyl)-pyridine hydrobromide (1 g) and potassium carbonate (1.15 g) was heated to reflux in MeCN (10 mL). After heating for 24 h the reaction mixture was diluted with DCM, washed with sodium bicarbonate solution, dried (MgSO$_4$) and the solvent removed in vacuo. The residue was purified by flash chromatography to yield (3S,5R)-3,5-dimethyl-4-pyridin-2-ylmethyl-piperazine-1-carboxylic acid tert-butyl ester (867 mg). Treatment of this compound with HCl in DCM/MeOH yielded the desired amine, which was isolated as the hydrochloride salt.

$^1$H NMR (400 MHz, CDCl$_3$) 1.00 (d, J=6.0 Hz, 6H), 1.54 (s, 2H), 2.05 (m, 2H), 2.84 (m, 4H), 3.81 (s, 2H), 3.92 (m, 4H), 4.10 (m, 4H), 7.11 (m, 1H), 7.38 (s, 1H), 7.51 (m, 1H), 7.61 (m, 3H), 8.29 (d, J=7.4 Hz, 1H), 8.51 (d, J=4.5 Hz, 1H), 9.03 (s, 1H); MS (ESI$^+$) 555 (MH$^+$).

132 2-(1H-Indazol-4-yl)-6-(4-methoxymethyl-piperidin-1-ylmethyl)-4-morpholin-4-yl-thieno[3,2-d]pyrimidine Via 2-Chloro-6-(4-methoxymethyl-piperidin-1-ylmethyl)-4-morpholin-4-yl-thieno[3,2-d]pyrimidine, prepared from 4-methoxymethyl-piperidine. Amine preparation: To a solution of 4-hydroxymethyl-piperidine-1-carboxylic acid tert-butyl ester (212 mg) stirring in dry THF (10 mL) under a nitrogen atmosphere was added sodium hydride (60% in paraffin oil; 45 mg) followed after 20 min by methyl iodide and the reaction mixture was warmed to 70° C. After 4 h the mixture was cooled and quenched with water (10 mL) extracted into ethyl acetate, and dried (MgSO4). The residue was purified using flash chromatography to yield 4-methoxy-piperidine-1-carboxylic acid tert-butyl ester (158 mg) as a colourless oil. Treatment with TFA yielded the desired amine which was isolated as the TFA salt.

$^1$H NMR (400 MHz, CDCl$_3$) 1.23 (m, 2H), 1.54 (m, 1H), 1.63 (m, 2H), 2.05 (m, 2H), 2.91 (m, 2H), 3.18 (d, 2H, J=6.2 Hz), 3.22 (s, 3H), 3.82 (m, 4H, +CH$_2$), 3.99 (m, 4H), 7.45 (t, 2H, J=7.0 Hz), 7.65 (d, 1H, J=8.2 Hz), 8.21 (d, 1H, J=7.1 Hz), 8.87 (s, 1H), 13.16 (br s, 1H); MS (ESI$^+$) 479.2 (MH$^+$).

133 {1-[2-(1H-Indazol-4-yl)-4-morpholin-4-yl-thieno[3,2-d]pyrimidin-6-ylmethyl]-piperidin-4-yl}-(2-methoxy-ethyl)-thiazol-2-ylmethyl-amine Via [1-(2-chloro-4-morpholin-4-yl-thieno[3,2-d]pyrimidin-6-ylmethyl)-piperidin-4-yl]-(2-methoxy-ethyl)-thiazol-2-ylmethyl-amine, prepared from (2-methoxy-ethyl)-piperidin-4-yl-thiazol-2-ylmethyl-amine.

Amine preparation: 4-(2-Methoxy-ethylamino)-piperidine-1-carboxylic acid tert-butyl ester (465 mg) and 2-thiazolecarboxaldehyde (190 ul) were stirred in dry 1,2-dichloroethane (5 mL) for 1 h. Next were added acetic acid (1 eq.) and sodium triacetoxyborohydride (458 mg). The reaction mixture was stirred at room temperature overnight, diluted with DCM, washed with brine, dried (MgSO$_4$) and the solvent removed in vacuo. The residue was purified using flash chromatography to yield 4-[(2-methoxy-ethyl)-thiazol-2-ylmethyl-amino]-piperidine-1-carboxylic acid tert-butyl ester (574 mg). Treatment of this compound with HCl in DCM/MeOH and basic wash with sodium hydrogen carbonate yielded the desired amine.

$^1$H NMR (400 MHz, CDCl$_3$) 1.62-1.73 (2H, m), 1.81-1.88 (2H, m), 2.06-2.14 (2H, m), 2.60-2.68 (1H, m), 2.88 (2H, t, J=6.4 Hz), 3.02-3.08 (2H, m), 3.30 (3H, s), 3.49 (2H, t, J=6.4 Hz), 3.82 (2H, s), 3.92-3.96 (4H, m), 4.10 (2H, s), 4.10-4.14 (4H, m), 7.22 (1H, d, J=3.2), 7.35 (1H, s), 7.51 (1H, t, J=8.0 Hz), 7.59 (1H, d, J=8.3), 7.72 (1H, d, J=3.2), 8.29 (1H, d, J=6.6 Hz), 9.03 (1H, s), 10.10 (1H, br); MS (ESI$^+$) 605 (MH$^+$).

134 1-[2-(1H-Indazol-4-yl)-4-morpholin-4-yl-thieno[3,2-d]pyrimidin-6-ylmethyl]-4-pyridin-2-ylmethyl-piperidin-4-ol Via 1-(2-chloro-4-morpholin-4-yl-thieno[3,2-d]pyrimidin-6-ylmethyl)-pyridin-2-ylmethyl-piperidin-4-ol, prepared from 4-pyridin-2-ylmethyl-piperidin-4-ol.

Amine preparation: To a solution of 2-picoline (333 mg) in dry THF (5 mL) at −78° C. was added nBuLi (2.5M solution in hexanes, 1.50 mL). The reaction mixture was warmed to room temperature over 30 min and then cooled to −78° C. 1-BOC-4-piperidone (713 mg) was then added, and the reaction mixture was raised to 0° C. over 20 min. The reaction mixture was stirred overnight and then quenched with water.

The organics were extracted into ethyl acetate, dried (MgSO$_4$), filtered and concentrated in vacuo to give crude product. The residue was purified using flash chromatography to yield 4-hydroxy-4-pyridin-2-ylmethyl-piperidine-1-carboxylic acid tert-butyl ester (290 mg). Treatment of this compound with HCl in DCM/MeOH yielded the desired amine, which was isolated as the hydrochloride salt.

$^1$H NMR (400 MHz, CDCl$_3$) 1.55-1.75 (4H, m), 2.55-2.61 (2H, m), 2.68-2.72 (2H, m), 2.91 (2H, s), 3.88 (2H, s), 3.91-3.94 (4H, m), 4.05-4.10 (4H, m), 5.80 (1H, s), 7.05-7.11 (2H, m), 7.37 (1H, s), 7.46-7.51 (1H, s), 7.55-7.62 (2H, m), 8.29 (1H, d), 8.50 (1H, d), 9.03 (1H, s), 10.10 (1H, br s); MS (ESI$^+$) 542 (MH$^+$).

135 {1-[2-(1H-Indazol-4-yl)-4-morpholin-4-yl-thieno[3,2-d]pyrimidin-6-ylmethyl]-piperidin-4-yl}-isopropyl-(2-methoxy-ethyl)-amine Via [1-(2-chloro-4-morpholin-4-yl-thieno[3,2-d]pyrimidin-6-ylmethyl)-piperidin-4-yl]-isopropyl-(2-methoxy-ethyl)-amine, prepared from isopropyl-(2-methoxy-ethyl)-piperidin-4-yl-amine.

Amine preparation: A mixture of 4-(2-methoxy-ethylamino)-piperidine-1-carboxylic acid tert-butyl ester (see preparation of 121) (300 mg) and 2-bromopropane (1.20 mL) in MeCN (3 mL) with potassium carbonate (192 mg) were heated at 60° C. in a sealed tube for 7 days. The reaction mixture was cooled down, diluted with DCM, washed with brine, dried (MgSO$_4$) and the solvent removed in vacuo. The residue was purified using flash chromatography to yield 4-[isopropyl-(2-methoxy-ethyl)-amino]-piperidine-1-carboxylic acid tert-butyl ester as an oil (131 mg). Treatment of this compound with HCl in DCM/MeOH and basic wash with aqueous sodium bicarbonate yielded the desired amine.

$^1$H NMR (400 MHz, CDCl$_3$) 1.03 (6H, d, J=6.6 Hz), 1.62-1.72 (4H, m), 2.08-2.14 (2H, m), 2.52-2.60 (1H, m), 2.69 (2H, t, J=7.4 Hz), 3.03-3.12 (4H, m), 3.33 (2H, t, J=7.3 Hz), 3.35 (3H, s), 3.82 (2H, s), 3.92 (4H, t, J=4.5 Hz), 4.05 (4H, t, J=4.5 Hz), 7.35 (1H, s), 7.51 (1H, t, J=8.0 Hz), 7.59 (1H, d, J=8.3 Hz), 8.29 (1H, d, J=6.6 Hz), 9.03 (1H, s), 10.10 (1H, br); MS (ESI$^+$) 550 (MH$^+$).

136 2-(1H-Indazol-4-yl)-4-morpholin-4-yl-6-[4-(pyridin-2-yloxy)-piperidin-1-ylmethyl]-thieno[3,2-d]pyrimidine Via 2-chloro-4-morpholin-4-yl-6-[4-(pyridin-2-yloxy)-piperidin-1-ylmethyl]-thieno[3,2-d]pyrimidine, prepared from 2-(piperidin-4-yloxy)-pyridine.

Amine preparation: A mixture of 1-benzyl-piperidin-4-ol (1 g), 2-chloropyridine (0.5 mL), 18-crown-6 (72 mg) and KOH (290 mg) was refluxed in dry toluene. After 18 h, the reaction mixture was diluted with water, extracted with DCM, dried (Na$_2$SO$_4$), filtered and concentrated in vacuo then purified by flash chromatography to give 4-(pyridin-2-yloxy)-piperidine-1-carboxylic acid tert-butyl ester (789 mg). Treatment of this compound with hydrogen, 10% palladium on carbon and ammonium formate in MeOH yielded the desired amine.

$^1$H NMR (400 MHz, CDCl$_3$): 1.88-1.90 (m, 2H, 2×CH), 2.04-2.08 (m, 2H, 2×CH), 3.48-2.52 (m, 2H, 2×CH), 2.85-2.90 (m, 2H, 2×CH), 3.88 (s, 2H, CH$_2$), 3.91-3.93 (m, 4H, 2×CH$_2$), 4.08-4.11 (m, 4H, 2×CH$_2$), 5.10-5.18 (m, H, CH), 6.71 (d, H, ArH, J=8.34 Hz), 6.82 (t, H, ArH, J=6.11 Hz), 7.37 (s, H, ArH), 7.47-7.58 (m, 3H, 3×ArH), 8.12 (d, H, ArH, J=5.01 Hz), 8.27 (d, H, ArH, J=6.8 Hz), 9.01 (s, H, ArH), 10.09 (br s, H, NH); MS (ESI$^+$) 528.31 (MH$^+$).

137 N-{1-[2-(1H-Indazol-4-yl)-4-morpholin-4-yl-thieno[3,2-d]pyrimidin-6-ylmethyl]-piperidin-4-yl}-N-(2-methoxy-ethyl)-methanesulfonamide Via N-[1-(2-chloro-4-morpholin-4-yl-thieno[3,2-d]pyrimidin-6-ylmethyl)-piperidin-4-yl]-N-(2-methoxy-ethyl)-methanesulfonamide, prepared from N-(2-methoxy-ethyl)-N-piperidin-4-yl-methanesulfonamide.

Amine preparation: To a solution of 4-(2-methoxyethylamine)-piperidine-1-carboxylic acid tert-butyl ester (see preparation of 121) (0.50 g) in DCM (10 mL) was added triethylamine (0.30 mL) followed by methanesulfonyl chloride (0.16 mL). After stirring for 4 h the reaction mixture was then diluted with DCM, washed with sodium bicarbonate solution, dried (MgSO$_4$) and the solvent removed in vacuo. The residue was purified by flash chromatography to yield 4-[methanesulfonyl-(2-methoxy-ethyl)-amino]-piperidine-1-carboxylic acid tert-butyl ester (0.474 g). Treatment of this compound with HCl in DCM/MeOH yielded the desired amine, which was isolated as the hydrochloride salt.

$^1$H NMR (400 MHz, CDCl$_3$) 1.78 (2H, m), 1.92 (2H, m), 2.21 (2H, t, J=10.9 Hz), 2.90 (3H, s), 3.07 (2H, br d, J=11.6 Hz), 3.38 (5H, m), 3.54 (2H, t, J=6.3 Hz), 3.68 (1H, m), 8.83 (2H, s), 3.94 (4H, m), 4.10 (4H, m), 7.38 (1H, s), 7.50 (1H, t, J=7.7 Hz), 7.60 (1H, d, J=8.2 Hz), 8.29 (1H, d, J=7.1 Hz), 9.02 (1H, s), 10.10 (1H, br s); MS (ESI$^+$) 586 (MH$^+$).

138 2-{1-[2-(1H-Indazol-4-yl)-4-morpholin-4-yl-thieno[3,2-d]pyrimidin-6-ylmethyl]-piperidin-4-yl}-propan-2-ol Via 2-[1-(2-chloro-4-morpholin-4-yl-thieno[3,2-d]pyrimidin-6-ylmethyl)-piperidin-4-yl]-propan-2-ol, prepared from 2-piperidin-4-yl-propan-2-ol.

Amine preparation: To a solution of piperidine-4-carboxylic acid ethyl ester (3.0 g) stirring in dry MeCN (30 mL) was added potassium carbonate (2.90 g) followed by benzyl bromide (2.5 mL). The mixture was warmed to 78° C. After 3 h the mixture was cooled, poured into water (100 mL) and extracted into ethyl acetate, dried (MgSO4) and the solvent removed in vacuo. The residue was purified using flash chromatography to give 1-benzyl-piperidine-4-carboxylic acid ethyl ester (2.17 g) as a pale yellow oil.

To a solution of 1-benzyl-piperidine-4-carboxylic acid ethyl ester (1.0 g) stirring in dry THF (15 mL) under a nitrogen atmosphere at 0° C., was added methyl magnesium bromide (3.0M solution in diethyl ether; 8.10 mL) and stirred for 2 h at 0° C. The reaction mixture was quenched with saturated ammonium chloride solution and extracted into ethyl acetate, dried (MgSO4) and the solvents removed in vacuo to give 2-(1-benzyl-piperidine-4-yl)-propan-2-ol (1.11 g) as a white solid.

To a suspension of 10% palladium on charcoal (40 mg) stirring in dry MeOH (10 mL) under a nitrogen atmosphere was added 2-(1-benzyl-piperidine-4-yl)-propan-2-ol (0.25 g) and the mixture warmed to 60° C. After 3 h the mixture was cooled, filtered through a celite bed and the solvents removed in vacuo to yield the desired amine (153 mg) as a colourless oil.

$^1$H NMR (400 MHz, d$_6$-DMSO) 1.03 (s, 6H), 1.09 (m, 1H), 1.23 (m, 2H), 1.66 (m, 2H), 1.98 (m, 2H), 2.97 (m, 2H), 3.83 (m, CH$_2$×2+CH$_2$), 4.00 (m, 4H), 7.46 (t, 2H, J=7.3 Hz), 7.65 (d, 1H, J=8.2 Hz), 8.21 (d, 1 h, J=7.1 Hz), 8.87 (s, 1H), 13.15 (br s, 1H); MS (ESI$^+$) 493.2 (MH$^+$).

139 2-(1H-Indazol-4-yl)-4-morpholin-4-yl-6-[4-(1-oxy-pyridin-3-ylmethyl)-piperazin-1-ylmethyl]-thieno[3,2-d]pyrimidine Via 2-chloro-4-morpholin-4-yl-6-[4-(1-oxy-pyridin-3-ylmethyl)-piperazin-1-ylmethyl]-thieno[3,2-d]pyrimidine, prepared from 1-(1-oxy-pyridin-3-ylmethyl)-piperazine.

Amine preparation: A mixture of 3-pyridylcarbinol-N-oxide (2.09 g) and thionyl chloride (1.65 mL) in dry chloroform (20 mL) was heated at 60° C. After 3 h, excess thionyl chloride was decomposed by addition of ethanol (0.5 mL). The resulting mixture was concentrated in vacuo. Trituration with ether/acetone gave 3-chloromethyl-pyridine 1-oxide (2.27 g). A mixture of 3-chloromethyl-pyridine 1-oxide (1.25 g), 1-BOC-piperazine (1.47 g), K$_2$CO$_3$ (1.23 g) was heated at reflux in dry MeCN (25 mL). After 18 h, the reaction mixture was cooled, diluted with water, extracted with DCM, dried (Na$_2$SO$_4$), filtered and concentrated in vacuo then purified by flash chromatography (4% MeOH/DCM) to give 4-(1-oxy-pyridin-3-ylmethyl)-piperazine-1-carboxylic acid tert-butyl ester (1.18 g). Treatment of this compound with HCl in DCM/MeOH yielded the desired amine, which was isolated as the hydrochloride salt.

$^1$H NMR (400 MHz, CDCl$_3$) 2.54 (m, 4H, 2×CH$_2$), 2.61 (m, 4H, 2×CH$_2$), 3.49 (s, 2H, CH$_2$), 3.85 (s, 2H, CH$_2$), 3.90-3.93 (m, 4H, 2×CH$_2$), 4.07-4.10 (m, 4H, 2×CH$_2$), 7.18-7.22 (m, 2H, 2×ArH), 7.37 (s, H, ArH), 7.49 (t, H, ArH, J=7.75 Hz), 8.11 (d, H, ArH, J=5.2 Hz), 8.27 (m, 2H, 2×ArH), 9.30 (s, H, ArH), 10.27 (br s, H, NH); MS (ESI$^+$) 543.3 (MH$^+$).

140 2-(1H-Indazol-4-yl)-4-morpholin-4-yl-6-(4-morpholin-4-ylmethyl-piperidin-1-ylmethyl)-thieno[3,2-d]pyrimidine Via 2-chloro-4-morpholin-4-yl-6-(4-morpholin-4-ylmethyl-piperidin-1-ylmethyl)-thieno[3,2-d]pyrimidine, prepared from 4-piperidin-4-ylmethyl-morpholine.

Amine preparation: To a solution of 1-BOC-piperidine-4-ethyl ester (2.0 g), stirring in dry DCM (30 mL), at −78° C. under a nitrogen atmosphere was added diisobutylaluminium hydride solution (1.0M in hexane; 8.0 mL), the mixture was stirred at −78° C. for 2 h, then warmed to room temperature and quenched with MeOH (1 mL). The mixture was extracted into DCM and dried (MgSO4), and the solvents removed in vacuo to give a residue which was purified using flash chromatography to give 1-BOC-4-formyl-piperidine (457 mg).

To a solution of 1-BOC-4-formyl-piperidine (210 mg) in dry 1,2-dichloroethane (10 mL), was added morpholine (86 mg) and glacial acetic acid (60 μL) and stirred for 1 h at room temperature. To the mixture was added sodium triacetoxyborohydride (272 mg) and the mixture stirred for 12 h. The reaction mixture was extracted into DCM (25 mL), washed with 50% sodium bicarbonate solution (10 mL), brine (10 mL), and dried (MgSO$_4$). The solvents were removed in vacuo to give a residue which was purified by flash chromatography to give 4-morpholine-4-ylmethyl-piperidine-1-carboxylic acid tert-butyl ester (120 mg). Treatment with TFA yielded the desired amine which was isolated as the TFA salt.

$^1$H NMR (400 MHz, d$_6$-DMSO) 1.13 (m, 2H), 1.50 (m, 1H), 1.67 (m, 2H), 2.04 (m, 2H), 2.10 (d, 2H, J=7.2 Hz), 2.28 (br s, 4H), 2.89 (m, 2H), 3.53 (m, 4H), 3.77 (m, 4H+CH$_2$), 3.99 (m, 4H), 7.45 (t, 2H, J=9.8 Hz), 7.65 (d, 1H, J=8.2 Hz), 8.21 (d, 1H, J=6.8 Hz), 8.87 (s, 1H), 13.15 (bs, 1H); MS (ESI$^+$) 534.3 (MH$^+$).

141 {1-[2-(1H-Indazol-4-yl)-4-morpholin-4-yl-thieno[3,2-d]pyrimidin-6-ylmethyl]-piperidin-4-ylmethyl}-(2-methoxy-ethyl)-methyl-amine Via [1-(2-Chloro-4-morpholin-4-yl-thieno[3,2-d]pyrimidin-6-ylmethyl)-piperidin-4-ylmethyl]-(2-methoxy-ethyl)-methyl-amine, prepared from (2-methoxy-ethyl)-methyl-piperidin-4-ylmethyl-amine. The amine, (2-methoxy-ethyl)-methyl-piperidin-4-ylmethylamine, was prepared in an analogous manner to that for 140 using N-(2-methoxyethyl) methylamine.

$^1$H NMR (400 MHz, d$_6$-DMSO) 1.09 (m, CH$_2$), 1.44 (m, CH$_2$) 1.67 (m, CH$_2$), 2.04 (t, CH$_2$, J=11.5 Hz), 2.15 (m, 3H+CH$_2$), 2.43 (t, CH$_2$, J=6.0 Hz), 2.90 (m, CH$_2$), 3.21 (s, 3H), 3.39 (m, CH$_2$), 3.83 (m, 4H+CH$_2$), 3.99 (m, 4H), 7.46 (t, 1H, J=6.2 Hz), 7.66 (d, 1H, J=8.3 Hz), 8.21 (d, 1H, J=7.4 Hz), 8.87 (s, 1H), 13.25 (br s, 1H); MS (ESI$^+$) 536.4 (MH$^+$).

142 {1-[2-(1H-Indazol-4-yl)-4-morpholin-4-yl-thieno[3,2-d]pyrimidin-6-ylmethyl]-piperidin-4-ylmethyl}-dimethyl-amine Via [1-(2-Chloro-4-morpholin-4-yl-thieno[3,2-d]pyrimidin-6-ylmethyl)-piperidin-4-ylmethyl]-dimethyl-amine, prepared from dimethyl-piperidin-4-ylmethyl-amine. The amine, dimethyl-piperidin-4-ylmethyl-amine, was prepared in an analogous manner to that for 140 using dimethylamine.

$^1$H NMR (400 MHz, d$_6$-DMSO): 1.11 (m, CH$_2$), 1.42 (m, CH), 1.66 (m, CH$_2$), 2.03 (m, CH$_2$×2), 2.08 (s, 6H), 2.89 (m, 2H), 3.82 (m, 4 h, +CH$_2$), 3.99 (m, 4H), 7.45 (t, 2H, J=7.3 Hz), 7.65 (d, 1H, J=8.3 Hz), 8.21 (d, 1H, J=7.3 Hz), 8.87 (s, 1H), 13.2 (br s, 1H); MS (ESI$^+$) 492.3 (MH$^+$).

143 {1-[2-(1H-Indazol-4-yl)-4-morpholin-4-yl-thieno[3,2-d]pyrimidin-6-ylmethyl]-piperidin-3-yl}-(2-methoxy-ethyl)-methyl-amine Via [1-(2-Chloro-4-morpholin-4-yl-thieno[3,2-d]pyrimidin-6-ylmethyl)-piperidin-3-yl]-(2-methoxy-ethyl)-methyl-amine, prepared from (2-methoxy-ethyl)-methyl-piperidin-3-yl-amine.

Amine preparation: A mixture of 1-BOC-3-piperidone (0.50 g), N-(2-methoxyethyl)methylamine (0.29 g), sodium triacetoxyborohydride (0.74 g) and acetic acid (0.14 mL) in 1,2-dichloroethane (30 mL) was stirred at room temperature for 6 h. The reaction mixture was then diluted with DCM, washed with sodium bicarbonate solution, dried (MgSO$_4$) and the solvent removed in vacuo. The residue was purified by flash chromatography to yield 3-[(2-methoxy-ethyl)-methyl-amino]-piperidine-1-carboxylic acid tert-butyl ester (0.556 g). Treatment of this compound with HCl in DCM/MeOH yielded the desired amine, which was isolated as the hydrochloride salt.

$^1$H NMR (400 MHz, CDCl$_3$): 1.27 (1H, m), 1.60 (1H, m), 1.77 (1H, m), 1.98 (3H, m), 2.35 (3H, s), 2.68 (3H, m), 2.92 (1H, d, J=10.5 Hz), 3.10 (1H, m), 3.34 (3H, s), 3.44 (2H, m), 3.86 (2H, s), 3.92 (4H, m), 4.08 (4H, m), 7.37 (1H, s), 7.50 (1H, t, J=7.7 Hz), 7.60 (1H, d, J=8.3 Hz), 8.27 (1H, d, J=7.3 Hz), 9.01 (1H, s), 10.20 (1H, br s); MS (ESI$^+$) 522 (MH$^+$).

144 1-[2-(1H-Indazol-4-yl)-4-morpholin-4-yl-thieno [3,2-d]pyrimidin-6-ylmethyl]-piperidine-3-carboxylic acid methylamide Via 1-(2-chloro-4-morpholin-4-yl-thieno[3,2-d]pyrimidin-6-ylmethyl)-piperidine-3-carboxylic acid methylamide, prepared from piperidine-3-carboxylic acid methylamide.

Amine preparation: To a solution of 1-(tert-butoxycarbonyl)-3-piperidine-carboxylic acid (0.50 g) in DMF (3 mL) was added 1,1'-carbonyldiimidazole (0.70 g). The reaction mixture was stirred for 4 h and then triethylamine (0.60 mL) followed by methylamine hydrochloride (0.29 g) was added. After stirring for 24 h the reaction mixture was then diluted with ethyl acetate, washed with water, brine, dried (MgSO$_4$) and the solvent removed in vacuo. The residue was purified by flash chromatography to yield 3-methylcarbamoyl-piperidine-1-carboxylic acid tert-butyl ester (0.41 g). Treatment of this compound with HCl in DCM/MeOH yielded the desired amine, which was isolated as the hydrochloride salt.

$^1$H NMR (400 MHz, CDCl$_3$) 1.58-1.94 (4H, m), 2.50 (2H, m), 2.65 (2H, m), 2.84 (3H, d), 2.80 (1H, m), 3.85 (2H, m), 3.92 (4H, m), 4.10 (4H, m), 7.00 (1H, br s), 7.40 (1H, s), 7.50 (1H, t, J=7.7 Hz), 7.60 (1H, d, J=8.2 Hz), 8.29 (1H, d, J=7.1 Hz), 9.03 (1H, s), 10.10 (1H, br s); MS (ESI$^+$) 492 (MH$^+$).

145 2-(1H-Indazol-4-yl)-6-[(3-methoxymethyl-piperidin-1-ylmethyl)-4-morpholin-4-yl-thieno[3,2-d]pyrimidine Via 2-Chloro-6-(3-methoxymethyl-piperidin-1-ylmethyl)-4-morpholin-4-yl-thieno[3,2-d]pyrimidine, prepared from 3-methoxymethyl-piperidine.

Amine preparation: To a solution of 1-BOC-3-piperidine carboxylic acid (3.0 g) in DMF (25 mL) was added potassium carbonate (3.62 g) followed by iodomethane (4.07 mL). After 2.5 h the reaction was diluted with water and extracted into diethyl ether. The organic layer was washed with brine, separated and dried (MgSO$_4$). The solvent was evaporated to give piperidine-1,3-dicarboxylic acid 1-tert-butyl ester 3-methyl ester (2.98 g).

To a suspension of lithium aluminium hydride (1.41 g) in THF (15 mL) at 0° C. was added piperidine-1,3-dicarboxylic acid 1-tert-butyl ester 3-methyl ester as a solution in THF (10 mL) and the mixture stirred at room temperature for 3 h. The reaction was cooled to 0° C. and quenched by addition of aqueous ammonium chloride and the mixture filtered through celite. The filtrate was diluted with ethyl acetate, washed with water, separated and dried (MgSO$_4$). The solvent was evaporated to give 3-hydroxymethyl-piperidine-1-carboxylic acid tert-butyl ester (1.25 g). To a solution of this alcohol (422 mg) in THF (8 mL) was added sodium hydride (94 mg; 60% dispersion in mineral oil). After 15 min iodomethane (0.49 mL) was added and the reaction stirred for 18 h. The mixture was then diluted with ethyl acetate and washed sequentially with water, brine, separated and dried (MgSO$_4$). The solvent was evaporated and the residue purified by flash chromatography to give 3-methoxymethyl-piperidine-1-carboxylic acid tert-butyl ester (414 mg). To a solution of 3-methoxymethyl-piperidine-1-carboxylic acid tert-butyl ester (204 mg) in DCM (3 mL) was added 2M hydrogen chloride in diethyl ether and the mixture stirred for 18 h. The solvent was evaporated to give the desired amine (168 mg).

$^1$H NMR (400 MHz, CDCl$_3$) 1.06 (s, 1H), 1.63-1.75 (m, 2H), 1.90-1.95 (m, 3H), 2.12 (m, 1H), 2.88 (m, 1H), 2.99 (m, 1H), 3.25 (m, 2H), 3.31 (s, 3H), 3.83 (s, 2H), 3.92 (t, J=4.8 Hz, 4H), 4.09 (t, J=4.8 Hz, 4H), 7.35 (s, 1H), 7.50 (t, J=7.8 Hz, 1H), 7.57 (d, J=8.2 Hz, 1H), 8.28 (d, J=7.4 Hz, 1H), 9.02 (s, 1H), 10.10 (br s, 1H); MS (ESI$^+$) 479.26 (MH$^+$).

146 2-(1H-Indazol-4-yl)-4-morpholin-4-yl-6-(4-pyridin-2-ylmethyl-piperidin-1-ylmethyl)-thieno[3,2-d]pyrimidine Via 2-chloro-4-morpholin-4-yl-6-(4-pyridin-2-ylmethyl-piperidin-1-ylmethyl)-thieno[3,2-d]pyrimidine, prepared from 2-piperidin-4-ylmethyl-pyridine.

Amine preparation: 4-Pyridin-2-ylmethyl-piperidine-1-carboxylic acid tert-butyl ester was synthesized according to the procedure described in *J. Org. Chem.* 2001, 66, 2487. It was treated further with HCl in DCM/MeOH to yield the desired amine.

$^1$H NMR (400 MHz, CDCl$_3$) 1.40-1.50 (2H, m), 1.64-1.70 (2H, m), 1.81-1.92 (1H, m), 2.06-2.13 (2H, m), 2.74 (2H, d, J=7.2 Hz), 2.96-3.03 (2H, m), 3.83 (2H, s), 3.90-3.96 (4H, m), 4.05 (4H, m), 7.10-7.13 (2H, m), 7.32 (1H, s), 7.50-7.53 (1H, m), 7.56-7.62 (2H, m), 8.26 (1H, d, J=6.8 Hz), 8.52-8.54 (1H, m), 9.01 (1H, s), 10.20 (1H, br); MS (ESI$^+$) 526 (MH$^+$).

147 2-(1H-Indazol-4-yl)-6-[4-(2-methoxy-ethoxy)-piperidin-1-ylmethyl]-4-morpholin-4-yl-thieno[3,2-d]pyrimidine Via 2-chloro-6-[4-(2-methoxy-ethoxy)-piperidin-1-ylmethyl]-4-morpholin-4-yl-thieno[3,2-d]pyrimidine, prepared from 4-(2-methoxy-ethoxy)-piperidine.

Amine preparation: To 4-hydroxy-piperidine-1-carboxylic acid tert-butyl ester (1.5 g) in dry DMF (15 mL) was added sodium hydride (447 mg). After stirring for 2 hrs at room temperature, 2-bromoethyl methyl ether (0.7 mL) was added. The reaction mixture was heated to 40° C. overnight, and then diluted with ethyl acetate, washed with water and dried (MgSO$_4$). The solvent was evaporated and the residue purified by flash chromatography to give 4-(2-methoxy-ethoxy)-piperidine-1-carboxylic acid tert-butyl ester (447 mg). Treatment of this compound with HCl in DCM/MeOH yielded the desired amine, which was isolated as the hydrochloride salt.

$^1$H NMR (400 MHz, CDCl$_3$) 1.72 (m, 2H), 1.94 (m, 2H), 2.30 (m, 2H), 2.85 (m, 2H), 3.40 (s, 4H), 3.55 (m, 2H), 3.61 (m, 2H), 3.84 (s, 2H), 3.92 (m, 4H), 4.09 (m, 4H), 7.35 (s, 1H), 7.52 (m, 1H), 7.59 (d, J=8.2 Hz, 1H), 8.28 (d, J=6.8 Hz, 1H), 9.02 (s, 1H); MS (ESI$^+$) 509 (MH$^+$).

148 6-((3R,5S)-3,5-Dimethyl-4-thiazol-2-ylmethyl-piperazin-1-ylmethyl)-2-(1H-indazol-4-yl)-4-morpholin-4-yl-thieno[3,2-d]pyrimidine Via 2-chloro-6-((3R,5S)-3,5-dimethyl-4-thiazol-2-ylmethyl-piperazin-1-ylmethyl)-4-morpholin-4-yl-thieno[3,2-d]pyrimidine, prepared from (2R,6S)-2,6-dimethyl-1-thiazol-2-ylmethyl-piperazine.

Amine preparation: 2-Thiazolecarboxaldehyde was converted to the corresponding alcohol by treatment with sodium borohydride. Reaction with methanesulfonyl chloride yielded methanesulfonic acid thiazol-2-ylmethyl ester. A mixture of methanesulfonic acid thiazol-2-ylmethyl ester (393 mg), (3R,5S)-3,5-dimethyl-piperazine-1-carboxylic acid tert-butyl ester (described previously, 435 mg), potassium carbonate (309 mg) and tetrabutyl ammonium iodide (827 mg) was heated to reflux in MeCN (10 mL). After 4 days the reaction mixture was cooled, diluted with ethyl acetate, washed with water and dried (MgSO$_4$). The solvent was evaporated and the residue purified by flash chromatography to give (R)-3,5-dimethyl-4-thiazol-2-ylmethyl-piperazine-1- carboxylic acid (S)-tert-butyl ester (314 mg). Treatment of this compound with HCl in DCM/MeOH yielded the desired amine, which was isolated as the hydrochloride salt.

$^1$H NMR (400 MHz, CDCl$_3$) 1.12 (d, J=6.0 Hz, 6H), 2.06 (m, 2H), 2.85 (m, 4H), 3.80 (s, 2H), 3.92 (m, 4H), 4.09 (m, 4H), 4.17 (s, 2H), 7.24 (d, J=3.2 Hz, 1H), 7.38 (s, 1H), 7.51 (m, 1H), 7.59 (d, J=8.3 Hz, 1H), 7.74 (d, J=3.3 Hz, 1H), 8.29 (d, J=7.3 Hz, 1H), 9.03 (s, 1H), 10.1 (br s, 1H); MS (ESI$^+$) 561 (MH$^+$).

149 2-(1H-Indazol-4-yl)-4-morpholin-4-yl-6-[4-(1-oxy-pyridin-2-ylmethyl)-piperazin-1-ylmethyl]-thieno[3,2-d]pyrimidine Via 2-chloro-4-morpholin-4-yl-6-[4-(1-oxy-pyridin-2-yl-methyl)-piperazin-1-ylmethyl]-thieno[3,2-d]pyrimidine, prepared from 1-(1-oxy-pyridin-2-ylmethyl)-piperazine.

Amine preparation: To 2-pyridylcarbinol (2.26 g) in chloroform (20 mL) was added mCPBA (5.57 g) at 0° C. The reaction mixture was allowed to stir at that temperature for 1 h, the solvent was removed in vacuo and the residue was purified using flash chromatography to yield (1-oxy-pyridin-2-yl)-methanol as a white solid (2.73 g). To a precooled (0° C.) solution of (1-oxy-pyridin-2-yl)-methanol (2.73 g) in dry chloroform (25 mL) was added thionyl chloride (2.07 mL) dropwise. The reaction mixture was heated at 60° C. for 3 h, cooled to room temperature, quenched with ethanol (1 mL and reduced in vacuo. The residue was taken up in DCM, washed with aqueous sodium bicarbonate, dried (MgSO$_4$) and the solvent removed in vacuo to give 2-chloromethyl-pyridine 1-oxide as an oil (2.60 g), which solidified on standing. BOC-piperazine (500 mg) and 2-chloromethyl-pyridine 1-oxide (385 mg) were refluxed in MeCN (100 mL) with potassium carbonate (550 mg). After 4 h, the reaction mixture was reduced in vacuo, the residue was taken up in DCM, washed with brine, dried (MgSO$_4$) and the solvent removed in vacuo to give 4-(1-oxy-pyridin-2-ylmethyl)-piperazine-1-carboxylic acid tert-butyl ester (788 mg). Treatment of this compound with HCl in DCM/MeOH yielded the desired amine, which was isolated as the hydrochloride salt.

$^1$H NMR (400 MHz, CDCl$_3$): 2.65-2.76 (8H, m), 3.88 (2H, s), 3.89 (2H, s), 3.90-3.92 (4H, m), 4.03-4.05 (4H, m), 7.14-7.18 (1H, m), 7.26-7.29 (1H, m), 7.37 (1H, s), 7.48-7.51 (1H, m), 7.55-7.59 (2H, m), 8.23-8.29 (2H, m), 9.02 (1H, s); MS (ESI$^+$) 543 (MH$^+$).

150 2-(1H-Indazol-4-yl)-6-[4-(2-methoxy-ethyl)-piperidin-1-ylmethyl]-4-morpholin-4-yl-thieno[3,2-d]pyrimidine Via 2-Chloro-6-[4-(2-methoxy-ethyl)-piperidin-1-ylmethyl]-4-morpholin-4-yl-thieno[3,2-d]pyrimidine, prepared from 4-(2-methoxy-ethyl)-piperidine.

Amine preparation: To a solution of 4-piperidine ethanol (540 mg) in MeCN (8 mL) was added triethylamine (0.70 mL) followed by tert-butyl dicarbonate (1.00 g). The mixture was stirred at room temperature for 22 h and partitioned between 0.5 M hydrochloric acid and ethyl acetate. The organic layer was washed with brine, dried (MgSO$_4$) and the solvent evaporated to give 4-(2-hydroxy-ethyl)-piperidine-1-carboxylic acid tert-butyl ester (897 mg). This was dissolved in THF (14 mL) and sodium hydride added (172 mg; 60% dispersion in mineral oil) at 0° C. After 30 min iodomethane (0.97 mL) was added and the mixture stirred for 22 h. The mixture was diluted with ethyl acetate and washed with water, brine and dried (MgSO$_4$). The solvent was evaporated and the residue purified by flash chromatography to give 4-(2-meth-oxy-ethyl)-piperidine-1-carboxylic acid tert-butyl ester (724 mg). To a solution of 4-(2-methoxy-ethyl)-piperidine-1-carboxylic acid tert-butyl ester (284 mg) in DCM (5 mL) was added 2M hydrogen chloride in diethyl ether (5.0 mL) and the mixture stirred for 21 h. The solvent was evaporated to give the desired amine as a white solid.

$^1$H NMR (400 MHz, CDCl$_3$) 1.45-1.25 (m, 5H), 1.71 (m, 2H), 2.10 (m, 2H), 2.98 (m, 2H), 3.33 (s, 3H), 3.42 (t, J=6.5 Hz, 2H), 3.83 (s, 2H), 3.92 (t, J=4.8 Hz, 4H), 4.09 (t, J=4.8 Hz, 4H), 7.36 (s, 1H), 7.51 (t, J=7.7 Hz, 1H), 7.59 (d, J=8.3 Hz, 1H), 8.28 (d, J=6.7 Hz, 1H), 9.02 (s, 1H), 10.05 (br s, 1H); MS (ESI$^+$) 493.27 (MH$^+$).

151 2-(1H-Indazol-4-yl)-6-(4-methanesulfonyl-piperidin-1-ylmethyl)-4-morpholin-4-yl-thieno[3,2-d]pyrimidine Via 2-chloro-6-(4-methanesulfonyl-piperidin-1-ylmethyl)-4-morpholin-4-yl-thieno[3,2-d]pyrimidine, prepared from 4-methanesulfonyl-piperidine.

Amine preparation: A mixture of 4-methanesulfonyloxy-piperidine-1-carboxylic acid tert-butyl ester (1.015 g), sodium thiomethoxide (635 mg) was heated to 80° C. in DMF (10 mL). After 4 h, the reaction mixture was diluted with water, extracted with ethyl acetate, dried (MgSO$_4$), filtered and concentrated in vacuo and then purified by flash chromatography to give 4-methylsulfanyl-piperidine-1-carboxylic acid tert-butyl ester (600 mg). To a solution of 4-methylsulfanyl-piperidine-1-carboxylic acid tert-butyl ester (600 mg) in chloroform (15 mL) was added mCPBA (1.46 g). After stirring for 2 days, the reaction mixture was diluted with DCM, washed with sodium bicarbonate solution, dried (MgSO$_4$) and the solvent removed in vacuo to yield 4-methanesulfonyl-piperidine-1-carboxylic acid tert-butyl ester (505 mg) as a white solid. Treatment of this compound with HCl in DCM/MeOH yielded the desired amine, isolated as the hydrochloride salt.

$^1$H NMR (400 MHz, CDCl$_3$) 1.90-2.05 (2H, m), 2.10-2.18 (4H, m), 2.90 (3H, s), 2.91-2.94 (1H, m), 3.21 (2H, d), 3.88 (2H, s), 3.91-3.93 (4H, m), 4.10-4.12 (4H, m), 7.40 (1H, s), 7.48-7.52 (1H, m), 7.58 (1H, d), 8.25 (1H, d), 9.05 (1H, s), 10.25 (s br, 1H); MS (ESI$^+$) 513 (MH$^+$).

152 {1-[2-(1H-Indazol-4-yl)-4-morpholin-4-yl-thieno[3,2-d]pyrimidin-6-ylmethyl]-piperidin-4-yl}-(3-methanesulfonyl-propyl)-methyl-amine Via [1-(2-chloro-4-morpholin-4-yl-thieno[3,2-d]pyrimidin-6-ylmethyl)-piperidin-4-yl]-(3-methanesulfonyl-propyl)-methyl-amine, prepared from (3-methanesulfonyl-propyl)-methyl-piperidin-4-yl-amine.

Amine preparation: Toluene-4-sulfonic acid 3-methylsulfanyl-propyl ester was prepared from 3-(methylthio)-1-propanol using standard conditions. Treatment with mCPBA in DCM yielded toluene-4-sulfonic acid 3-methanesulfonyl-propyl ester. A mixture of 4-methylamino-piperidine-1-carboxylic acid tert-butyl ester and toluene-4-sulfonic acid 3-methanesulfonyl-propyl ester was heated in MeCN in the prescence of potassium carbonate to yield 4-[(3-methanesulfonyl-propyl)-methyl-amino]-piperidine-1-carboxylic acid tert-butyl ester. Treatment of this compound with HCl in DCM/MeOH yielded the desired amine, isolated as the hydrochloride salt.

$^1$H NMR (400 MHz, CDCl$_3$) 1.50-1.70 (m, 4H, 2×CH$_2$), 1.90-1.97 (m, 2H, CH$_2$), 2.00-2.05 (m, 2H, CH$_2$), 2.21 (s, 3H, CH$_3$), 2.38 (m, H, CH), 2.55 (m, 2H, CH$_2$), 2.74 (s, 3H, CH$_2$), 2.96-3.04 (m, 4H, 2×CH$_2$), 3.75 (s, 2H, CH$_2$), 3.83-3.89 (m, 4H, 2×CH$_2$), 4.00-4.02 (m, 4H, 2×CH$_2$), 7.28 (s, H, CH), 7.41 (t, H, ArH, J=7.74 Hz), 7.50 (d, H, ArH, J=8.24 Hz), 8.18 (d, H, ArH, J=7.05 Hz), 8.93 (s, H, ArH); MS (ESI$^+$) 584.39 (MH$^+$).

153 2-(1H-Indazol-4-yl)-6-[4-(3-methoxy-propane-1-sulfonyl)-piperidin-1-ylmethyl]-4-morpholin-4-yl-thieno[3,2-d]pyrimidine Via 2-chloro-6-[4-(3-methoxy-propane-1-sulfonyl)-piperidin-1-ylmethyl]-4-morpholin-4-yl-thieno[3,2-d]pyrimidine, prepared from 4-(3-methoxy-propane-1-sulfonyl)-piperidine.

Amine preparation: A mixture of 4-methanesulfonyloxy-piperidine-1-carboxylic acid tert-butyl ester (2.82 g) and potassium thioacetate (2.31 g) was heated to 60° C. in DMF (10 mL). After 4 h, the reaction mixture was diluted with water, extracted with ethyl acetate, dried (MgSO$_4$), filtered and concentrated in vacuo and then purified by flash chromatography to give 4-acetylsulfanyl-piperidine-1-carboxylic acid tert-butyl ester (1.80 g). To a solution of 4-acetylsulfanyl-piperidine-1-carboxylic acid tert-butyl ester (607 mg) in dry MeOH (5 mL) was added a solution of sodium methoxide in MeOH (25% wt, 0.59 mL). After stirring for 15 min, toluene-4-sulfonic acid 3-methoxy-propyl ester (described elsewhere, 571 mg) was added in MeOH. After 24 h, the reaction mixture was diluted with water, extracted with ethyl acetate, dried (MgSO$_4$), filtered and concentrated in vacuo to yield 4-(3-methoxy-propylsulfanyl)-piperidine-1-carboxylic acid tert-butyl ester. Treatment with mCPBA (as described above) yielded 4-(3-methoxy-propane-1-sulfonyl)-piperidine-1-carboxylic acid tert-butyl ester. Treatment of this compound with HCl in DCM/MeOH yielded the desired amine, isolated as the hydrochloride salt.

$^1$H NMR (400 MHz, CDCl$_3$) 1.95-2.20 (8H, m), 2.85-2.91 (1H, m), 3.02-3.06 (2H, t), 3.13-3.20 (2H, d), 3.31 (3H, s), 3.52 (2H, t), 3.88 (2H, s), 3.94-3.99 (4H, m), 4.09-4.13 (4H, m), 7.35 (1H, s), 7.45-7.52 (1H, m), 7.55 (1H, d), 8.29 (1H, d), 9.05 (1H, s), 10.30 (1H, br s); MS (ESI$^+$) 571 (MH$^+$).

154 (R)-1-[2-(1H-Indazol-4-yl)-4-morpholin-4-yl-thieno[3,2-d]pyrimidin-6-ylmethyl]-piperidine-3-carboxylic acid methylamide Via (R)-1-(2-chloro-4-morpholin-4-yl-thieno[3,2-d]pyrimidin-6-ylmethyl)-piperidine-3-carboxylic acid methylamide, prepared from (R)-piperidine-3-carboxylic acid methylamide.

Amine preparation: To a suspension of (S)-(−)-nipecotic acid hydrochloride (1.0 g) in MeCN (10 mL) was added triethylamine (1.85 mL) followed by di-tert-butyldicarbonate (1.45 g). After stirring for 24 h the reaction mixture was then diluted with DCM, washed with brine, dried (MgSO$_4$) and the solvent removed in vacuo. The residue was purified by flash chromatography to yield piperidine-1,3-dicarboxylic acid 1-tert-butyl ester (0.54 g). Procedure continued as for 144.

$^1$H NMR (400 MHz, CDCl$_3$) 1.58-1.94 (4H, m), 2.50 (2H, m), 2.65 (2H, m), 2.84 (3H, d), 2.80 (1H, m), 3.85 (2H, m), 3.92 (4H, m), 4.10 (4H, m), 7.00 (1H, br s), 7.40 (1H, s), 7.50 (1H, t, J=7.7 Hz), 7.60 (1H, d, J=8.2 Hz), 8.29 (1H, d, J=7.1 Hz), 9.03 (1H, s), 10.10 (1H, br s); MS (ESI$^+$) 492 (MH$^+$).

155 (S)-1-[2-(1H-Indazol-4-yl)-4-morpholin-4-yl-thieno[3,2-d]pyrimidin-6-ylmethyl]-piperidine-3-carboxylic acid methylamide Via (S)-1-(2-chloro-4-morpholin-4-yl-thieno[3,2-d]pyrimidin-6-ylmethyl)-piperidine-3-carboxylic acid methylamide, prepared from (S)-piperidine-3-carboxylic acid methylamide. Amine preparation as for 154, utilizing (R)-(+)-nipecotic acid hydrochloride as the starting material.

$^1$H NMR (400 MHz, CDCl$_3$): 1.58-1.94 (4H, m), 2.50 (2H, m), 2.65 (2H, m), 2.84 (3H, d), 2.80 (1H, m), 3.85 (2H, m), 3.92 (4H, m), 4.10 (4H, m), 7.00 (1H, br s), 7.40 (1H, s), 7.50 (1H, t, J=7.7 Hz), 7.60 (1H, d, J=8.2 Hz), 8.29 (1H, d, J=7.1 Hz), 9.03 (1H, s), 10.10 (1H, br s); MS (ESI$^+$) 492 (MH$^+$).

156 6-(4-Imidazol-1-ylmethyl-piperidin-1-ylmethyl)-2-(1H-indazol-4-yl)-4-morpholin-4-yl-thienor[3,2-d]pyrimidine Via 2-chloro-6-(4-imidazol-1-ylmethyl-piperidin-1-ylmethyl)-4-morpholin-4-yl-thieno[3,2-d]pyrimidine, prepared from 4-imidazol-1-ylmethyl-piperidine.

Amine preparation: To a solution of 4-hydroxymethyl-piperidine-1-carboxylic acid tert-butyl ester (250 mg), in dry THF (15 mL), was added carbon tetrabromide (769 mg), and triphenyl phosphine (609 mg). The reaction mixture was stirred at room temperature for 24 h, and then the solvents were evaporated in vacuo to give a residue which was purified by flash chromatography to give 4-bromomethyl-piperidine-1-carboxylic acid tert-butyl ester (279 mg), as a colourless oil. To a solution of 4-bromomethyl-piperidine-1-carboxylic acid tert-butyl ester (240 mg), in dry DMF (5.0 mL), was added imidazole (129 mg). The reaction mixture was heated in a sealed reaction vial at 100° C. for 24 h, then cooled and the contents evaporated onto flash silica for purification. Treatment of this compound with HCl in DCM/MeOH yielded the desired amine, isolated as the hydrochloride salt.

$^1$H NMR (400 MHz, d$_6$-DMSO) 1.23 (m, 2H), 1.47 (m, 2H), 1.69 (m, CH), 2.01 (m, 2H), 2.92 (m, 2H), 3.83 (m, 4H+CH$_2$×2), 3.99 (m, 4H), 6.87 (s, 1H), 7.13 (s, 1H), 7.46 (t, 1H, J=7.6 Hz), 7.58 (s, 1H), 7.65 (d, 1H, J=8.2 Hz), 8.21 (d, 1H, J=7.3 Hz), 8.87 (s, 1H), 13.2 (br s, 1H); MS (ESI$^+$) 515.2 (MH$^+$).

157 2-(1H-Indazol-4-yl)-4-morpholin-4-yl-6-morpholin-4-ylmethyl-thieno[3,2-d]pyrimidine Via 2-Chloro-4-morpholin-4-yl-6-morpholin-4-ylmethyl-thieno[3,2-d]pyrimidine, prepared from morpholine.

$^1$H NMR (400 MHz, CDCl$_3$) 2.58-2.63 (4H, m), 3.72-3.78 (4H, m), 3.82 (2H, s), 3.88-3.93 (4H, m), 4.05-4.11 (4H, m), 7.38 (1H, s), 7.50-7.55 (2H, m), 7.60 (1H, d, J=8.3 Hz), 8.28 (1H, d, J=7.2 Hz), 9.00 (1H, s), 10.10 (1H, br); MS (ESI$^+$) 437 (MH$^+$).

158 2-(1H-Indazol-4-yl)-6-(3-methyl-piperidin-1-ylmethyl)-4-morpholin-4-yl-thieno[3,2-d]pyrimidine Via 2-Chloro-6-(3-methyl-piperidin-1-ylmethyl)-4-morpholin-4-yl-thieno[3,2-d]pyrimidine, prepared from 3-methyl-piperidine.

$^1$H NMR (400 MHz, CDCl$_3$) 0.88 (4H, m), 1.70 (5H, m), 2.04 (1H, m), 2.90 (2H, m), 3.80 (2H, s), 3.90 (4H, m), 4.10 (4H, m), 7.36 (1H, s), 7.50 (1H, t, J=7.7 Hz), 7.58 (1H, d, J=8.2 Hz), 8.29 (1H, d, J=7.1 Hz), 9.02 (1H, s), 10.10 (1H, br s); MS (ESI$^+$) 490 (MH$^+$).

159 {1-[2-(1H-Indazol-4-yl)-4-morpholin-4-yl-thieno[3,2-d]pyrimidin-6-ylmethyl]-piperidin-3-yl}-methanol Via [1-(2-chloro-4-morpholin-4-yl-thieno[3,2-d]pyrimidin-6-ylmethyl)-piperidin-3-yl]-methanol, prepared from piperidin-3-yl-methanol.

¹H NMR (400 MHz, CDCl₃) 1.18 (m, 1H), 1.58-1.88 (m, 4H), 2.12 (m, 1H), 2.27 (m, 1H), 2.77 (m, 1H), 2.93 (m, 1H), 3.56 (dd, J=10.6 Hz, 6.4 Hz, 1H), 3.64 (dd, J=10.6 Hz, 5.5 Hz, 1H), 3.84 (s, 2H), 3.92 (t, J=4.8 Hz, 4H), 4.09 (t, J=4.8 Hz, 4H), 7.36 (s, 1H), 7.51 (t, J=7.7 Hz, 1H), 7.59 (d, J=8.3 Hz, 1H), 8.27 (d, J=7.3 Hz, 1H), 9.01 (s, 1H), 10.10 (br s, 1H); MS (ESI⁺) 465.20 (MH⁺).

160 2-{1-[2-(1H-Indazol-4-yl)-4-morpholin-4-yl-thieno[3,2-d]pyrimidin-6-ylmethyl]-piperidin-4-yl}-ethanol Via 2-[1-(2-chloro-4-morpholin-4-yl-thieno[3,2-d]pyrimidin-6-ylmethyl)-piperidin-4-yl]-ethanol, prepared from 2-piperidin-4-yl-ethanol.

¹H NMR (400 MHz, d₆-DMSO) 1.18 (m, 2H), 1.36 (m, 3H), 1.63 (m, 2H), 2.02 (m, 2H), 2.91 (m, 2H), 3.30-3.45 (m, 2H), 3.84 (m, 6H), 3.99 (t, J=4.8 Hz, 4H), 4.35 (t, J=4.8 Hz, 4H), 7.46 (m, 2H), 7.65 (d, J=8.3 Hz, 1H), 8.21 (d, J=7.8 Hz, 1H), 8.87 (s, 1H); MS (ESI⁺) 479.25 (MH⁺).

161 1-[2-(1H-Indazol-4-yl)-4-morpholin-4-yl-thieno[3,2-d]pyrimidin-6-ylmethyl]-4-thiazol-2-yl-piperidin-4-ol Via 1-(2-Chloro-4-morpholin-4-yl-thieno[3,2-d]pyrimidin-6-ylmethyl)-4-thiazol-2-yl-piperidin-4-ol, prepared from 4-thiazol-2-yl-piperidin-4-ol.

¹H NMR (400 MHz, d₆-DMSO) 1.73 (m, 2H), 2.14 (m, 2H), 2.53 (m, 2H), 2.78 (m, 2H), 3.83 (m, 4H), 3.91 (s, 2H), 4.01 (m, 4H), 5.95 (s, 1H), 7.46 (t, 1H, J=7.6 Hz), 7.49 (s, 1H), 7.57 (d, 1H, J=3.1 Hz), 7.65 (d, 1H, J=8.3 Hz), 7.72 (d, 1H, J=3.3 Hz), 8.21 (d, 1H, J=7.3 Hz), 8.88 (s, 1H), 13.18 (br s, 1H); MS (ESI⁺) 534.3 (MH⁺).

Preparation of Boronate Ester Monomers for the Synthesis of 162 and 163

A solution of 4-(4,4,5,5-tetramethyl-[1,3,2]dioxaborolan-2-yl)-1H-indazole (400 mg) in dry DMF (4 mL) precooled to 0° C. was added to a suspension of sodium hydride (80 mg) in dry THF (5 mL) at −78° C. under inert atmosphere. After 30 min, iodomethane (112 uL) was added to the mixture at −78° C. The reaction mixture was allowed slowly to warm up to room temperature overnight and then diluted with DCM, washed with brine, dried (MgSO₄) and the solvent removed in vacuo. The residue was purified using flash chromatography to yield 1-methyl-4-(4,4,5,5-tetramethyl-[1,3,2]dioxaborolan-2-yl)-1H-indazole (143 mg) and 2-methyl-4-(4,4,5,5-tetramethyl-[1,3,2]dioxaborolan-2-yl)-2H-indazole (160 mg).

162 2-(1-Methyl-1H-indazol-4-yl)-6-(4-methyl-piperazin-1-ylmethyl)-4-morpholin-4-yl-thienor[3,2-d]pyrimidine Prepared in a similar manner to 59.

¹H NMR (400 MHz, CDCl₃) 2.32 (3H, s), 2.45-2.55 (4H, br m), 2.55-2.70 (4H, br m), 3.83 (2H, s), 3.90-3.93 (4H, m), 4.03-4.06 (4H, m), 4.12 (3H, s), 7.40 (1H, s), 7.49-7.52 (2H, m), 8.25-8.27 (1H, m), 8.90 (1H, s); MS (ESI⁺) 464 (MH⁺).

163 2-(2-Methyl-2H-indazol-4-yl)-6-(4-methyl-piperazin-1-vlmethyl)-4-morpholin-4-yl-thienor[3,2-d]pyrimidine Prepared in a similar manner to 59.

¹H NMR (400 MHz, CDCl₃) 2.32 (3H, s), 2.45-2.55 (4H, br m), 2.55-2.70 (4H, br m), 3.83 (2H, s), 3.90-3.93 (4H, m), 4.03-4.06 (4H, m), 4.30 (3H, s), 7.48 (2H, m), 7.81 (1H, d, J=8.4 Hz), 8.28 (1H, d, J=6.8 Hz), 8.90 (1H, s); MS (ESI⁺) 464 (MH⁺).

Alternative Synthetic Approaches

164 2-(1H-Indazol-4-yl)-4-morpholin-4-yl-6-(4-thiazol-4-ylmethyl-piperazin-1-ylmethyl)-thieno[3,2-d]pyrimidine Via 2-chloro-4-morpholin-4-yl-6-(4-thiazol-4-ylmethyl-piperazin-1-ylmethyl)-thieno[3,2-d]pyrimidine, prepared from 1-thiazol-4-ylmethyl-piperazine, via 2-chloro-4-morpholin-4-yl-6-(4-thiazol-4-ylmethyl-piperazin-1-ylmethyl)-thieno[3,2-d]pyrimidine, prepared according to the following procedure: to a suspension of 4-thiazolecarboxylic acid (500 mg) in THF (10 mL) was added borane-dimethylsulfide complex (0.73 mL). After 24 h the mixture was cooled to 0° C. and quenched by the addition of 2M hydrochloric acid and extracted into ethyl acetate. The organic layers were washed with brine and dried (MgSO₄). The solvent was evaporated and the residue stirred in DCM/MeOH overnight. The mixture was concentrated and the residue purified by flash chromatography to give thiazol-4-yl-methanol (173 mg). To a solution of thiazol-4-yl-methanol (168 mg) in DCM (5 mL) was added triethylamine (0.33 mL) followed by methanesulfonyl chloride (0.17 mL) at 0° C. The mixture was stirred at room temperature for 10 min and diluted with DCM, washed with brine and dried (MgSO₄). The crude product was purified by flash chromatography to give methanesulfonic acid thiazol-4-yl methyl ester (263 mg). To a solution of 2-chloro-4-morpholin-4-yl-6-piperazin-1-ylmethyl-thieno[3,2-d]pyrimidine (300 mg) and methanesulfonic acid thiazol-4-yl methyl ester (213 mg) in MeCN (10 mL) was added potassium carbonate (164 mg) and the mixture heated at 80° C. for 8 h. The cooled mixture was filtered, the solvent evaporated and the residue partitioned between DCM and water. The organic layer was washed with brine, dried (MgSO₄) and the solvent evaporated. The residue was purified by flash chromatography to give the desired product (249 mg).

¹H NMR (400 MHz, CDCl₃) 2.57 (br s, 4H), 3.71 (s, 2H), 3.79 (s, 2H), 3.85 (t, J=4.8 Hz, 4H), 4.02 (t, J=4.8 Hz, 4H), 7.13 (s, 1H), 7.30 (s, 1H), 7.43 (t, J=7.8 Hz, 1H), 7.51 (d, J=8.3 Hz, 1H), 8.21 (d, J=6.9 Hz, 1H), 8.71 (d, J=2.0 Hz, 1H), 8.95 (s, 1H), 10.10 (br s, 1H); MS (ESI⁺) 533.25 (MH⁺).

165 1-{4-[2-(1H-Indazol-4-yl)-4-morpholin-4-yl-thieno[3,2-d]pyrimidin-6-ylmethyl]-piperazin-1-yl}-3-phenoxy-propan-2-ol Via 4-(2-Chloro-4-morpholin-4-yl-thieno[3,2-d]pyrimidin-6-ylmethyl)-piperazine-1-carboxylic acid tert-butyl ester, prepared from 1-BOC-piperazine.

Treatment of 4-[2-(1H-indazol-4-yl)-4-morpholin-4-yl-thieno[3,2-d]pyrimidin-6-ylmethyl]-piperazine-1-carboxylic acid tert-butyl ester with HCl in DCM/MeOH yielded 2-(1H-indazol-4-yl)-4-morpholin-4-yl-6-piperazin-1-ylmethyl-thieno[3,2-d]pyrimidine. A mixture of 2-(1H-indazol-4-yl)-4-morpholin-4-yl-6-piperazin-1-ylmethyl-thieno[3,2-d]pyrimidine (150 mg) and 1,2-epoxy-3-phenoxypropane (40 mg) was suspended in 50% DMF/0.1M sodium phosphate buffer (2 mL) and shaken at 55° C. overnight. After stirring for 24 h the reaction mixture was then diluted with DCM, washed with brine, dried (MgSO₄) and the solvent removed in vacuo. The residue was purified by flash chromatography.

¹H NMR (400 MHz, CDCl₃) 2.50-2.70 (8H, br), 2.70-2.82 (2H, br), 3.85 (2H, s), 3.90-3.93 (4H, m), 3.99-4.01 (2H, m), 4.07-4.14 (5H, m), 6.90-6.98 (3H, m), 7.26-7.30 (2H, m), 7.40 (1H, s), 7.50-7.53 (1H, m), 7.59 (1H, d, J=8.3 Hz), 8.29 (1H, d, J=7.0 Hz), 9.02 (1H, s); MS (ESI$^+$) 568 (MH$^+$).

166 6-[4-(1H-Imidazol-2-ylmethyl)-piperazin-1-ylmethyl]-2-(1H-indazol-4-yl)-4-morpholin-4-yl-thieno[3,2-d]pyrimidine Via 2-chloro-4-morpholin-4-yl-6-piperazin-1-ylmethyl-thieno[3,2-d]pyrimidine, prepared from 1-BOC-piperazine followed by treatment with HCL and subsequent reaction with imidazole-2-carboxaldehyde using standard reductive amination conditions. The amine, 2-chloro-6-[4-(1H-imidazol-2-ylmethyl)-piperazin-1-ylmethyl]-4-morpholin-4-yl-thieno[3,2-d]pyrimidine was subsequently isolated.

$^1$H NMR (400 MHz, CDCl$_3$): 2.55-2.72 (8H, br m), 3.71 (2H, s), 3.89 (2H, s), 3.92-3.96 (4H, m), 4.03-4.11 (4H, m), 7.02 (2H, s), 7.32 (1H, s), 7.51 (1H, t, J=8.0 Hz), 7.59 (1H, d, J=8.3), 8.29 (1H, d, J=6.6 Hz), 9.03 (1H, s), 10.10 (1H, br m); MS (ESI$^+$) 516 (MH$^+$).

167 6-[4-(3H-Imidazol-4-ylmethyl)-piperazin-1-ylmethyl]-2-(1H-indazol-4-yl)-4-morpholin-4-yl-thieno[3,2-d]pyrimidine In a similar manner to 167 (PI1343) 2-chloro-6-[4-(3H-imidazol-4-ylmethyl)-piperazin-1-ylmethyl]-4-morpholin-4-yl-thieno[3,2-d]pyrimidine was prepared by reductive amination with 5-formyl-imidazole-1-carboxylic acid tert-butyl ester followed by removal of the BOC group using HCl.

$^1$H NMR (400 MHz, d$_6$-DMSO) 2.45 (br s, 4H), 3.29 (s, 2H), 3.42 (br s, 4H), 3.84 (m, 6H), 3.99 (t, 4H), 7.46 (m, 3H), 7.47 (s, 1H), 7.65 (d, J=7.4 Hz, 1H), 8.21 (d, J=7.4 Hz, 1H), 8.86 (s, 1H), 13.20 (s, 1H). MS (ESI$^+$) 516 (MH$^+$).

Synthesis via Alkyl Bromide (Route 3)

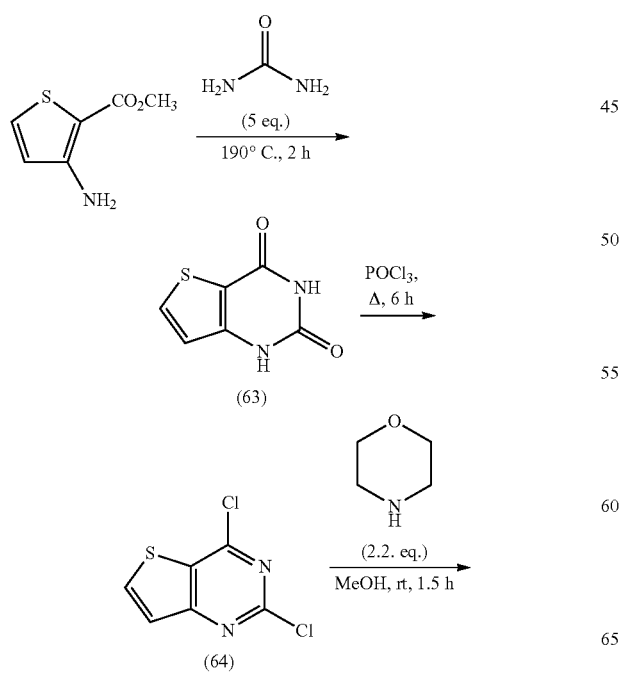

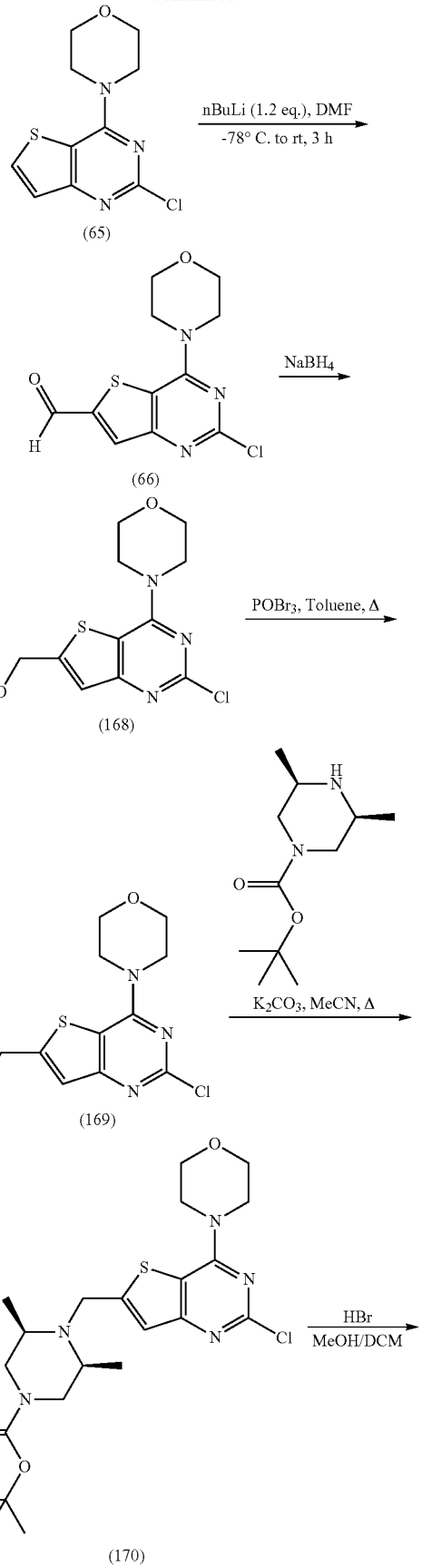

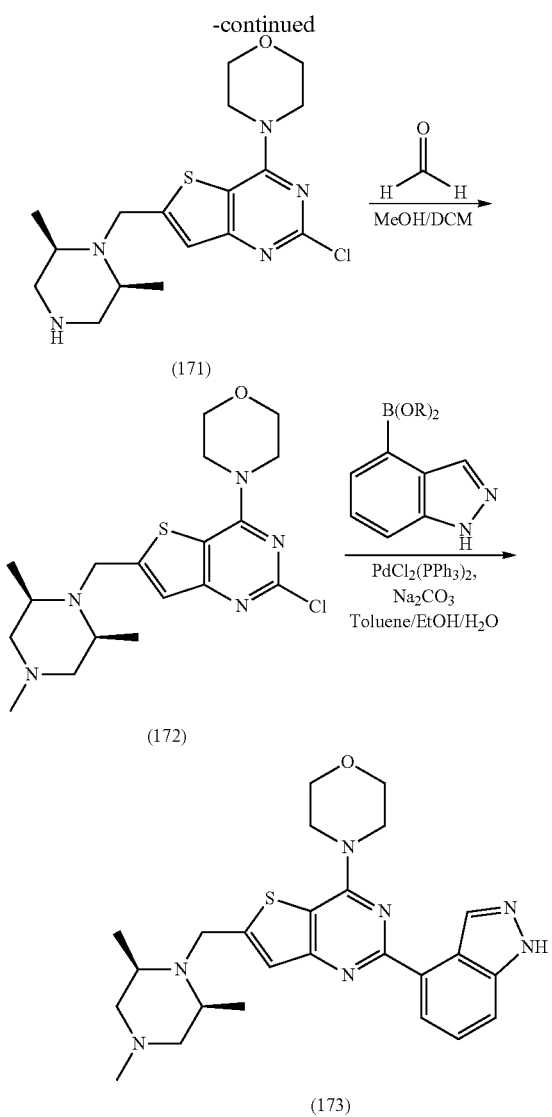

(171)

(172)

(173)

173 2-(1H-Indazol-4-yl)-4-morpholin-4-yl-6-((2S, 6R)-2,4,6-trimethyl-piperazin-1-ylmethyl)-thieno[3, 2-d]pyrimidine To (66) (1.5 g) in ethanol (30 mL) was added sodium borohydride (1 g). After 4 h the reaction mixture was quenched with brine and the resulting solid was collected by filtration, and air dried to furnish 168 (2-chloro-4-morpholin-4-yl-thieno[3,2-d]pyrimidin-6-yl)-methanol (1.42 g).

To a solution of 168 (1.42 g) in toluene (14 ml), warmed to 40° C., was added phosphorous tribromide (0.16 ml). The resulting mixture was then heated to 100° C. for 6 h, was cooled, diluted with chloroform, washed with brine, and dried (MgSO$_4$). The solvent was removed in vacuo to yield 6-bromomethyl-2-chloro-4-morpholin-4-yl-thieno[3,2-d]pyrimidine, 169 (1.40 g).

A mixture of (3R,5S)-3,5-dimethyl-piperazine-1-carboxylic acid tert-butyl ester (0.92 g), 6-bromomethyl-2-chloro-4-morpholin-4-yl-thieno[3,2-d]pyrimidine (1 g) and potassium carbonate (1.59 g) in MeCN (10 ml) was heated to reflux for 5 days. The reaction mixture was subsequently cooled, diluted with chloroform, washed with brine and dried (MgSO$_4$), and the solvent was removed in vacuo. The residue was purified by flash column chromatography to yield (3S, 5R)-4-(2-chloro-4-morpholin-4-yl-thieno[3,2-d]pyrimidin-6-ylmethyl)-3,5-dimethyl-piperazine-1-carboxylic acid tert-butyl ester, 170 (1.2 g). Treatment of this compound with HCl in DCM/MeOH produced 2-chloro-6-(2S,6R)-2,6-dimethyl-piperazin-1-ylmethyl)-4-morpholin-4-yl-thieno[3,2-d]pyrimidine, 171, which was then methylated using 37% formaldehyde solution and sodium borohydride in MeOH, furnishing 172.

$^1$H NMR (400 MHz, CDCl$_3$) 1.17 (6H, d), 1.92 (2H, t), 2.3 (3H, s), 2.73 (2H, d), 2.83 (2H, m), 3.95 (4H, m), 4.03 (4H, m), 4.18 (2H, s), 7.36 (1H, s), 7.48 (1H, t), 7.56 (1H, d), 8.26 (1H, d), 9.00 (1H, s), 10.40 (1H, br m); MS (ESI$^+$) 478 (MH$^+$).

174 {4-[2-(1H-Indazol-4-yl)-4-morpholin-4-yl-thieno[3,2-d]pyrimidin-6-ylmethyl]-1-methanesulfonyl-piperazin-2-yl}-methanol Via [4-(2-Chloro-4-morpholin-4-yl-thieno[3,2-d]pyrimidin-6-ylmethyl)-1-methanesulfonyl-piperazin-2-yl]-methanol, prepared from (1-methanesulfonyl-piperazin-2-yl)-methanol.

Amine preparation: To a suspension of piperazine-2-carboxylic acid dihydrochloride (10.0 g) in 1,4-dioxane (100 mL) and water (50 mL), cooled down to 0° C., was slowly added 17M sodium hydroxide solution (8.6 mL) followed by di-tert-butyldicarbonate (11.8 g). The reaction mixture was warmed to room temperature and stirred for 5 h. Triethylamine (13.7 mL) followed by methanesulfonyl chloride (3.8 mL) was then added. After stirring for 24 h the reaction mixture was concentrated down, the residue diluted with ethyl acetate, washed with 2M hydrochloric acid, brine, dried (MgSO$_4$) and the solvent removed in vacuo to yield crude 4-methanesulfonyl-piperazine-1,3-dicarboxylic acid 1-tert-butyl ester (8.46 g). This was subsequently dissolved in DMF (50 mL), and was treated with added potassium carbonate (7.5 g) and iodomethane (8.5 mL). After stirring for 24 h the reaction mixture was diluted with ethyl acetate, washed with water, brine, dried (MgSO$_4$) and the solvent removed in vacuo. The residue was purified by flash chromatography to yield 4-methanesulfonyl-piperazine-1,3-dicarboxylic acid 1-tert-butyl ester 3-methyl ester (3.27 g).

To a suspension of lithium aluminium hydride (0.75 g) in THF (30 mL) was added a solution of 4-methanesulfonyl-piperazine-1,3-dicarboxylic acid 1-tert-butyl ester 3-methyl ester (3.2 g) in THF (20 mL) at 0° C. The reaction mixture was subsequently warmed to room temperature. After stirring for 2.5 h, ammonium chloride solution (5 mL) was added to the reaction mixture, which was then filtered through celite, washed with brine, dried (MgSO$_4$) and the solvent removed in vacuo. The residue was purified by flash chromatography to yield 3-hydroxymethyl-4-methanesulfonyl-piperazine-1-carboxylic acid tert-butyl ester (1.13 g). Treatment of this compound with HCl in DCM/MeOH yielded the desired amine, which was isolated as the hydrochloride salt.

$^1$H NMR (400 MHz, CDCl$_3$) 2.38 (1H, m), 2.50 (1H, dd, J=3.9 Hz, 7.7 Hz), 2.70 (1H, br s), 2.97 (1H, m), 3.00 (3H, s), 3.06 (1H, d, J=11.6 Hz), 3.52 (1H, m), 3.72 (1H, d, J=12.8 Hz), 3.86 (2H, m), 3.94 (5H, m), 4.01 (1H, m), 4.10 (5H, m), 7.40 (1H, s), 7.51 (1H, t, J=7.8 Hz), 7.60 (1H, d, J=8.2 Hz); 8.27 (1H, d, J=7.2 Hz); 9.02 (1H, s); 10.16 (1H, br s). MS (ESI$^+$) 544 (MH$^+$).

175 2-(1H-Indazol-4-yl)-6-(4-methanesulfonyl-3-methoxymethyl-piperazin-1-ylmethyl)-4-morpholin-4-yl-thieno[3,2-d]pyrimidine Via 2-Chloro-6-(4-methanesulfonyl-3-methoxymethyl-piperazin-1-ylmethyl)-4-morpholin-4-yl-thieno[3,2-d]pyrimidine, prepared from 1-methanesulfonyl-2-methoxymethyl-piperazine Amine preparation: to a THF (5 mL) solution of 3-hydroxymethyl-4-methanesulfonyl-piperazine-1-carboxylic acid tert-butyl ester (0.30 g, described for the production of 174) was added sodium hydride (0.043 g). The reaction mixture was stirred for 20 min and then iodomethane (0.19 mL) was added. After stirring for 24 h the reaction mixture was then diluted with DCM, washed with brine, dried (MgSO$_4$) and the solvent removed in vacuo. The residue was purified by flash chromatography to yield 4-methanesulfonyl-3-methoxymethyl-piperazine-1-carboxylic acid tert-butyl ester (0.254 g). Treatment of this compound with HCl in DCM/MeOH yielded the desired amine, isolated as the hydrochloride salt.

$^1$H NMR (400 MHz, CDCl$_3$): 2.34 (1H, m), 2.42 (1H, dd, J=3.9, 7.6 Hz), 2.94 (2H, m), 3.07 (3H, s), 3.28 (1H, m), 3.40 (3H, s), 3.74 (1H, d, J=12.9 Hz), 3.84 (2H, m), 3.94 (4H, m), 4.00 (1H, t, J=5.1 Hz), 4.10 (4H, m), 4.20 (1H, m), 7.40 (1H, s), 7.52 (1H, t, J=7.8 Hz), 7.60 (1H, d, J=8.3 Hz), 8.28 (1H, d, J=7.1 Hz), 9.00 (1H, s), 10.15 (1H, br s); MS (ESI$^+$) 558 (MH$^+$).

EXAMPLE 3

Biological Testing

Compounds of the invention, prepared as described in the preceding Examples, were submitted to the following series of biological assays:

(i) PI3K Biochemical Screening

Compound inhibition of PI3K was determined in a radiometric assay using purified, recombinant enzyme and ATP at a concentration of 1 uM. All compounds were serially diluted in 100% DMSO. The kinase reaction was incubated for 1 h at room temperature, and the reaction was terminated by the addition of PBS. IC$_{50}$ values were subsequently determined using sigmoidal dose-response curve fit (variable slope). All of the compounds exemplified had an IC$_{50}$ against PI3K of 510 uM or less. In particular, all of the compounds tested against the p110 δ isoform of PI3K had an IC$_{50}$ of 0.1 μM or less.

(ii) Cellular Proliferation Inhibition

Cells were seeded at optimal density in a 96 well plate and incubated for 4 days in the presence of test compound. Alamar Blue™ was subsequently added to the assay medium, and cells were incubated for 6 h before reading at 544 nm excitation, 590 nm emission. EC$_{50}$ values were calculated using a sigmoidal dose response curve fit. All the compounds tested had an EC$_{50}$s of 50 uM or less in the range of cell lines utilized.

(iii) Caco-2 Permeability

Caco-2 cells were seeded onto Millipore Multiscreen plates at 1×10$^5$ cells/cm$^2$, and were cultured for 20 days. Assessment of compound permeability was subsequently conducted. The compounds were applied to the apical surface (A) of cell monolayers and compound permeation into the basolateral (B) compartment was measured. This was performed in the reverse direction (B-A) to investigate active transport. A permeability coefficient value, P$_{app}$, for each compound, a measure of the rate of permeation of the compound across the membrane, was calculated. Compounds were grouped into low (P$_{app}$</=1.0×10$^6$ cm/s) or high (P$_{app}$>/=1.0×10$^6$ cm/s) absorption potential based on comparison with control compounds with established human absorption.

For assessment of a compound's ability to undergo active efflux, the ratio of basolateral (B) to apical (A) transport compared with A to B was determined. Values of B-A/A-B>/=1.0 indicated the occurrence of active cellular efflux. All of the compounds tested through the Caco-2 permeability screen had P$_{app}$ values >/=1.0×10$^6$ cm/s. One compound assessed through the bidirectional assay, PI540, had an B-A/A-B asymmetry index of less than 1.0, indicating that the compound does not undergo active cellular efflux.

(iv) Hepatocyte Clearance

Suspensions of cryopreserved human hepatocytes were used. Incubations were performed at compound concentration of 1 mM or 3 μM at a cell density of 0.5×10$^6$ viable cells/mL. The final DMSO concentration in the incubation was 0.25%. Control incubations were also performed in the absence of cells to reveal any non-enzymatic degradation. Duplicate samples (50 μL) were removed from the incubation mixture at 0, 5, 10, 20, 40 and 60 minutes (control sample at 60 minutes only) and added to MeOH—containing internal standard (100 μL)—to terminate the reaction. Tolbutamide, 7-hydroxycoumarin, and testosterone were used as control compounds. Samples were centrifuged and the supernatants at each time point pooled for analysis by LC-MSMS. From a plot of ln peak area ratio (parent compound peak area/internal standard peak area) against time, intrinsic clearance (CL$_{int}$) was calculated as follows: CL$_{int}$ (μl/min/million cells)=V×k, where k is the elimination rate constant, obtained from the gradient of ln concentration plotted against time; V is a volume term derived from the incubation volume and is expressed as uL 10$^6$ cells$^{-1}$.

Compounds were classified with low (CL</=4.6 μL/min/10$^6$ cells), medium (CL>/=4.6; </=25.2 μl/min/10$^6$ cells) and high (>/=25.2 μl/min/10$^6$ cells) clearance. The majority of the tested compounds of the invention were determined to have low hepatocyte clearance.

(v) Cytochrome P450 Inhibition

Compounds of the invention were screened against five CYP450 targets (1A2, 2C9, 2C19, 2D6, 3A4) at 10 concentrations in duplicate, with a top concentration of 100 uM being used. Standard inhibitors (furafylline, sulfaphenazole, tranylcypromine, quinidine, ketoconazole) were used as controls. Plates were read using a BMG LabTechnologies PolarStar in fluorescence mode. The majority of the tested compounds assessed in this assay displayed weak activity (IC$_{50}$>/=5 uM) against all isoforms of CYP450.

(vi) Cytochrome P450 Induction

Freshly isolated human hepatocytes from a single donor were cultured for 48 h prior to addition of test compound at three concentrations and were incubated for 72 h. Probe substrates for CYP3A4 and CYP1A2 were added for 30 minutes and 1 h before the end of the incubation. At 72 h, cells and media were removed and the extent of metabolism of each probe substrate quantified by LC-MS/MS. The experiment was controlled by using inducers of the individual P450s incubated at one concentration in triplicate. The compounds of the invention assessed in this assay showed negligible effects on induction of cytochrome P450 enzymes.

(vii) Plasma Protein Binding

Solutions of test compound (5 um, 0.5% final DMSO concentration) were prepared in buffer and 10% plasma (v/v in buffer). A 96 well HT dialysis plate was assembled so that each well was divided in two by a semi-permeable cellulose membrane. The buffer solution was added to one side of the membrane and the plasma solution to the other side; incubations were then conducted at 37° C. over 2 h in triplicate. The cells were subsequently emptied, and the solutions for each batch of compounds were combined into two groups (plasma-free and plasma-containing) then analysed by LC-MSMS using two sets of calibration standards for plasma-free (6 points) and plasma-containing solutions (7 points). The fraction unbound value for each compound was calculated: highly protein bound compounds (>/=90% bound) had an Fu </=0.1. The compounds of the invention assessed in this assay had Fu values >/=0.1.

(viii) hERG Channel Blockage

Compounds of the invention were evaluated for their ability to modulate rubidium efflux from HEK-294 cells stably expressing hERG potassium channels using established flux methodology. Cells were prepared in medium containing RbCl and were plated into 96-well plates and grown overnight to form monolayers. The efflux experiment was initiated by aspirating the media and washing each well with 3×100 µL of pre-incubation buffer (containing low [K$^+$]) at room temperature.

Following the final aspiration, 50 µL of working stock (2×) compound was added to each well and incubated at room temperature for 10 minutes. 50 µL of stimulation buffer (containing high [K+]) was then added to each well giving the final test compound concentrations. Cell plates were then incubated at room temperature for a further 10 minutes. 80 µL of supernatant from each well was then transferred to equivalent wells of a 96-well plate and analysed via atomic emission spectroscopy. Compounds were screened as 10 pt duplicate IC$_{50}$ curves, n=2, from a top concentration of 100 µM.

EXAMPLE 4

Tablet Composition

Tablets, each weighing 0.15 g and containing 25 mg of a compound of the invention were manufactured as follows:
Composition for 10,000 Tablets
Active compound (250 g)
Lactose (800 g)
Corn starch (415 g)
Talc powder (30 g)
Magnesium stearate (5 g)

The active compound, lactose and half of the corn starch were mixed. The mixture was then forced through a sieve 0.5 mm mesh size. Corn starch (10 g) is suspended in warm water (90 mL). The resulting paste was used to granulate the powder. The granulate was dried and broken up into small fragments on a sieve of 1.4 mm mesh size. The remaining quantity of starch, talc and magnesium was added, carefully mixed and processed into tablets.

EXAMPLE 5

Injectable Formulation

Formulation A

| Active compound | 200 mg |
| Hydrochloric Acid Solution 0.1M or | |
| Sodium Hydroxide Solution 0.1M q.s. to pH | 4.0 to 7.0 |
| Sterile water q.s. to | 10 mL |

The compound of the invention was dissolved in most of the water (35° 40° C.) and the pH adjusted to between 4.0 and 7.0 with the hydrochloric acid or the sodium hydroxide as appropriate. The batch was then made up to volume with water and filtered through a sterile micropore filter into a sterile 10 mL amber glass vial (type 1) and sealed with sterile closures and overseals.

Formulation B

| Active Compound | 125 mg |
| Sterile, Pyrogen-free, pH 7 Phosphate | |
| Buffer, q.s. to | 25 mL |
| Active compound | 200 mg |
| Benzyl Alcohol | 0.10 g |
| Glycofurol 75 | 1.45 g |
| Water for injection q.s to | 3.00 mL |

The active compound was dissolved in the glycofurol. The benzyl alcohol was then added and dissolved, and water added to 3 mL. The mixture was then filtered through a sterile micropore filter and sealed in sterile 3 mL glass vials (type 1).

EXAMPLE 6

Syrup Formulation

| Active compound | 250 mg |
| Sorbitol Solution | 1.50 g |
| Glycerol | 2.00 g |
| Sodium benzoate | 0.005 g |
| Flavour | 0.0125 mL |
| Purified Water q.s. to | 5.00 mL |

The compound of the invention was dissolved in a mixture of the glycerol and most of the purified water. An aqueous solution of the sodium benzoate was then added to the solution, followed by addition of the sorbital solution and finally the flavour. The volume was made up with purified water and mixed well.

The invention claimed is:

1. A pharmaceutical composition comprised of a fused pyrimidine compound of formula (I):

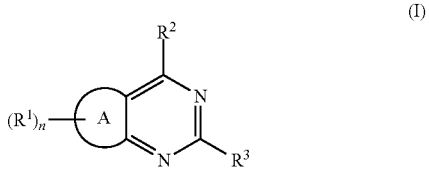

wherein
A represents a thiophene or furan ring;
n is 1 or 2;
R$^1$ is a group of formula:

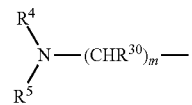

wherein m is 0 or 1;

$R^{30}$ is H or $C_1$-$C_6$ alkyl;

$R^4$ and $R^5$ form, together with the N atom to which they are attached, a 5- or 6-membered saturated N-containing heterocyclic group which includes 0 or 1 additional heteroatoms selected from N, S and O, which may be fused to a benzene ring and which is unsubstituted or substituted; or one of $R^4$ and $R^5$ is alkyl and the other is a 5- or 6-membered saturated N-containing heterocyclic group as defined above or an alkyl group which is substituted by a 5- or 6-membered saturated N-containing heterocyclic group as defined above;

$R^2$ is selected from:

(a)

wherein $R^6$ and $R^7$ form, together with the nitrogen atom to which they are attached, a morpholine, thiomorpholine, piperidine, piperazine, oxazepane or thiazepane group which is unsubstituted or substituted; and

(b)

wherein Y is a $C_2$-$C_4$ alkylene chain which contains, between constituent carbon atoms of the chain and/or at one or both ends of the chain, 1 or 2 heteroatoms selected from O, N and S, and which is unsubstituted or substituted; and $R^3$ is an indazole group which is unsubstituted or substituted;

or a pharmaceutically acceptable salt thereof, and a carrier, diluent or excipient selected from calcium carbonate, sodium carbonate, calcium phosphate, sodium phosphate, cellulose, lactose, sodium carboxymethylcellulose, talc, calcium stearate, glyceryl monostearate, methylcellulose, hydroxypropylmethyl-cellulose, polyvinylpyrrolidone, gum tragacanth, gum acacia, glyceryl distearate, polysorbate, lauryl sulphate and magnesium stearate.

2. The pharmaceutical composition of claim 1 formulated in a capsule.

3. The pharmaceutical composition of claim 1 formulated in a tablet.

4. The pharmaceutical composition of claim 1 formulated in the form of oil-in-water emulsion.

5. The pharmaceutical composition formulated of claim 1 comprising a carrier, diluent or excipient selected from lactose, sodium carboxymethylcellulose, and magnesium stearate.

* * * * *